US009194826B2

(12) United States Patent
Kaga et al.

(10) Patent No.: US 9,194,826 B2
(45) Date of Patent: Nov. 24, 2015

(54) ELECTRON BEAM APPARATUS AND SAMPLE OBSERVATION METHOD USING THE SAME

(75) Inventors: Toru Kaga, Tokyo (JP); Kenji Terao, Tokyo (JP); Masahiro Hatakeyama, Tokyo (JP); Kenji Watanabe, Tokyo (JP); Yoshihiko Naito, Tokyo (JP); Takeshi Murakami, Tokyo (JP); Norio Kimura, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 0 days.

(21) Appl. No.: 12/103,354

(22) Filed: Apr. 15, 2008

(65) Prior Publication Data

US 2008/0251718 A1    Oct. 16, 2008

(30) Foreign Application Priority Data

Apr. 16, 2007  (JP) ................................ 2007-107564
Jun. 20, 2007  (JP) ................................ 2007-162528

(51) Int. Cl.
*G21K 5/04*      (2006.01)
*G01N 23/203*    (2006.01)
*G01N 23/225*    (2006.01)
*H01J 37/28*     (2006.01)

(52) U.S. Cl.
CPC .......... *G01N 23/203* (2013.01); *G01N 23/2251* (2013.01); *H01J 37/28* (2013.01); *G01N 2223/6116* (2013.01); *H01J 2237/004* (2013.01); *H01J 2237/022* (2013.01); *H01J 2237/2446* (2013.01); *H01J 2237/2817* (2013.01)

(58) Field of Classification Search
None
See application file for complete search history.

(56) References Cited

U.S. PATENT DOCUMENTS

| 6,038,018 | A  | * | 3/2000 | Yamazaki | H01J 37/28 356/237.1 |
| 6,232,787 | B1 | * | 5/2001 | Lo | H01J 37/268 250/311 |
| 6,252,412 | B1 | * | 6/2001 | Talbot | G06T 7/0004 324/754.22 |
| 6,583,634 | B1 | * | 6/2003 | Nozoe | G01R 31/307 324/754.22 |
| 6,700,122 | B2 | * | 3/2004 | Matsui | H01J 37/28 250/310 |
| 7,019,294 | B2 | * | 3/2006 | Koyama | G01R 31/311 250/306 |

(Continued)

FOREIGN PATENT DOCUMENTS

| EP | 1 296 352 A1 | 3/2003 |
| JP | 64-31339 A | 2/1989 |

(Continued)

OTHER PUBLICATIONS

Japanese Office Action dated Jul. 26, 2011, issued in corresponding Japanese Patent Application No. 2007-107564.

(Continued)

*Primary Examiner* — Andrew Smyth
(74) *Attorney, Agent, or Firm* — Westerman, Hattori, Daniels & Adrian, LLP

(57) ABSTRACT

The electron beam apparatus is provided with a stage for mounting a sample thereon, a primary optical system for generating an electron beam having an irradiation area and irradiating the electron beam onto the sample, a secondary optical system for detecting electrons which have been generated through the irradiation of the electron beam onto the sample and have acquired structural information of the sample and acquiring an image of the sample about a viewing area and an irradiation area changing section for changing the position of the irradiation area with respect to the viewing area.

10 Claims, 33 Drawing Sheets

(56) References Cited

U.S. PATENT DOCUMENTS

| | | | |
|---|---|---|---|
| 7,202,690 B2 * | 4/2007 | Yamamoto | G01R 31/2812 324/501 |
| 2002/0027440 A1 | 3/2002 | Shinada et al. | |
| 2002/0100871 A1 * | 8/2002 | Aita | G01N 27/419 250/309 |
| 2002/0134936 A1 * | 9/2002 | Matsui | H01J 37/28 250/310 |
| 2002/0158198 A1 * | 10/2002 | Kohama | G01N 23/225 250/307 |
| 2002/0175296 A1 * | 11/2002 | Kimura | H01J 37/3053 250/492.21 |
| 2003/0057971 A1 * | 3/2003 | Nishiyama | G01R 31/305 324/750.02 |
| 2003/0206027 A1 * | 11/2003 | Nozoe | G01R 31/307 324/754.22 |
| 2004/0129879 A1 * | 7/2004 | Furiki | H01J 37/261 250/310 |
| 2005/0029451 A1 * | 2/2005 | Nagahama | H01J 37/28 250/310 |
| 2005/0045821 A1 * | 3/2005 | Noji | G01N 23/225 250/311 |
| 2005/0051724 A1 * | 3/2005 | Nakasuji | G01N 23/2251 250/310 |
| 2005/0104017 A1 * | 5/2005 | Kimba | G06T 7/001 250/559.07 |
| 2005/0130546 A1 * | 6/2005 | Osoegawa | H01J 9/44 445/6 |
| 2005/0190310 A1 | 9/2005 | Koyama et al. | |
| 2005/0194536 A1 * | 9/2005 | Furiki | H01J 37/261 250/311 |
| 2005/0218325 A1 * | 10/2005 | Nishiyama | H01J 37/026 250/311 |
| 2006/0017452 A1 * | 1/2006 | Yamamoto | G01R 31/2812 324/750.3 |
| 2006/0102838 A1 * | 5/2006 | Nakasuji | G01N 23/2251 250/307 |
| 2006/0163480 A1 * | 7/2006 | Koyama | G01R 31/311 250/310 |
| 2006/0169900 A1 * | 8/2006 | Noji | G01N 23/225 250/310 |
| 2007/0138390 A1 * | 6/2007 | Nishiyama | H01J 37/026 250/310 |
| 2007/0187600 A1 * | 8/2007 | Nagahama | H01J 37/28 250/310 |
| 2009/0050802 A1 * | 2/2009 | Noji | G01R 31/307 250/307 |
| 2009/0166557 A1 * | 7/2009 | Makino | H01J 37/026 250/442.11 |
| 2010/0213370 A1 | 8/2010 | Nakasuji et al. | |

FOREIGN PATENT DOCUMENTS

| | | | | |
|---|---|---|---|---|
| JP | 02275630 A | * | 11/1990 | H01L 21/304 |
| JP | 7-161598 A | | 6/1995 | |
| JP | 8-298093 A | | 11/1996 | |
| JP | 8-325733 A | | 12/1996 | |
| JP | 10197462 A | * | 7/1998 | G01N 23/223 |
| JP | 10-294345 A | | 11/1998 | |
| JP | 11-16533 A | | 1/1999 | |
| JP | 2002-289128 A | | 10/2002 | |
| JP | 2003-166947 A | | 6/2003 | |
| JP | 2005-164451 A | | 6/2005 | |
| TW | 200636232 A | | 10/2006 | |
| WO | 02/01596 A1 | | 1/2002 | |
| WO | 2007/086400 A1 | | 8/2007 | |

OTHER PUBLICATIONS

Japanese Office Action dated Dec. 6, 2011, issued in corresponding Japanese Patent Application No. 2007-162528.

Taiwanese Office Action dated Jun. 5, 2013, issued in corresponding Taiwanese Patent Application No. 097110481.

Korean Office Action dated Feb. 28, 2014, issued in corresponding Korean App No. 10-2008-0034830 (5 pages).

* cited by examiner

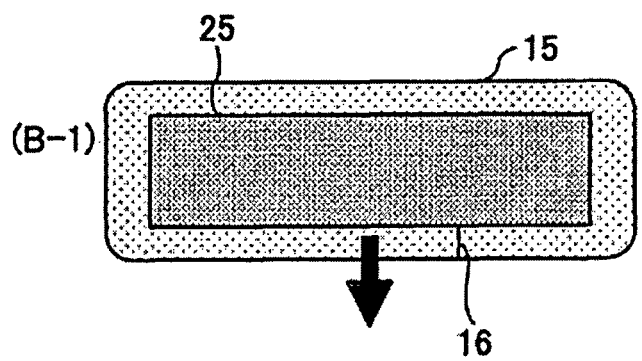
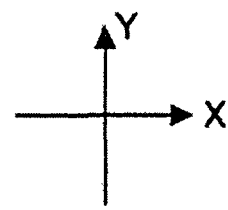
FIG. 2B

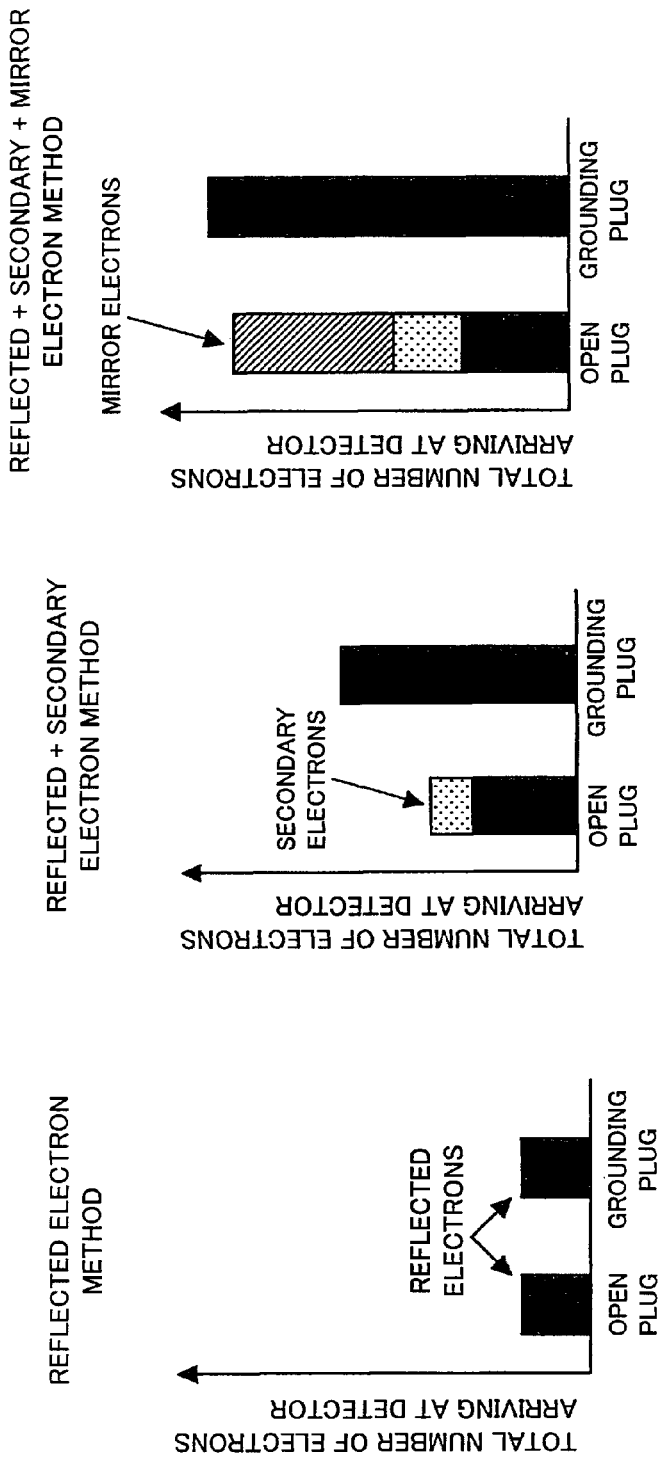

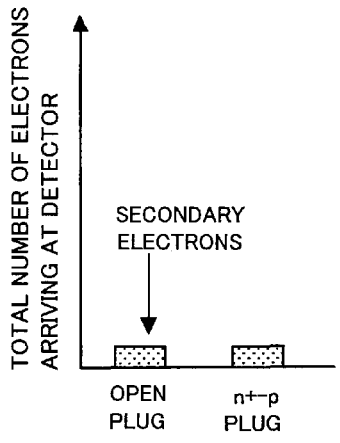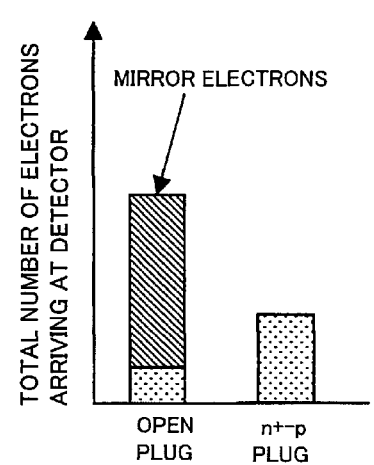
FIG. 15A  FIG. 15B
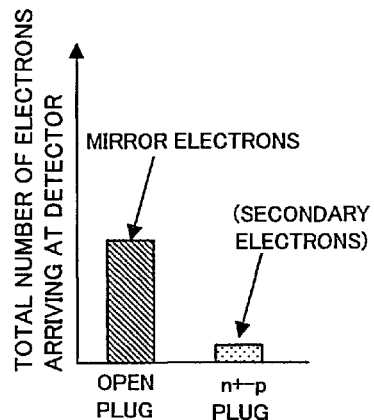
FIG. 16

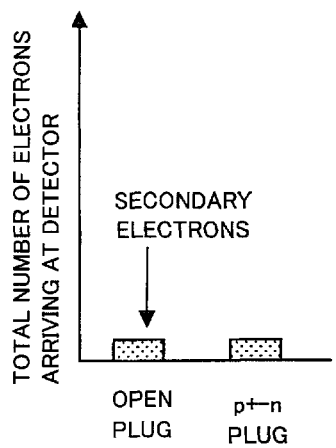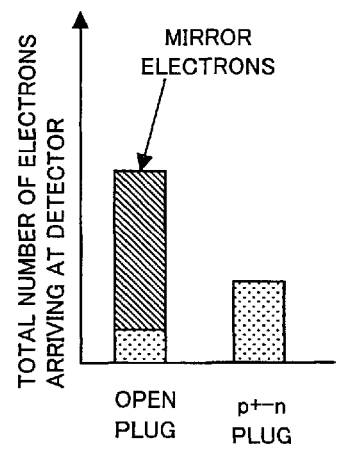
FIG. 21A  FIG. 21B
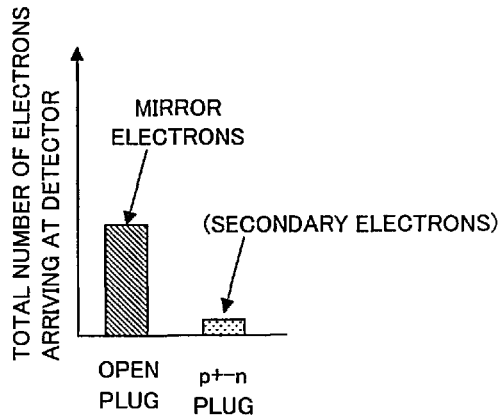
FIG. 22

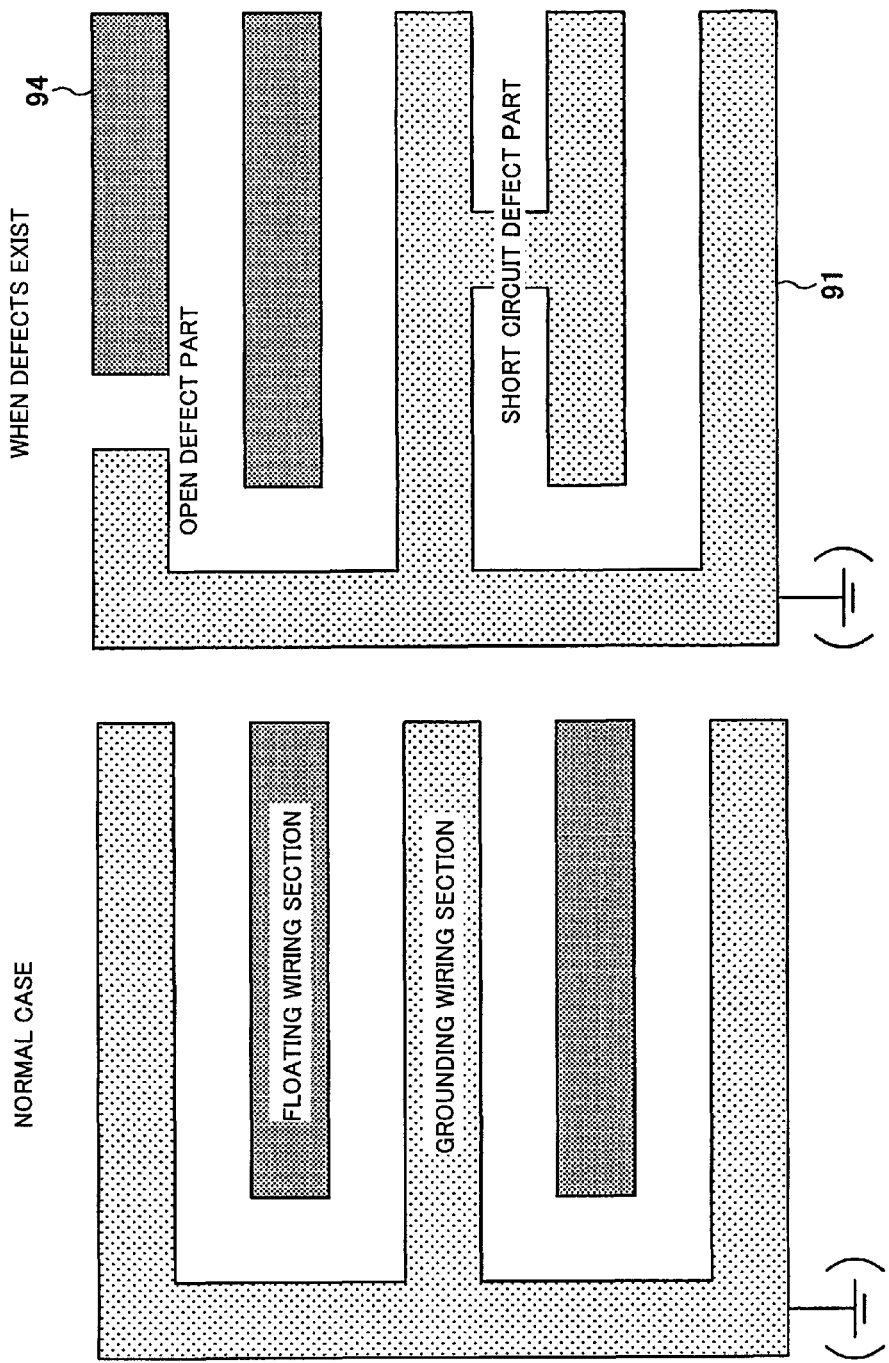

ELECTRON BEAM APPARATUS AND SAMPLE OBSERVATION METHOD USING THE SAME

BACKGROUND OF THE INVENTION

1. Field of the Invention

The present invention relates to an electron beam apparatus using an electron beam and a sample observation method using the same.

2. Description of the Related Arts

"Inspection Technique"

Inspection apparatuses are conventionally used to inspect defects of semiconductor wafers. A known inspection apparatus is equipped with a primary optical system that irradiates an electron beam onto a semiconductor wafer and a secondary optical system that detects secondary electrons or reflected electrons emitted from the semiconductor wafer and generates image data from a detection signal thereof.

Wafer inspection apparatuses using electron beams are known to apply a processing method called "predosing" or "precharging" that irradiates, when observing a semiconductor wafer, charged particles onto the semiconductor wafer before the observation so that the wafer surface is charged uniformly. This kind of technique is disclosed in International Publication WO 2002/001596.

In order to perform predosing or precharging processing, a precharging unit is provided adjacent to a barrel which is an electron beam source and the precharging unit irradiates the semiconductor wafer with charged particles before observing the wafer through irradiation of an electron beam. This eliminates variations in charge, makes the charged state of the semiconductor wafer surface uniform and can thereby obtain a uniform image with less image variations.

However, according to the configuration described in aforementioned International Publication WO 2002/001596, the irradiation area where charged particles are irradiated from the precharging unit is set to be by far wider than the field of view which is the detection area of a detector of the secondary optical system. Since the irradiation area of precharging is wide, the area outside the observed portion is also charged up. Repeating precharging may destroy elements on the wafer.

Furthermore, although an optimum amount of precharging varies depending on a wiring material and insulating material of the wafer, the amount of dosing of charged particles irradiated from the precharging unit cannot be controlled precisely.

Furthermore, since the precharging unit is provided in addition to the barrel which is the electron beam source, replacement of the electron source is complicated. Furthermore, since wafer inspection using an electron beam is carried out in a vacuum atmosphere, it is necessary to additionally perform vacuuming of the space where the precharging unit is installed.

"Removal of Foreign Matter"

The present invention relates to a method of eliminating foreign matter on a sample surface and a charged particle beam apparatus used for this method, and more particularly, to a method of eliminating foreign matter on the sample surface by means of electrostatic adsorption using charging of foreign matter and a charged particle beam apparatus used for this method.

Surface inspection apparatuses are conventionally used to detect foreign matter from a wafer or the like. A known surface inspection apparatus irradiates a laser beam onto a substrate surface such as a wafer, detects scattered reflected light of the laser beam and detects foreign matter. Such a surface inspection apparatus is disclosed, for example, in Japanese Patent Laid-Open No. 2003-166947.

However, the surface inspection apparatus described in Japanese Patent Laid-Open No. 2003-166947 can detect foreign matter, yet gives no consideration to removal of the foreign matter after detection of the foreign matter. Even if the surface inspection apparatus detects foreign matter, a substrate where the foreign matter is detected cannot be shipped as is unless the detected foreign matter is removed. Thus causes yield to degrade.

SUMMARY OF THE INVENTION

It is an object of the present invention to provide an electron beam apparatus capable of providing a primary optical system also with a precharging function, thereby omitting the installation of a precharging unit, and further controlling an area and a quantity of precharging for a sample and performing optimum precharging according to the sample.

The electron beam apparatus according to an aspect of the present invention is provided with a stage for mounting a sample thereon, a primary optical system for generating an electron beam having an irradiation area and irradiating the electron beam onto the sample, a secondary optical system for detecting electrons which have been generated through irradiation of the electron beam onto the sample and have acquired structural information of the sample and for acquiring an image of the sample about a viewing area, and an irradiation area changing section for changing a position of the irradiation area with respect to the viewing area.

Another aspect of the present invention is a sample observation method of observing a sample based on an acquired image which includes mounting the sample on a stage, generating an electron beam having an irradiation area and irradiating the electron beam onto the sample, acquiring an image of the sample about a viewing area by detecting electrons which have been generated through irradiation of the electron beam and have acquired structural information of the sample, and changing the position of the irradiation area with respect to the viewing area.

It is another object of the present invention to provide a method of removing foreign matter on a sample surface which detects foreign matter on the sample surface and removes the detected foreign matter on the sample surface, and a charged particle beam apparatus used for this method.

An aspect of the present invention is a method of removing foreign matter on a sample surface irradiated with a charged particle beam, which includes acquiring charge information on the sample surface, detecting the foreign matter on the sample surface based on the acquired charge information, moving the sample in a horizontal direction, and charging an adsorption electrode facing and close to the sample surface with a polarity different from a charge polarity of the foreign matter and thereby electrostatically adsorbing the foreign matter which approaches the adsorption electrode.

A further aspect of the present invention is a charged particle beam apparatus for removing foreign matter on a sample surface irradiated with a charged particle beam, including a stage for mounting a sample thereon in a horizontally movable manner, a charge information acquisition section for acquiring charge information on the sample surface, a foreign matter detection section for detecting foreign matter on the sample surface based on the charge information, and an adsorption electrode facing the stage, wherein the adsorption electrode is charged with a polarity different from a charge polarity of the foreign matter when the foreign matter on the sample surface approaches as the stage moves so that the adsorption electrode electrostatically adsorbs the foreign matter.

As described hereafter, other aspects of the invention exist. Thus, this summary of the invention is intended to provide a few aspects of the invention and is not intended to limit the scope of the invention described and claimed herein.

BRIEF DESCRIPTION OF THE DRAWINGS

The accompanying drawings are incorporated in and constitute a part of this specification. The drawings exemplify certain aspects of the invention and, together with the description, serve to explain some principles of the invention. As described hereafter, other aspects of the invention exist. Thus, this summary of the invention is intended to provide a few aspects of the invention and is not intended to limit the scope of the invention described and claimed herein.

FIGS. 2A to 2C show various embodiments about a positional relationship between an irradiation area of an electron beam and a viewing area of a secondary optical system; FIG. 2A showing an embodiment where the irradiation area precedes the viewing area, FIG. 2B showing an embodiment where a precharging area is small and FIG. 2C showing an embodiment where the viewing area precedes the irradiation area;

FIG. 3A showing a relationship between a surface potential of a sample and the number of electrons arriving at a detector and FIG. 3B showing a relationship between a time of electron beam irradiation onto the sample and the number of electrons arriving at the detector;

FIG. 5A showing a cross-sectional view of a wafer in which a grounding plug and an open plug are formed and FIG. 5B showing a variation of surface potential of the wafer when an electron beam is irradiated;

FIGS. 8A to 8C show an embodiment of a detection method of consecutively detecting electrons in an area including the reflected electron detection area; FIG. 8A showing a total number of electrons arriving at the detector in the reflected electron detection area of the open plug, FIG. 8B showing a total number of electrons arriving at the detector in the reflected electron detection area and the secondary electron detection area of the open plug and FIG. 8C showing a total number of electrons arriving at the detector in the area from the reflected electron detection area to the mirror electron detection area of the open plug;

FIG. 9A showing a total number of electrons arriving at the detector in the secondary electron detection area of the open plug and FIG. 9B showing a total number of electrons arriving at the detector in the secondary electron detection area and the mirror electron detection area of the open plug;

FIG. 11A showing a cross-sectional view of the wafer in which an $n^+$-p plug is formed and FIG. 11B showing a variation of a surface potential with the passage of time when an electron beam is irradiated onto the wafer;

FIG. 14A showing a total number of electrons arriving at the detector in the reflected electron detection area of the open plug, FIG. 14B showing a total number of electrons arriving at the detector in the reflected electron detection area and the secondary electron detection area of the open plug and FIG. 14C showing a total number of electrons arriving at the detector in the area from the reflected electron detection area to the mirror electron detection area of the open plug;

FIGS. 15A and 15B show an inspection method without detecting reflected electrons of the open plug; FIG. 15A showing a total number of electrons arriving at the detector in the secondary electron detection area of the open plug and FIG. 15B showing a total number of electrons arriving at the detector in the secondary electron detection area and the mirror electron detection area of the open plug;

FIG. 16 shows an embodiment in which the open plug is detected in the mirror electron detection area;

FIG. 17A showing a cross-sectional structure of a wafer in which a $p^+$-n plug is formed and FIG. 17B showing a relationship between an electron irradiation time and surface potential when an electron beam is irradiated onto the wafer;

FIG. 20A showing a total number of electrons arriving at the detector in the reflected electron detection area of the open plug, FIG. 20B showing a total number of electrons arriving at the detector in the reflected electron detection area and the secondary electron detection area of the open plug and FIG. 20C showing a total number of electrons arriving at the detector in the area from the reflected electron detection area to the mirror electron detection area of the open plug;

FIGS. 21A and 21B illustrate an embodiment detecting an open plug out of the $p^+$-n plug and open plug without using reflected electrons; FIG. 21A showing a total number of electrons arriving at the detector in the secondary electron detection area of the open plug and FIG. 21B showing a total number of electrons arriving at the detector in the secondary electron detection area and the mirror electron detection area of the open plug;

FIG. 22 illustrates an embodiment of a detection method of detecting an open plug using the mirror electron detection area;

FIG. 23A showing the surface of a wafer and FIG. 23B showing a detected image in a dark image mode;

FIG. 24A showing the surface of the wafer and FIG. 24B showing a detected image in a bright image mode;

FIGS. 25A and 25B show an example of VC-TEG wiring; FIG. 25A showing an example of normal VC-TEG and FIG. 25B showing an example of VC-TEG containing a defect;

FIG. 26A showing a normal detected image and FIG. 26B showing a detected image containing a defect;

DETAILED DESCRIPTION

Figure 1:
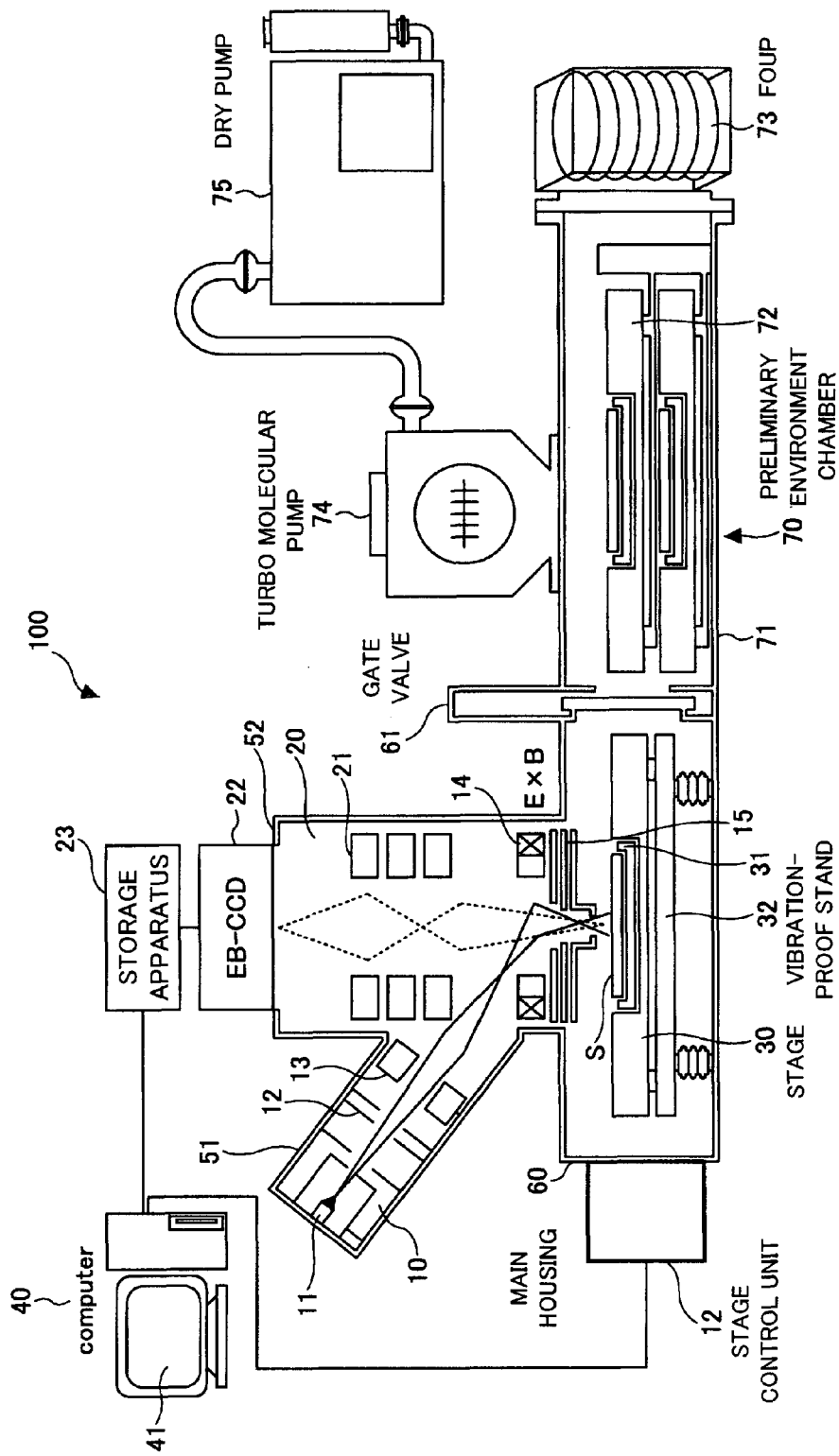
FIG. 1 shows an overall configuration of an electron beam apparatus according to an embodiment of the present invention.

The following detailed description refers to the accompanying drawings. Although the description includes exemplary implementations, other implementations are possible and changes may be made to the implementations described without departing from the spirit and scope of the invention. The following detailed description and the accompanying drawings do not limit the invention. Instead, the scope of the invention is defined by the appended claims.

"Inspection Technique"

This electron beam apparatus is provided with a stage for mounting a sample thereon, a primary optical system for generating an electron beam having a given irradiation area and irradiating the electron beam onto the sample, a secondary optical system for detecting electrons which have been generated through the irradiation of the electron beam onto the sample and have acquired structural information of the sample and for acquiring an image of the sample about a given viewing area, and an irradiation area changing or adjusting section that can change or adjust a position of the irradiation area with respect to the viewing area.

In accordance with the above-mentioned configuration, the electron beam apparatus is able to optimize a positional relationship between the irradiation area and the viewing area according to the sample.

The stage may be provided with a moving mechanism for moving the sample and the irradiation area changing section may change the position of the irradiation area to the viewing area in the moving direction of the sample (the direction in which the sample is moved). The moving direction of the sample may be equivalent to a relative moving direction of the irradiation area with respect to the sample. With such configuration, the electron beam apparatus is able to take advantage of a difference in the type of generated electrons due to a difference in the irradiation time of the electron beam.

The irradiation area changing section may change the position of the irradiation area so that the irradiation area precedes the viewing area in the moving direction of the sample. This configuration allows the primary optical system generating the electron beam to also have the function of a precharging unit. Therefore, the electron beam apparatus is able to make the charged state of the sample surface uniform without providing a precharging unit.

The irradiation area may have a greater area than that of the viewing area and the irradiation area changing section may change the position of the irradiation area so that the center of the irradiation area is aligned with the center of the viewing area. Therefore, the amount of precharging can be controlled to a smaller amount.

The sample may be a semiconductor wafer and the secondary optical system may detect a short circuit or conduction defect in the wiring in the semiconductor wafer by acquiring a voltage contrast image of the semiconductor wafer. Therefore, the electron beam apparatus can be used as the wafer defect detection apparatus that detects a wiring defect in the semiconductor wafer using the voltage contrast image.

The irradiation area changing section may change the position of the irradiation area so that the viewing area precedes the irradiation area in the moving direction of the sample. This configuration can effectively detect reflected electrons and thereby detect missing plug defects of the sample.

The sample may be a semiconductor wafer and the secondary optical system may detect a pattern defect of the semiconductor wafer by acquiring a surface image of the semiconductor wafer. This configuration preferably detect a defect of the wiring pattern in the semiconductor wafer.

An aspect of the present invention is a sample observation method of observing a sample based on an acquired image by mounting the sample on a stage, generating an electron beam having an given irradiation area to irradiate the electron beam onto the sample, acquiring an image of the sample about a given viewing area by detecting electrons which have been generated through irradiation of the electron beam and have acquired structural information of the sample, and changing or adjusting the position of the irradiation area with respect to the viewing area.

In accordance with the above-mentioned method, when observing a sample, it is possible to appropriate set the positional relationship between the irradiation area and the viewing area according to the sample.

The method of the present invention may further include a sample moving step of moving the stage to move the sample mounted thereon and the position changing step may include changing the position of the irradiation area in the moving direction of the sample (the direction in which the sample is moved). The moving direction of the sample may be a direction in which the irradiation area relatively moves with respect to the sample. In accordance with the method, the electron beam irradiation step can be employed for adjusting the amount of irradiation and dosing. The difference of generated electron type depending on the irradiation time is preferably utilized for performing an appropriate sample observation.

The position changing step may include changing the position of the irradiation area so that the irradiation area precedes the viewing area in the moving direction of the sample. Therefore, the electron beam irradiation step can provide an effect similar to that of precharging without using the precharging unit, thereby eliminating the effort required for the precharging step.

The irradiation area may have an area greater than the viewing area and the position changing step may include changing the position of the irradiation area so that the center of the irradiation area is aligned with the center of the viewing area. This method carry out the control reducing the amount of precharging.

The sample may be a semiconductor wafer, and the image acquiring step may include acquiring a voltage contrast image of the semiconductor wafer to detect a short circuit or conduction defect in the wiring in the semiconductor. Therefore, the sample observation method can be used as a wafer defect inspection method whereby a wiring defect in the semiconductor wafer is detected using the voltage contrast image.

The position changing step may include changing the position of the irradiation area so that the viewing area precedes the irradiation area in the moving direction of the sample. Therefore, the sample observation method can reliably detect reflected electrons and thereby detect a plug defect or the like using reflected electrons.

The sample may be a semiconductor wafer, and the step of acquiring an image may include acquiring a surface image of the semiconductor wafer to detect a pattern defect of the semiconductor wafer. Therefore the sample observation method can be used as a wafer pattern defect inspection method.

Hereinafter, preferred embodiments of the present invention will be explained with reference to the attached drawings.

FIG. 1 shows an overall configuration of an electron beam apparatus 100 according to this embodiment. In FIG. 1, the electron beam apparatus 100 is provided with a primary optical system 10, a stage 30 and a secondary optical system 20.

The primary optical system 10 generates a primary electron beam and irradiates the primary electron beam onto a sample S. Since the primary optical system according to this embodiment is an optical system using an electron beam, the system may also be called a "primary electron optical system." The primary optical system 10 may be provided with an electron gun 11, an aperture 12 and a primary lens system 13. The electron gun 11 generates a primary electron beam. The aperture 12 performs shaping or the like on the primary electron beam generated. The primary lens system 13 condenses the primary electron beam. These components may be provided in a vacuum container 51. As will be described more specifically later, the primary lens system 13 can adjust the irradiation direction of the primary electron beam and can thereby change the position of the irradiation area of the primary electron beam. Therefore, the primary lens system 13 functions as an irradiation area changing section of the primary electron beam. Furthermore, the primary lens system 13 can relatively move the irradiation area of the primary electron beam on the sample S. Therefore, the primary lens system 13 also functions as a moving mechanism for the primary electron beam. The irradiation area of the primary electron beam may also be called an "irradiation field."

The primary optical system 10 may be further provided with an E×B separator 14 and an objective lens system 15. The E×B separator 14 may also be called a "Wien filter." The E×B separator 14 changes the direction of the primary electron beam using an electric field and a magnetic field which are orthogonal to each other on a plane. The E×B separator 14 directs the diagonally incident primary electron beam downward in the vertical direction toward the location where the sample S is disposed. When electrons which have acquired structural information of the sample S are generated, the Lorentz force of the electric field and the magnetic field of the E×B separator 14 sends those electrons vertically upward as they are. The objective lens system 15 is a lens for performing final fine tuning of the incidence of the primary electron beam upon the sample S.

The irradiation area of the primary electron beam can be changed by adjusting the voltage application condition of the E×B separator 14. Therefore, the E×B separator 14 may also function as an irradiation area changing section as in the case of the primary lens system 13 of the primary optical system 10.

Furthermore, an electrode (not shown) may also be disposed between the objective lens system 15 and the sample S. This electrode may have a shape axially symmetric with respect to the irradiation optical axis of the primary electron beam. The voltage may be controlled by a supply voltage. With such configuration, it is possible to adjust the landing energy or the like of the electron beam incident upon the sample S.

The stage 30 is a sample base to mount the sample S. The stage 30 may be provided with a moving mechanism or driving mechanism such as a motor. The stage 30 may be an X-Y stage which is two-dimensionally movable in the X-Y direction on the horizontal plane. Furthermore, the stage 30 may be provided in a main housing 60 and further provided and supported on a vibration-proof stand 32 in the main housing 60. The main housing 60 forms a work chamber as a processing chamber that carries out an inspection or the like on the sample S. Furthermore, the vibration-proof stand 32 has the function of shutting off vibration from the floor as a vibration shutoff apparatus and prevents vibration of the bottom wall of the main housing 60 from transmitting to the stage 30.

The stage 30 may be constructed, for example, of a plurality of tables. A Y table (not shown) that moves in the Y direction may be mounted on a fixed table (not shown) and an X table (not shown) which moves in the X direction may be mounted on the Y table. A combination of such movements may allow movement in the X-Y direction. Furthermore, a rotary table (not shown) which can rotate may be provided on the X table and a holder 31 may be disposed on the rotary table. The sample S may be fixed and held on the sample mounting surface of the holder 31. The holder 31 may be configured so as to fix and hold the sample S such as a wafer using a mechanical or electrostatic chuck technique and release the sample S when an inspection or the like is finished.

The stage 30 operates, for example, the above described plurality of tables using a moving mechanism or drive section such as a servo motor, encoder and various sensors (not shown). The stage 30 may position the sample S supported on the holder 31 on the mounting surface with respect to the irradiated electron beam with high accuracy. Positioning control may be performed by a stage control unit 33. Positioning may be performed, for example, in the X direction, Y direction, Z direction and the rotation direction (θ direction) around an axis perpendicular to the supporting plane of the sample. In positioning of the Z direction, for example, a reference position of the mounting surface on the holder 31 is detected by a position measuring apparatus using a minute diameter laser. This measuring apparatus is a laser interference distance measuring apparatus using the principle of an interferometer. The detected position may be controlled by a feedback circuit (not shown) in the stage control unit 33. Furthermore, when, for example, the sample S is a semiconductor wafer, the position of a notch or orientation flat of the semiconductor wafer may be measured. The plane position and rotation position of the wafer with respect to the electron beam may be detected. The rotary table (not shown) may be rotated by a stepping motor or the like that can be controlled by a micro angle to perform position control. The signal obtained may also be normalized by entering the rotation position and/or X, Y positions of the wafer with respect to the electron beam beforehand into a signal detection system or image processing system which will be described later.

The secondary optical system 20 is a structure for obtaining an image related to the structure of the sample S. When the primary optical system 10 irradiates the electron beam onto the sample S, electrons which have acquired information on the sample structure of the sample S are generated. These electrons are detected by the secondary optical system 20 and an image related to the structure of the sample S is obtained. Here, the "electrons which have acquired information on the sample structure of the sample S" may include "electrons emitted from the sample S according to the incidence of the electron beam upon the sample S" and "electrons reflected from the sample S immediately before the incidence upon the sample S." The "electrons emitted from the sample S" are, for example, electrons reflected by elastic scattering according to the incidence of the electron beam upon the sample S. The reflected energy of these reflected electrons is substantially same as the incident energy. Furthermore, for example, the "electrons emitted from the sample S" are secondary electrons having energy smaller than that of the incident electron beam. In addition, the "electrons emitted from the sample S" may include backward scattered electrons or the like. Furthermore, "electrons reflected from the sample S immediately before incidence upon the sample S without reaching the sample S" may include mirror electrons. When, for example, the surface potential of the sample S is substantially on par with the accelerating voltage of the electron gun 11, mirror electrons can be generated. As in the case of electrons emitted from the sample S, mirror electrons can also acquire information on the structure of the sample S. Therefore, an image of the sample structure of the sample S can be obtained based on mirror electrons.

The secondary optical system 20 is provided with a secondary lens system 21 and a detector 22. The secondary lens system 21 is a lens for passing secondary electrons separated from the primary optical system 10 by the E×B separator 14. The secondary lens system 21 may be composed, for example, of an electrostatic lens. Furthermore, this lens system also functions as a magnifier that magnifies the image obtained from electrons passing through the secondary optical system 20. The detector 22 is configured to detect electrons which have passed through the secondary lens system 21 and acquire an image of the sample structure of the sample S. The detection surface of the detector 22 is suitably disposed on the image forming surface of the secondary lens system 21.

The detector 22 is a two-dimensional type detector provided with a plurality of pixels on the detection surface. The detector 22 detects electrons which have acquired the structural information on the sample S through the respective pixels and forms an image on the detection surface. The electron beam apparatus 100 of this embodiment is different from a scanning electron microscope. The scanning electron microscope detects only signal intensity of electrons detected by one pixel and combines multiple detection values to obtain an image later. In contrast, the electron beam apparatus 100 projects an image of a predetermined detection area onto a detection surface, and is therefore also called a "mapping and projection type." The detector 22 has a plurality of two-dimensional pixels and is, for example, CCD (Charge Coupled Device), TDI (Time Delay Integration)-CCD, EB-CCD or EB-TDI. The CCD and TDI-CCD detect light signals. Therefore, when the CCD and TDI-CCD are applied, the detector 22 may be provided with an MCP (Micro-channel Plate) that amplifies a quantity of electrons and a fluorescent screen that converts electrons to light. The EB-CCD and EB-TDI can directly detect electrons on the detection surface. Therefore, when the EB-CCD and EB-TDI are used, the EB-CCD and EB-TDI can be applied to the detector 22 without the further components like the CCD and TDI-CCD.

The detection area of the detector 22 is also called a "field of view." The claims, specification and drawings of the present invention refer to the detection area as a "viewing area." The viewing area of the detector 22 is determined by the arrangement and configuration of the secondary lens system 21 of the secondary optical system 20 and the arrangement of the detector 22 or the like. Therefore, when these elements are fixed, the viewing area is fixed.

The detector 22 may be provided with an image processing section (not shown) in addition to the detection unit having a detection surface. The image processing section may perform image processing on electrons detected on the detection surface of the detection unit and acquire image electron data on the sample structure of the sample S.

A storage apparatus 23 is configured to store the image electron data acquired by the image processing section of the detector 22. A normal memory or the like may be applied to the storage apparatus 23.

A computer 40 is provided with a display 41 and displays a sample structure image of the sample S stored in the storage section 23. Furthermore, the computer 40 performs an analysis of condition of the sample S based on the sample structure image and may control, for example, the stage control unit 33 according to the analysis result.

Next, components related to the electron beam apparatus 100 in FIG. 1 will be explained. The components related to the electron beam apparatus 100 include an optical microscope (not shown), a gate valve 61, a preliminary environment chamber (mini-environment chamber) 70, a pre-aligner 72, a Foup 73, a turbo molecular pump 74 and a dry pump 75.

First, the electron beam apparatus 100 may be provided with an optical microscope. The optical microscope constitutes an alignment control apparatus for positioning the sample S on the stage 30. A high magnification is set in the primary optical system and secondary optical system which are the electron optical systems explained so far. Therefore, the magnification may be too high in rough positioning of the sample S. In such a case, an optical microscope of a low magnification is provided. Rough alignment may be performed using the optical microscope first. Next, precise alignment may be performed using the electron optical system.

The gate valve 61 is disposed between the main housing 60 and the preliminary environment chamber 70 and controls communication and sealing (shielding) between both chambers. When the gate valve 61 is opened, the sample S can be transferred between the main housing 60 and the preliminary environment chamber 70. When the gate valve 61 is closed, pressure control (vacuum control) can be individually performed between the main housing 60 and the preliminary environment chamber 70.

The preliminary environment chamber 70 is provided with a housing 71, a gas circulation apparatus (not shown), an exhaust apparatus (not shown) and the pre-aligner 72. The housing 71 forms a mini-environment space. The atmosphere is controlled in the mini-environment space. The gas circulation apparatus circulates a gas such as clean air in the mini-environment space to control the atmosphere. The exhaust apparatus collects and exhausts part of the air supplied into the mini-environment space. The pre-aligner 72 is disposed in the mini-environment space. The pre-aligner 72 roughly positions and the sample S such as a substrate and a wafer to be inspected. A sensor may be provided in the mini-environment space to observe the degree of cleanness. The preliminary environment chamber 70 may be shut down when the degree of cleanness degrades.

When, for example, the sample S is a wafer, the pre-aligner 72 detects an orientation flat or notch formed in the wafer using the optical configuration or mechanical configuration. The notch is a single or a plurality of V-shaped notches formed in the perimeter of the wafer. The pre-aligner 72 may also predetermine the position of the wafer in the rotation direction around the axis with the accuracy of approximately ±1 degree. Thus, the pre-aligner 72 performs rough positioning of the inspection target.

The Foup 73 is a cassette holder that holds a plurality of cassettes (not shown). In each cassette, a plurality of (e.g., approximately 25) samples S such as wafers are accommodated arranged in parallel in the vertical direction. When the target sample S is a semiconductor wafer, wafers to be inspected are accommodated in the cassette. Inspections are performed after the process of processing wafers or during the process in the semiconductor manufacturing step. More specifically, wafers accommodated in a cassette may be wafers processed, for example, in a film forming step, CMP (Chemical Mechanical Polishing) step, ion injection step or the like. Furthermore, a wiring pattern may be already formed on the surfaces of wafers or wiring pattern may not be formed yet.

A turbo molecular pump 74 and a dry pump 75 are vacuum pumps for evacuating the preliminary environment chamber 70. The dry pump 75 first operates in an atmosphere and a low vacuum area. When a certain degree of vacuum is obtained, the turbo molecular pump 74 also operates. This further increases the degree of vacuum and achieves a high vacuum condition. Therefore, the inside of the preliminary environment chamber 70 can be maintained under vacuum.

No vacuum pump is shown in the primary optical system of the electron beam apparatus 100. Another vacuum pump may be provided to maintain the primary optical system 10, main housing 60 and secondary optical system 20 under vacuum. Furthermore, the turbo molecular pump 74 and dry pump 75 may also be used to evacuate the electron beam apparatus 100.

Figure 2A:
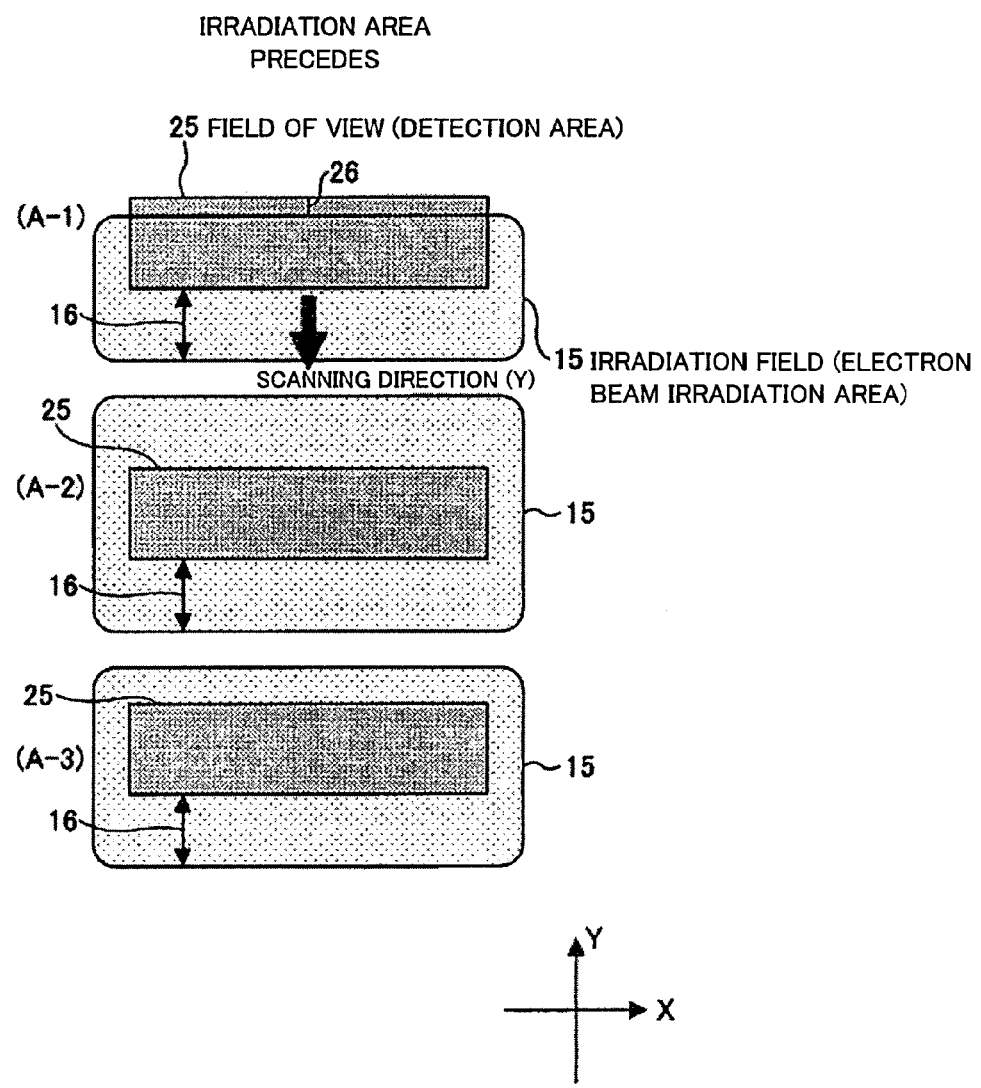
Figure 2C:
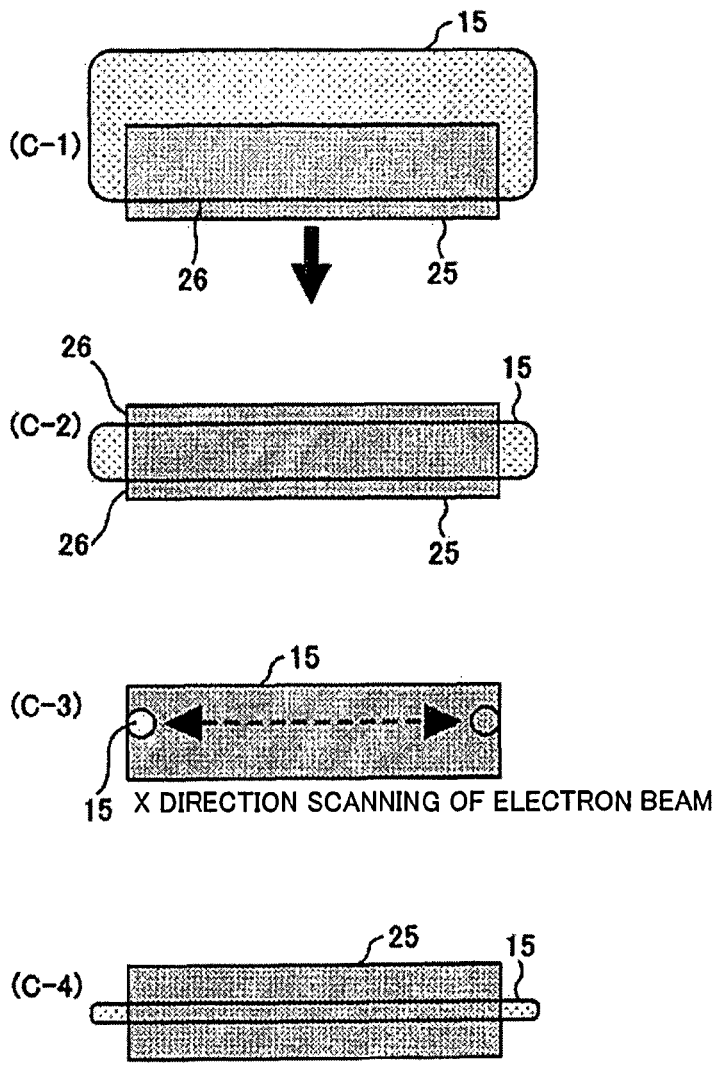

Next, referring to FIG. 2A to FIG. 2C, various embodiments will be explained in which the position of the irradiation area of an electron beam is changed with respect to the viewing area in the electron beam apparatus 100. FIG. 2A to FIG. 2C show a positional relationship between an irradiation area 15 of the primary electron beam and a viewing area 25 of the secondary optical system 20.

FIG. 2A shows an embodiment in which the irradiation area precedes the viewing area. According to Embodiment (A-1) in FIG. 2A, the position of the irradiation area 15 of the electron beam is moving in the downward direction (−Y direction) with respect to the viewing area 25. In Embodiment (A-1), the sample S moves in the upward direction (+Y direction). Relatively, the irradiation area 15 and viewing area 25 of the electron beam move in the downward direction (−Y direction) of the sample S. Hereinafter, in all embodiments shown in FIG. 2A to FIG. 2C, the sample S moves in the +Y direction and the electron beam moves on the sample S relatively in the −Y direction.

In Embodiment (A-1), in the "moving direction sample S (±Y direction or vertical direction: relative moving direction of the sample and irradiation area, the same applies hereinafter)," the irradiation area 15 precedes the viewing area 25 by the length of the precharging area 16. In this condition, the irradiation area 15 does not cover part of the upper area of the viewing area 25. That is, there exists a non-irradiation area 26 which is not irradiated with the irradiation area 15. Here, the irradiation area 15 has a standard size and the position of the irradiation area 15 is moved in the −Y direction. This change in the irradiation position produces the non-irradiation area 26. The irradiation area 15 and the viewing area 25 move relative to the sample S while keeping this state.

According to such a positional relationship between the irradiation area 15 and the viewing area 25, the irradiation area 15 always precedes the viewing area 25 by the length of the precharging area 16 with respect to the moving direction of the sample S. Therefore, a precharging effect is obtained. That is, this embodiment can achieve an effect similar to that when precharging is performed on the sample S in the precharging area 16 before inspecting the viewing area 25, and can thereby make surface charge of the sample S uniform. Furthermore, in the state of (A-1), electrons which have acquired structural information on the sample S are not generated from the non-irradiation area 26. Therefore, no structural information on the sample S is obtained from the non-irradiation area 26. However, when the sample S moves in the +Y direction, the non-irradiation area 26 moves into the irradiation area 15. Therefore, with a series of inspection operations, the structural information on the non-irradiation area 26 is also obtained immediately after, and so there is no problem.

The position of the irradiation area 15 may be changed by adjusting the irradiation direction of the primary electron beam. The primary lens system 13 of the primary optical system 10 can adjust the irradiation direction of the primary electron beam. That is, the primary lens system 13 may function as the irradiation area changing section. Furthermore, the position of the irradiation area 15 may also be changed by changing the voltage application condition of the E×B separator 14. That is, the E×B separator 14 may function as the irradiation area changing section. Furthermore, the width of the precharging area 16 can be controlled by these irradiation area changing sections. The precharging area 16 is determined by considering the current density of the primary electron beam and moving speed of the sample S or the like in a comprehensive manner. This makes it possible to easily realize precise control on the amount of precharging.

As explained above, Embodiment (A-1) moves the irradiation area 15 so as to precede the viewing area 25. This makes it possible to obtain an effect similar to a precharging effect using only the primary electron beam without providing a precharging unit. Moreover, the amount of dosing required for precharging can also be precisely controlled by controlling the precharging area 16.

In Embodiment (A-2), the irradiation area 15 is aligned with the center of the viewing area 25. The area of the irradiation area 15 is expanded compared to (A-1). The entire viewing area 25 is covered with the irradiation area 15. A precharging area 16 is provided so as to precede in the moving direction of the sample S. This precharging area 16 realizes the function of precharging with respect to the viewing area 25 as in the case of Embodiment (A-1).

According to Embodiment (A-2), non-irradiation area 26 is not produced in the viewing area 25. It is possible to generate electrons which have uniformly acquired information on the sample structure from the entire viewing area 25. Therefore, a uniform image with reduced image irregularities can be obtained.

In Embodiment (A-3), a magnification of the irradiation area 15 is set to be lower than that in Embodiment (A-2). Furthermore, the center of the irradiation area 15 precedes the center of the viewing area 25. The entire viewing area 25 is covered with the irradiation area 15.

Embodiment (A-3) can maximize the precharging area 16 while the irradiation area 15 can cover the entire viewing area 25. That is, it is possible to reduce image irregularities of the acquired image of the secondary optical system 20 while expanding the precharging area 16 to a maximum extent. Therefore, a maximum precharging effect can be obtained with the limited irradiation area 15.

Next, an embodiment in FIG. 2B will be explained. FIG. 2B shows a relationship between the irradiation area 15 and viewing area 25 in a case where only a small amount of precharging is required.

In Embodiment (B-1), the center of the viewing area 25 is aligned with the center of the irradiation area 15. Furthermore, the precharging area 16 is not so large. The irradiation area 15 covers the viewing area 25. When not too a large amount of precharging is required, Embodiment (B-1) may be applied.

In Embodiment (B-1), the viewing area 25 and irradiation area 15 are set in similar size and the precharging area 16 is small. This makes it possible to efficiently achieve only a necessary amount of precharging without consuming energy uselessly.

Next, an embodiment in FIG. 2C will be explained. In FIG. 2C, the viewing area 25 precedes the irradiation area 15 in the moving direction of the sample S.

In Embodiment (C-1), the irradiation area 15 has a standard size (area). The position of the irradiation area 15 is changed so as to move in the upward (+Y) direction. Therefore, the viewing area 25 precedes and the irradiation area 15 is delayed with respect to the moving direction of the sample S.

As will be described in detail later, reflected electrons are emitted from the sample S through elastic scattering for a certain period after an electron beam is irradiated. When the structure of the sample S should be inspected by effectively using reflected electrons, Embodiment (C-1) is suitable. In Embodiment (C-1), the non-irradiation area 26 is also generated in the viewing area 25. However, when the stage 30 moves the sample S, an electron beam is sequentially irradiated onto the non-irradiation area 26. Therefore, there is no problem in acquiring an image of the sample structure.

In Embodiment (C-2), the center of the viewing area 25 is aligned with the center of the irradiation area 15. However, compared to Embodiment (C-1), the irradiation area 15 is reduced. The width of the viewing area 25 is set to be larger than the width of the irradiation area 15 in the moving direction (±Y direction) of the sample S.

In Embodiment (C-2), no useless primary electron beam is irradiated onto the sample S. Reflected electrons can be efficiently used with small energy.

In Embodiment (C-3), an electron beam is irradiated by scanning with a dotted spot beam in the X direction. That is, the viewing area 25 is scanned in a direction perpendicular to the moving direction of the sample S. This configuration can also generate reflected electrons from the sample S. It is possible to perform an inspection or the like using reflected electrons.

In Embodiment (C-4), part of the viewing area 25 is irradiated using a linear beam. The linear beam is a narrow beam having a width corresponding to one pixel in the Y direction. (C-4) is an intermediate embodiment between (C-2) and (C-3). Embodiment (C-3) performs scanning in the X direction with a spot beam. Therefore, a time lag is generated in the X direction. (C-4) can generate reflected electrons using a minimum irradiation area 15 while removing such a time lag.

Figure 3A:
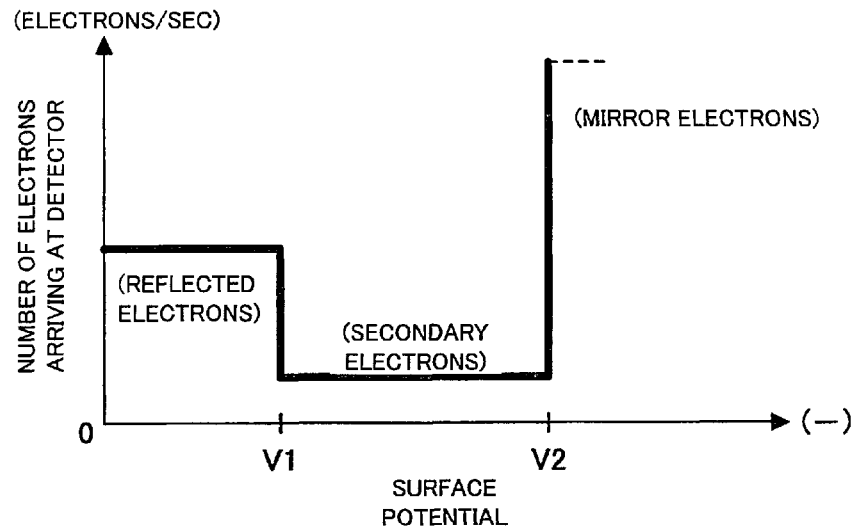
FIGS. 3A and 3B show a quantity of electrons arriving at a detector and types of electron with the passage of time.
Figure 3B:
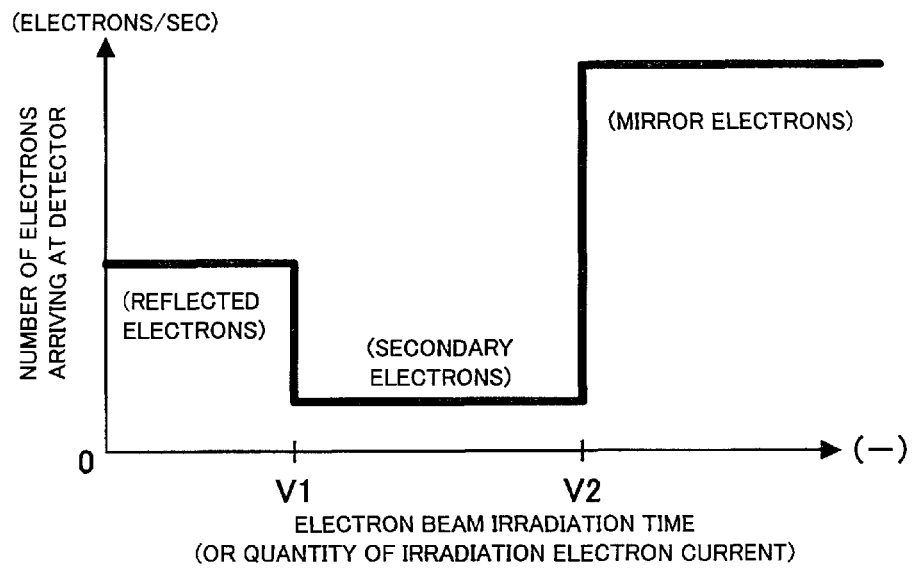

Next, FIG. 3A and FIG. 3B illustrate a phenomenon of variations in the quantity of electrons (number of electrons, and the same applies hereinafter) and the type of electrons accepted by the detector 22 of the secondary optical system 20 according to the amount of precharging of the wafer. The inventor of the present application found this phenomenon and proposes the electron beam apparatus 100 according to the present invention using this phenomenon and a sample observation method using this.

FIG. 3A and FIG. 3B show the quantity of electrons arriving at the detector 22 according to the lapse of time and the type of those electrons. FIG. 3A shows a relationship between the surface potential of the sample S and the number of electrons arriving at the detector 22 per unit time. The horizontal axis shows the surface potential of the sample S and the vertical axis shows the number of electrons arriving at the detector 22 per unit time (seconds).

In FIG. 3A, a low landing energy area to the order of 20 eV corresponds to an initial stage of precharging, where reflected electrons are detected. The amount of these reflected electrons is smaller than irradiated electrons. Therefore, the irradiation area 15 of the electron beam is negatively charged with a lapse of time.

As the negative charge advances, the surface potential of the irradiation area increases toward the negative side. The effective landing energy of incident electrons of the electron beam decreases with respect to the potential of the irradiation area. Therefore, incident electrons are hardly reflected. In this stage, secondary electrons are generated and emitted from the wafer. When the effective landing energy of incident electrons of the electron beam is larger than the potential energy of the surface, landing of electrons continues hereafter, too. Finally, the potential energy of the wafer surface becomes equal to the landing energy of electrons. Incident electrons do not enter the irradiation area 15 and are reflected from the wafer without contacting the wafer surface immediately before the wafer surface. These electrons are called "mirror electrons."

In FIG. 3A, when mirror electrons are generated, no more electrons are entered, and therefore the surface potential of the wafer becomes constant. Therefore, the number of electrons arriving at the detector 22 per unit time also becomes constant.

In FIG. 3A, when the potential of the wafer surface is fixed, if the surface potential energy is smaller than the landing energy of incident electrons, reflected electrons are always generated. Therefore, when, for example, there is a grounding or earth electrode on the wafer surface, reflected electrons are always emitted from the grounding part.

FIG. 3B shows a relationship between a time of electron beam irradiation onto the sample S and the number of electrons arriving at the detector 22 per unit time. The horizontal axis shows the electron beam irradiation time and the vertical axis shows the number of electrons arriving at the detector 22 per unit time (seconds). While the horizontal axis in FIG. 3A shows the surface potential, the horizontal axis in FIG. 3B shows an electron beam irradiation time. FIG. 3A differs from FIG. 3B in this point.

In FIG. 3B, as the electron beam irradiation time elapses and precharging advances, the amount of dosing on the wafer surface increases. First, reflected electrons are generated from the wafer and secondary electrons are then generated and mirror electrons are finally generated. Furthermore, in the area where mirror electrons are generated, even when the electron beam irradiation time increases, the number of electrons arriving at the detector 22 per unit time is constant.

Figure 4:
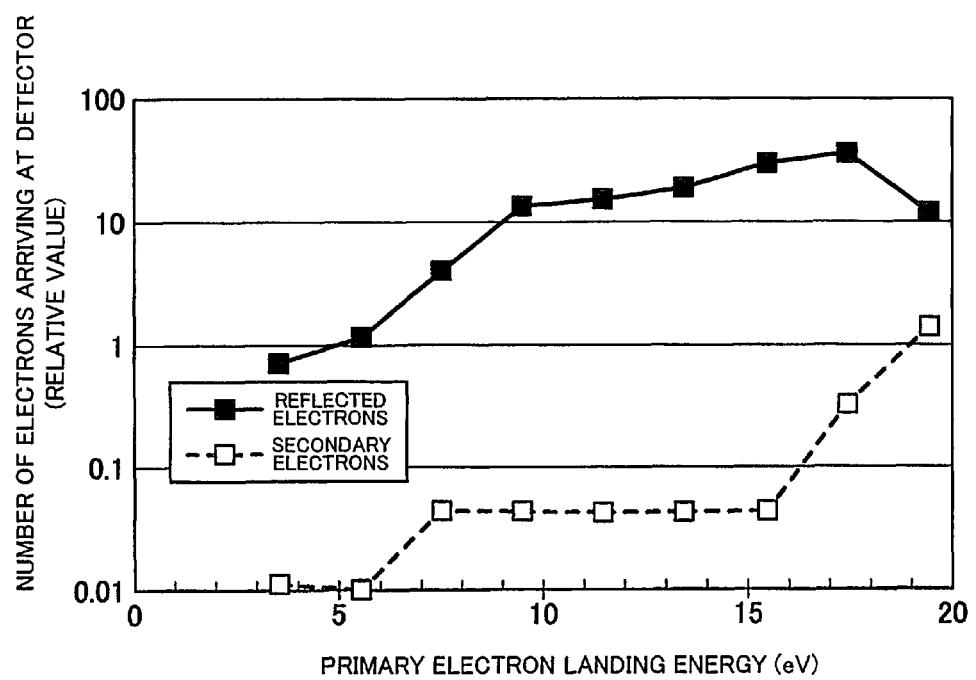
FIG. 4 shows a relationship between the number of electrons arriving at the detector from a wafer and landing energy.

FIG. 4 shows a relationship between the number of electrons which have been generated from the tungsten area of the wafer and which have arrived at the detector 22 and landing energy of primary electrons. In FIG. 4, the horizontal axis shows primary electron landing energy (eV) and the vertical axis shows the number of electrons arriving at the detector.

As is apparent from a comparison between the curve of reflected electrons and the curve of secondary electrons in the graph of FIG. 4, the number of reflected electrons is overwhelmingly greater than the number of secondary electrons in the low landing energy area to the order of approximately 20 eV. This phenomenon is considered to be attributable to a difference in electron transmissivity from the wafer to the detector 22. In the mapping and projection type electron beam apparatus 100 according to this embodiment, the difference in electron transmissivity is produced according to the difference in distribution of directions in which respective electrons are emitted. This difference is considered to produce the above described phenomenon. Here, the "electron transmissivity" refers to a ratio of "electrons capable of passing through the secondary optical system 20 and arriving at the detector 22" to "electrons generated from the wafer."

The secondary electrons have a distribution of emission directions called a "cosine law." Secondary electrons are not emitted in the vertical direction from the surface of the wafer. Secondary electrons have an emission distribution in a diagonal direction having a certain angle with respect to the vertical axis. Therefore, in the mapping and projection type electron beam apparatus adopted in the electron beam apparatus 100 according to this embodiment, the electron transmissivity of secondary electrons is not so large.

On the other hand, reflected electrons are emitted from the wafer all together in a direction relatively turned by 180 degrees from the direction of incidence of primary electrons. Therefore, electron transmissivity of reflected electrons is considered to increase in the mapping projection type electron beam apparatus 100 of this embodiment. The number of reflected electrons arriving at the detector 22 is considered to increase by order of magnitude compared to the number of secondary electrons.

As described above, when reflected electrons are used for an inspection compared to the conventional case where secondary electrons are used, the number of electrons arriving at the detector 22 increases significantly. Therefore, it is possible to drastically reduce the number of primary electrons necessary to obtain equivalent signal intensity using the detector 22. It is thereby possible to reduce charging of the wafer and realize inspections with less damage.

The relationship in FIG. 4 (relationship between the type of electron and the number of electrons arriving at the detector in the low landing energy area) corresponds to those in FIG. 3A and FIG. 3B.

Returning to FIG. 3A and FIG. 3B, attention is focused on the number of electrons arriving at the detector 22 when a primary electron beam is irradiated onto the wafer. The number of electrons is constant in the initial state (first state). Next, when the wafer surface reaches a certain predetermined potential V1, the number of electrons (amount of electrons) decreases (second state). Furthermore, when charging up of the wafer is continued, the number of electrons (amount of electrons) drastically increases at a certain predetermined potential V2 (third state). In the first state, reflected electrons arrive at the detector. In the second state, secondary electrons arrive at the detector 22. Furthermore, in the third state, since the amount of charge of the wafer increases, the primary electron beam cannot reach the wafer surface and is reflected immediately before the wafer surface. This is a state of so-called mirror electrons. For example, the amount of dosing in the first state may be 0 to 1 ($\mu C/cm^2$). The amount of dosing in the second state may be 0.5 to 5 ($\mu C/cm^2$). The amount of dosing in the third state may be 3 to 10 ($\mu C/cm^2$).

As the precondition for occurrence of the state variation explained in FIG. 3A and FIG. 3B, the irradiation part of the electron beam needs to be charged up. However, the part where the potential is fixed (e.g., grounding part), is not charged up. On the other hand, charging up is produced in the part in a floating state (e.g., open defect part of wiring). If the surface potential energy is smaller than the landing energy of incident electrons, reflected electrons are always generated. Using this phenomenon makes it possible to detect an open defect or short-circuit defect of the wiring formed in the wafer. That is, defects can be detected using voltage contrast.

Next, various examples will be explained where defects of the wafer are detected using the electron beam apparatus 100 of this embodiment.

First Inspection Example

In a first inspection example, an open defect will be detected in a wafer in which a grounding plug is formed.

Figure 5A:
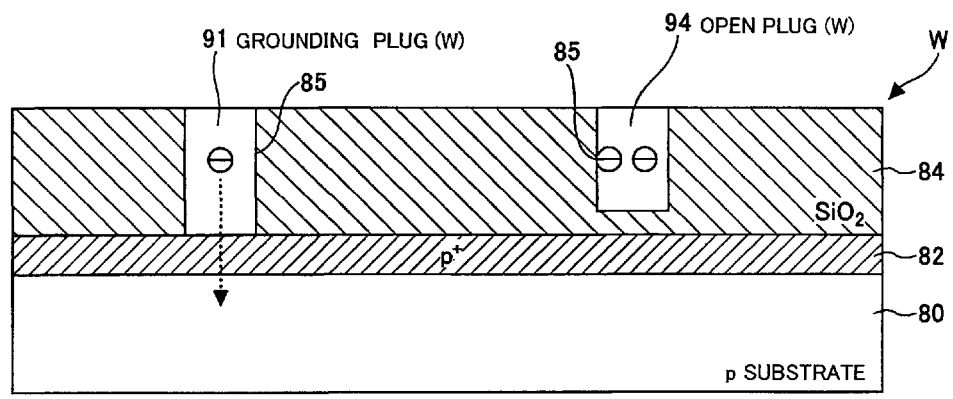
FIGS. 5A and 5B illustrate defect detection according to a first inspection example.
Figure 5B:
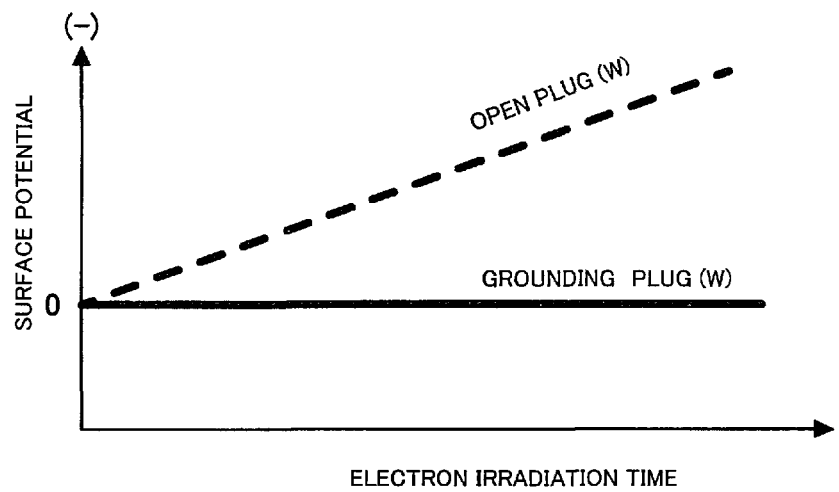

FIG. 5A and FIG. 5B illustrate detection of defects according to the first inspection example. FIG. 5A is a cross-sectional view of a wafer W in which a grounding plug 91 and an open plug 94 are formed.

In the wafer W in FIG. 5A, a p-type silicon substrate 80 is a supporting substrate, a p+ high concentration impurity area 82 is stacked thereon and an $SiO_2$ oxide film layer 84 is further formed thereon. The grounding plug 91 is provided in a groove 85 in the oxide film layer 84. The grounding plug 91 is connected to a conductive type p+ high concentration impurity area 82. The grounding plug 91 may be made, for example, of tungsten. Since the grounding plug 91 is connected to the conductive type p+ high concentration impurity area 81, the potential of the grounding plug 91 is the same as the potential of the p-type silicon substrate 80. On the other hand, the open plug 94 which is a defective plug is not connected to the conductive type p+ high concentration impurity area 82 and is in a floating state.

FIG. 5B shows a variation in the surface potential of the wafer W when a primary electron beam having low landing energy is irradiated onto the wafer W in FIG. 5A. In FIG. 5B, the potential of the grounding plug 91 does not change even when the electron irradiation time increases. However, since electrons are accumulated in the open plug 94, the potential of the open plug 94 increases toward the negative side according to the lapse of time.

Figure 6:
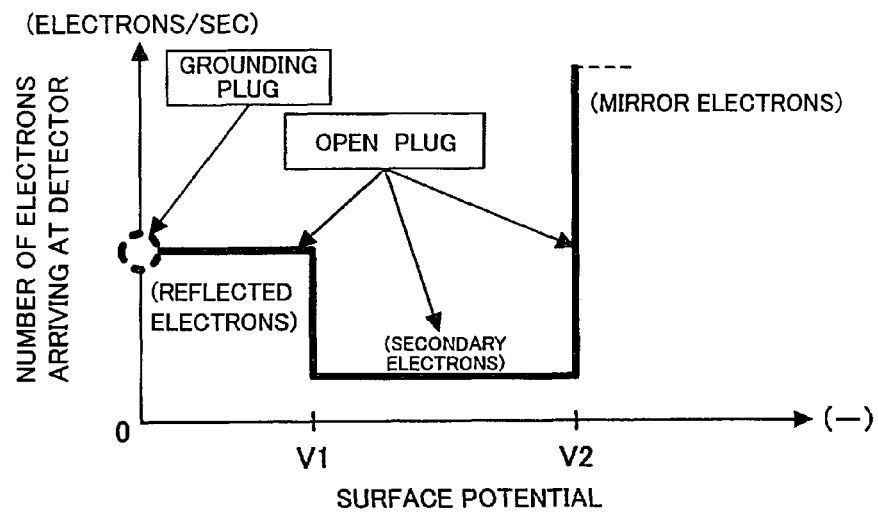
FIG. 6 shows dependency on surface potential of the number of electrons emitted from the grounding plug and open plug of the wafer shown in FIG. 5A and arriving at the detector.

FIG. 6 shows dependency of surface potential (surface potential dependency) of the number of electrons arriving at the detector 22. When a primary electron beam is irradiated onto the wafer W shown in FIG. 5A, electrons are emitted from the grounding plug 91 and open plug 94 and the number of electrons has the dependency on surface potential shown in FIG. 6.

In FIG. 6, the potential of the grounding plug 91 is fixed to the grounding potential, therefore, reflected electrons are always detected from the grounding plug 91. On the other hand, at the open plug 94, negative charge progresses with the passage of time and the surface potential increases toward the negative side. Therefore, while reflected electrons are detected in the beginning, secondary electrons are then detected and mirror electrons are finally detected. According to an experiment, by selecting an appropriate value for the landing energy of the primary electron beam, the amount of mirror electrons detected is greater than the amount of reflected electrons detected as shown in FIG. 6. In the application example of the present invention, such appropriate energy is selected as the landing energy of the primary electron beam.

Figure 7:
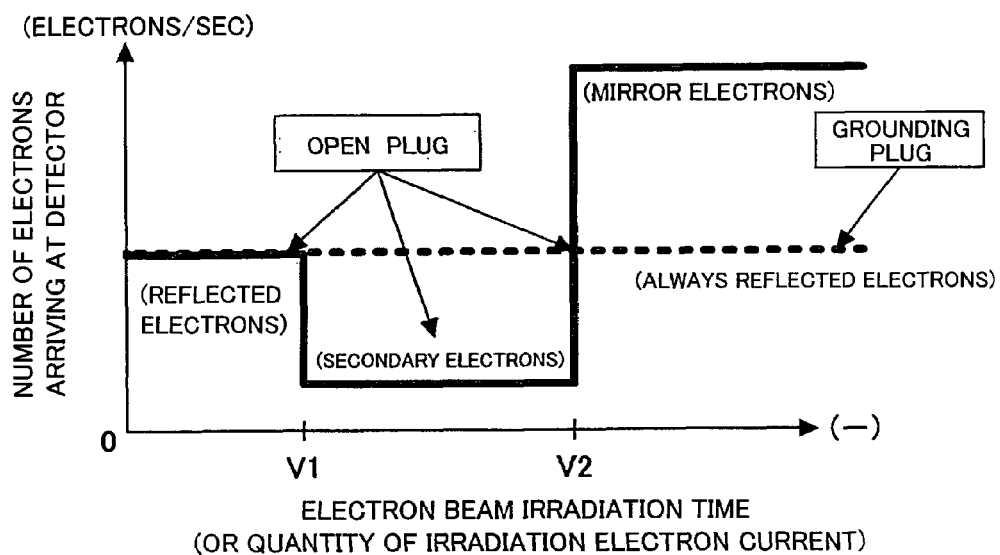
FIG. 7 shows a relationship between an electron beam irradiation time and the number of electrons arriving at the detector per unit time.

FIG. 7 shows the same data as that in FIG. 6. However, the horizontal axis is changed to an electron beam irradiation time. The vertical axis shows the number of electrons arriving at the detector 22 per unit time (seconds).

In FIG. 7, reflected electrons are always detected from the grounding plug 91. However, as for the open plug 94, the type of electrons detected varies with time and the number of electrons arriving at the detector also varies. In this example the wafer W is inspected with attention focused on the difference in the number of electrons arriving at the detector with time.

Next, referring to FIG. 8A to FIG. 8C a method of detecting the open plug in the first inspection example will be explained. According to the detection method in FIG. 8A to FIG. 8C, reflected electrons are detected first in the secondary optical system 20, and electrons are detected continuously.

FIG. 8A shows a method of using the reflected electron detection area of the open plug 94. FIG. 8A compares the total number of electrons of the open plug 94 with the total number of electrons of the grounding plug 91, where each number is a total number of electrons arriving at the detector 22 after being emitted from each plug. In the reflected electron detection area, reflected electrons are emitted from both the open plug 94 and grounding plug 91. Therefore, there is no difference in the total number of electrons arriving at the detector. Since no difference appears in the acquired images between the open plug 94 and grounding plug 91, the reflected electron detection area cannot be used for inspections.

FIG. 8B shows a method of using the area from the reflected electron detection area to the secondary electron detection area of the open plug 94. FIG. 8B compares the total number of electrons of the open plug 94 with the total number of electrons of the grounding plug 91, where each number is a total number of electrons arriving at the detector 22 after being emitted from each plug. In this case, reflected electrons continue to be emitted from the grounding plug 91. On the other hand, at the open plug 94, when the surface potential passes through the reflected electron emission area (detection area) and enters the secondary electron emission area (detection area), the number of electrons arriving at the detector drastically decreases as explained in FIG. 7. Therefore, as shown in FIG. 8B, the total number of electrons arriving at the detector of the open plug 94 is smaller than that of the grounding plug 91 and there will be a marked difference therebetween. Therefore, a difference between bright and dark is produced in the acquired image of the wafer W acquired by the secondary optical system 20. Since an electrical difference can be detected, the open plug 94 can be detected. Therefore, the embodiment in FIG. 8B can be used for an inspection of the open plug 94.

In order to realize the inspection shown in FIG. 8B, detection should be started when reflected electrons are first generated by the initial electron beam irradiation. Therefore, the field of view preceding type embodiment shown in FIG. 2C is suitably applied. The position of the irradiation area 15 is changed backward (+Y direction in FIG. 2C) so that the viewing area 25 precedes the irradiation area 15 of the electron beam with respect to the moving direction of the wafer W. Therefore, all electrons are detected by the secondary optical system 20 from the start of irradiation in the irradiation area 15 of the electron beam. Therefore, the open plug 94 can be detected in a stage in which the open plug 94 enters the area where secondary electrons are emitted.

FIG. 8C shows a method of using the area from the reflected electron detection area to the mirror electron detection area of the open plug 94. FIG. 8C compares the total number of electrons of the open plug 94 with that number of the grounding plug 91, where each number is a total number of electrons arriving at the detector 22 after being emitted from each plug. As shown in FIG. 8C, in the mirror electron area, the amount of mirror electrons generated is greater than the amount of reflected electrons generated. The number of electrons generated from the open plug 94 starts to catch up with the number of electrons generated from the grounding plug 91. As for the relationship between the total number of electrons of the open plug 94 and that of the grounding plug 91, various cases may be considered with passage of time and the state is uncertain. Therefore, the difference in the number of electrons between both plugs is unclear. Therefore, the inspection in FIG. 8C is not suitable for detection of the open plug 94.

As has been explained in FIG. 8A to FIG. 8C, only the embodiment in FIG. 8B is suitable for detection of the open plug 94. Therefore, in order to detect the open plug 94 using reflected electrons, an image of the wafer is acquired in a stage in which the open plug 94 is in the secondary electron detection area and the difference between the grounding plug 91 and open plug 94 is detected and thereby the open plug 94 can be detected. In this case, the position of the irradiation area 15 is changed so that the viewing area 25 precedes the irradiation area 15 as mentioned above.

Figure 9A:
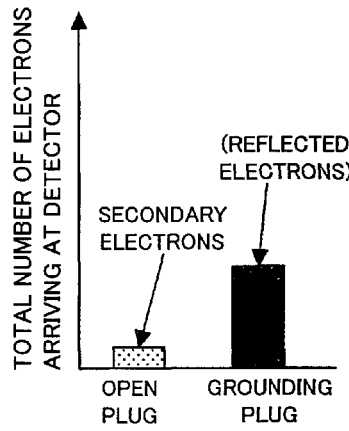
FIGS. 9A and 9B show an embodiment in which the open plug is detected without detecting reflected electrons from the open plug.
Figure 9B:
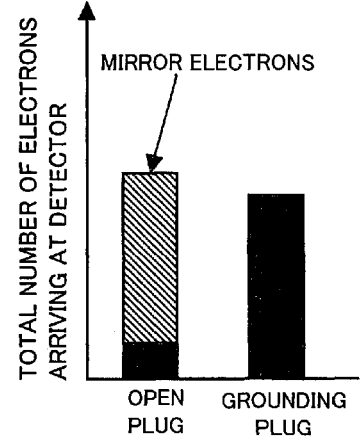

FIG. 9A and FIG. 9B show an embodiment that detects secondary electrons and mirror electrons without detecting reflected electrons from the open plug 94. Here, the open plug 94 is detected based on the detection result of secondary electrons and mirror electrons.

FIG. 9A shows the total number of electrons (total number of electrons arriving at the detector) from the open plug 94 and grounding plug 91 in the secondary electron detection area of the open plug 94 in FIG. 7. In FIG. 9A, only secondary electrons are detected from the open plug 94 and only reflected electrons are detected from the grounding plug 91. There is a large difference in the total quantity of electrons between both plugs. Therefore, the difference between the grounding plug 91 and open plug 94 can be detected from the acquired image with high contrast. The embodiment in FIG. 9A is preferable to detect the electrical difference.

Therefore, in order to realize the above-mentioned inspection method of detecting secondary electrons without detecting reflected electrons, the embodiments in FIG. 2A and FIG. 2B are appropriate. That is, an inspection is performed in the positional relationship that the irradiation area 15 precedes the viewing area 25 with respect to the movement of the wafer W. This causes reflected electrons to be emitted from the open plug 94 in the precharging area 16. Only secondary electrons are then detected in the viewing area 25. With such a setting, the inspection method in FIG. 9A can be suitably realized.

FIG. 9B compares the total number of electrons of the open plug 94 (total number of electrons arriving at the detector) and that of the grounding plug 91 in the secondary electrons detection area and mirror electron detection area of the open plug 94.

In FIG. 9B, only reflected electrons are detected from the grounding plug 91. On the other hand, both secondary electrons and mirror electrons are detected from the open plug 94. As explained in FIG. 7, when the quantity of reflected electrons is compared with that of secondary electrons, the quantity of reflected electrons generated is larger. On the other hand, when the quantity of reflected electrons is compared with that of mirror electrons, the quantity of mirror electrons is larger. The number of electrons detected from the open plug 94 catches up with and passes the number of electrons detected from the grounding plug 91 with a lapse of time. Therefore, the difference in the number of electrons between both plugs is an uncertain value that changes with time. Therefore, the inspection method in FIG. 9B is not suitable for detection of the open plug 94.

However, even in the embodiment in FIG. 9B, the number of electrons from the open plug 94 is definitely smaller than the number of electrons from the grounding plug 91 in an initial stage in which mirror electrons start to be generated from the open plug 94. The image of the open plug 94 is dark. Therefore, both plugs can be distinguished. Moreover, in reverse, when a time elapses until a large quantity of mirror electrons are generated from the open plug 94, the number of electrons detected from the open plug 94 becomes greater than the number of electrons detected from the grounding plug 91. The image acquired from the open plug 94 becomes brighter. Therefore, if the electron beam irradiation time (amount of dosing) can be appropriately controlled, a bright/dark difference is produced between the images acquired from the open plug 94 and grounding plug 91 even in the embodiment in FIG. 9B. It is possible to detect electrical differences and distinguish between both plugs. However, this method requires precise control over the electron beam irradiation time or the amount of dosing. Therefore, the embodiment in FIG. 9A is more suitable for open plug detection than the embodiment in FIG. 9B.

Figure 10:
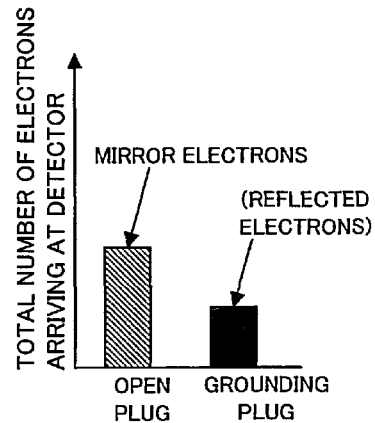
FIG. 10 shows a total number of electrons arriving at the detector in the mirror electron detection area.

FIG. 10 compares the total number of electrons (total number of electrons arriving at the detector) of the open plug 94 and that of the grounding plug 91 in the area where mirror electrons of the open plug 94 are generated (detection area).

In FIG. 10, only mirror electrons are detected from the open plug 94 and only reflected electrons are detected from the grounding plug 91. As has been explained with reference to FIG. 7, the quantity of mirror electrons generated is greater than the quantity of reflected electrons generated. That is, the number of mirror electrons generated from the open plug 94 is definitely greater than the number of reflected electrons emitted from the grounding plug 91. Therefore, the acquired image of the open plug 94 is brighter than the acquired image of the grounding plug 91. Both plugs can be distinguished using the light/dark difference.

In order to execute the inspection method according to FIG. 10, the relationship between the irradiation area 15 and the viewing area 25 in FIG. 2A and FIG. 2B are suitably used. This causes the irradiation area to be changed so that the irradiation area 15 precedes the viewing area 25 in the moving direction of the wafer W. In the precharging area 16 in FIG. 2A and FIG. 2B, reflected electrons and secondary electrons of the open plug 94 are emitted. In the viewing area 25, only mirror electrons are detected. In order to emit only reflected electrons and secondary electrons in the precharging area 16, the precharging area for inspection in FIG. 10 is preferably greater than the precharging area for inspection in FIG. 9A. Especially the embodiment in (A-1) or (A-3) in FIG. 2A may be suitably applicable.

As has been explained so far, in the first inspection example, open plug 94 is suitably detected by the inspection methods in FIG. 8B, FIG. 9A and FIG. 10. These inspections use voltage contrast of wafer surface potentials, and can thereby distinguish the open plug 94 from the grounding plug 91. By changing the position of the irradiation area 15 of the primary electron beam with respect to the viewing area 25, it is possible to easily implement an embodiment suitable for various inspections. For example, the field of view preceding type embodiment in FIG. 2C may be applied to the inspection in FIG. 8B. The irradiation area preceding type embodiment in FIG. 2A and FIG. 2B may be applied to the inspection in FIG. 9A. The irradiation area preceding type embodiments in FIG. 2A and FIG. 2B may also be applied to the inspection in FIG. 10. Especially Embodiment (A-1) or (A-3) having a greater precharging area is suitably applicable.

On the other hand, the difference in image brightness between the defective part and normal part resulting from the inspections in FIG. 8A, FIG. 8C and FIG. 9B is small. These inspections are suitable for observing defects on a pattern surface. Instead of detecting specific defects, an image of the surface pattern of the wafer is acquired there. Pattern errors are discovered by observing this image and, therefore, an overall pattern defect inspection can be performed. When performing these inspections, the position of the electron beam irradiation area 15 with respect to the viewing area 25 is also appropriately changed. For example, the viewing area preceding type embodiment in FIG. 2C is suitably applicable to inspections in FIG. 8A and FIG. 8C. The irradiation area preceding type embodiments in FIG. 2A and FIG. 2B are suitably applicable to an inspection in FIG. 9B.

As explained above, the various inspections shown in the first inspection example can be performed by making various changes to the position of the electron beam irradiation area 15 with respect to the viewing area 25 in the electron beam apparatus 100 according to this embodiment shown in FIG. 1.

Second Inspection Example

Next, in the second inspection example, an open defect is detected in the wafer W in which an $n^+$-p plug is formed.

Figure 11A:
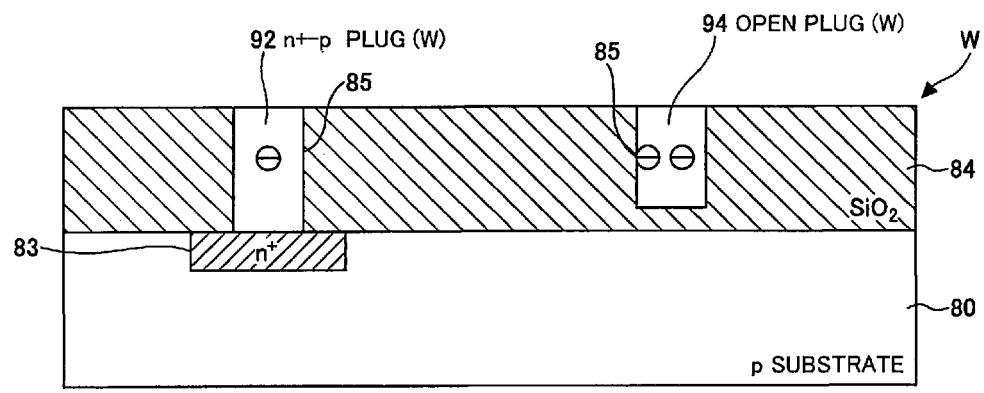
FIGS. 11A and 11B illustrate a second inspection example carrying out an open defect inspection method for a wafer in which an $n^+$-p plug is formed.
Figure 11B:
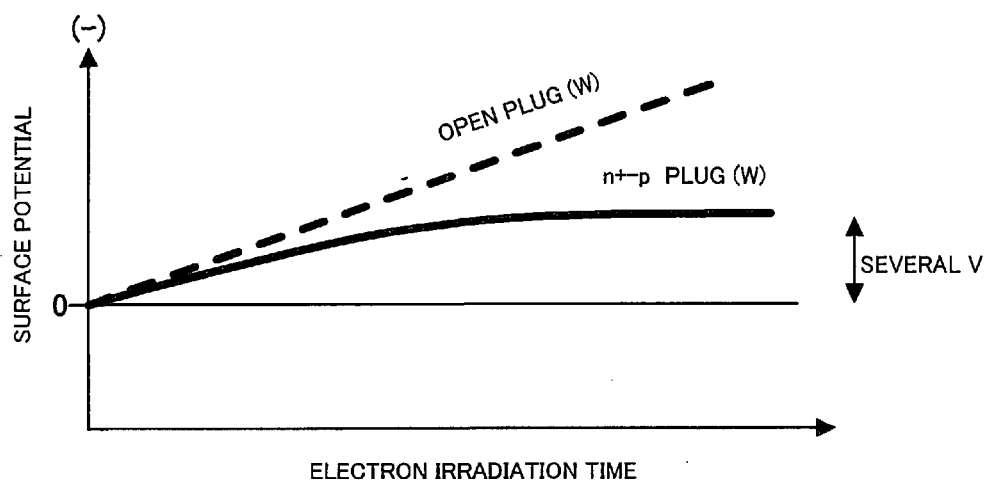

FIG. 11A and FIG. 11B show an inspection method of detecting an open defect in the wafer W in which an $n^+$-p plug is formed.

FIG. 11A is a cross-sectional view of the wafer W in which an $n^+$-p plug 92 is formed. In FIG. 11A, an opposite conductive type $n^+$ high concentration impurity area 83 is provided on the surface of a p-type silicon substrate 80. An SiO$_2$ oxide film layer 84 is stacked on the p-type silicon substrate 80. An n$^+$-p plug 92 is formed in a groove 85 of the SiO$_2$ oxide film layer 84. The n$^+$-p plug 92 is electrically connected to the p-type silicon substrate 80 through the n$^+$ high concentration impurity area 83. The n$^+$-p plug 92 may be made of a metal such as tungsten. Furthermore, an open plug 94 in a floating state exists in the oxide film layer 84. Such an open plug defect is detected in this inspection example.

When an electron beam is irradiated onto the wafer W having the cross-sectional structure in FIG. 11A, the surface potential reaches several V (on the order of −1 to −2 V) in an area where the n$^+$-p plug 92 is formed. A micro current flows into the p-type silicon substrate 80 thereafter. More specifically, the n$^+$ high concentration impurity area 83 and p-type silicon substrate 80 are connected in a forward direction via a depleted layer (not shown). When an electron beam is shot, electrons are accumulated until the surface potential reaches a certain potential (several V). However, when the surface potential reaches the certain potential, electrons flow into the p-type silicon substrate 80 as a current.

FIG. 11B shows a variation with a lapse of time of the surface potential of the wafer W when an electron beam of low landing energy is irradiated onto the wafer W in FIG. 11A. In FIG. 11B, at the n$^+$-p plug 92, the surface potential increases on the negative side until reaching such certain potential (several V, e.g., on the order of −1 to −2 V) as described above. When the surface potential reaches the above-mentioned potential, a current flows into the p-type silicon substrate 80. The current value becomes constant. On the other hand, electrons are accumulated at the open plug 94 as the electron irradiation time elapses. Therefore, the surface potential continues to increase on the negative side in proportion to the electron irradiation time.

Figure 12:
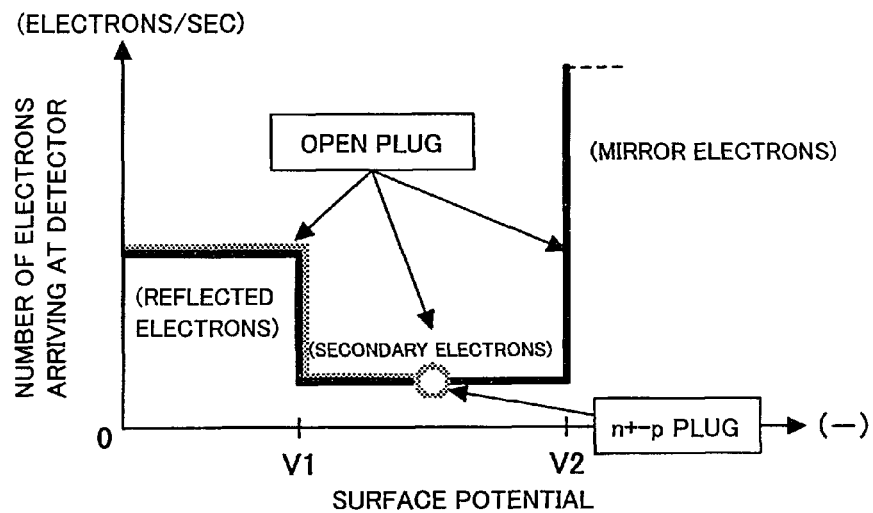
FIG. 12 shows dependency on surface potential of the number of electrons arriving at the detector of the wafer shown in FIG. 11A.

FIG. 12 shows dependency on surface potential of the number of arriving electrons. The number of arriving electrons is the number of electrons generated from the n$^+$-p plug 92 and open plug 94 shown in FIG. 11A and arriving at the detector. As shown in FIG. 12, at the open plug 94, the type of electrons generated varies from reflected electrons to secondary electrons and mirror electrons as the surface potential changes. This is the same as the first inspection example. On the other hand, as for the n$^+$-p plug 92, reflected electrons are detected when the surface potential is low. When the surface potential enters the generating area (detection area) of secondary electrons through the generating area (detection area) of reflected electrons, the surface potential becomes constant at some midpoint. The number of electrons arriving at the detector also becomes constant. This corresponds to the line of the n$^+$-p plug 92 in FIG. 11B. In FIG. 11B, the surface potential becomes constant, for example, on the order of −1 to −2 V and does not further increase toward the negative side. The number of electrons generated per unit time becomes constant in this stage. A value greater than the amount of variation of the surface potential of the wafer W (e.g., on the order of −1 to −2 V) is selected, for example, as the landing energy of the primary electron beam (more specifically several eV or more). Therefore, it is possible to obtain a state as shown in FIG. 12 in which reflected electrons and secondary electrons are detected but mirror electrons are not detected.

Figure 13:
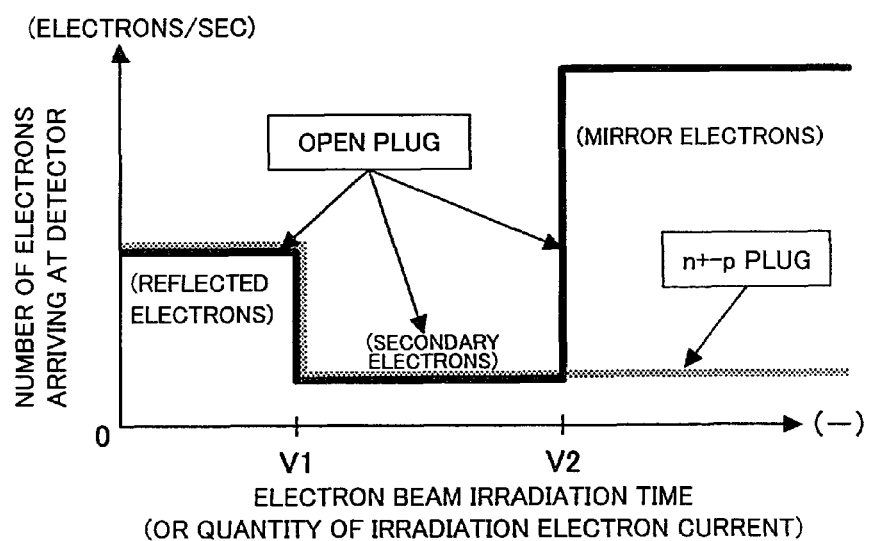
FIG. 13 shows a relationship between an electron beam irradiation time and the number of electrons arriving at the detector per unit time when an electron beam is irradiated onto the $n^+$-p plug and open plug.

FIG. 13 shows a relationship between an electron beam irradiation time and the number of electrons arriving at the detector per unit time when an electron beam is irradiated onto the n$^+$-p plug 92 and open plug 94. In FIG. 13, the horizontal axis is changed from the surface potential in FIG. 12 to the electron beam irradiation time.

As shown in FIG. 13, in the reflected electron detection area and secondary electron detection area of the open plug 94, the same number of reflected electrons and secondary electrons are detected from both n$^+$-p plug 92 and open plug 94. However, in the mirror electron detection area of the open plug 94, mirror electrons are detected from the open plug 94, whereas secondary electrons continue to be detected from the n$^+$-p plug 92. The reason is as has been explained in FIG. 13, that is, the surface potential of the n$^+$-p plug 92 becomes constant at a certain potential (several V) of the secondary electron detection area, therefore, even when the electron beam continues to be irradiated, only a constant number of secondary electrons per unit time are emitted.

Figures 14A, 14B, 14C:
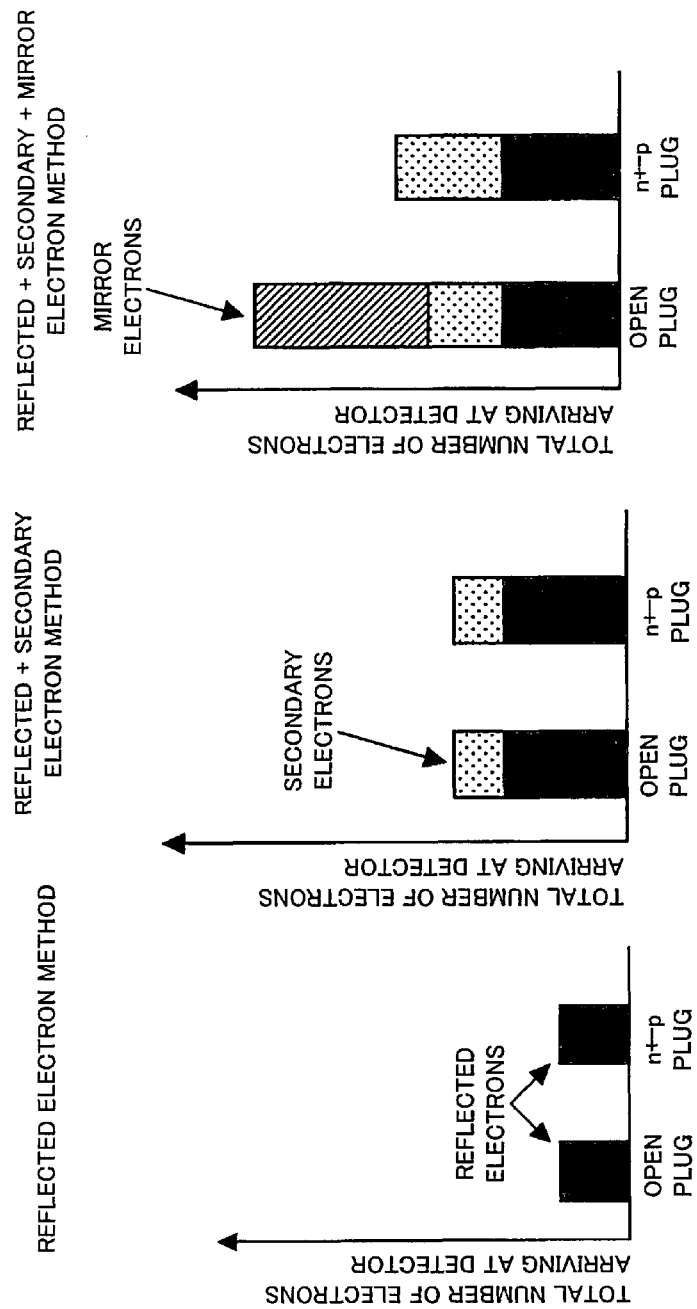
FIGS. 14A to 14C illustrate an inspection method of detecting an open plug by detecting electrons in a area including the reflected electron detection area.

FIG. 14A to FIG. 14C show the inspection method of detecting the open plug 94 using the relationship explained with reference to FIG. 11A to FIG. 13. In FIG. 14A to FIG. 14C, detection of electrons is started when reflected electrons are generated. In FIG. 14A to FIG. 14C, the total number of electrons (total number of electrons arriving at the detector) of the n$^+$-p plug 92 is compared with that of the open plug 94.

FIG. 14A compares the total number of electrons of the open plug 94 with that of the n$^+$-p plug 92 in the reflected electron detection area of the open plug 94. In FIG. 14A, the same number of reflected electrons are detected from the open plug 94 and n$^+$-p plug 92. Therefore, there is no brightness difference between the acquired images of both plugs. FIG. 14A is not suitable for detection of the open plug 94.

FIG. 14B compares the total number of electrons of the open plug 94 with that of the n$^+$-p plug 92 in the area from the reflected electron detection area to the secondary electron detection area of the open plug 94. In FIG. 14B, the same number of reflected electrons and secondary electrons are detected from the open plug 94 and n$^+$-p plug 92. No difference is produced in the total number of electrons arriving at the detector between both plugs. Therefore, FIG. 14B is not suitable for detection of the open plug 94.

FIG. 14C compares the total number of electrons of the open plug 94 with that of the n$^+$-p plug 92 in the area from the reflected electron detection area to the mirror electron detection area of the open plug 94. In FIG. 14C, all types of electrons including reflected electrons, secondary electrons and mirror electrons are detected from the open plug 94. On the other hand, only reflected electrons and secondary electrons are detected from the n$^+$-p plug 92. As shown in FIG. 13, in the mirror electron detection area of the open plug 94, the quantity of mirror electrons detected from the open plug 94 by far exceeds the quantity of secondary electrons detected from the n$^+$-p plug 92. Therefore, the quantity of mirror electrons detected from the open plug 94 is definitely larger than that of the n$^+$-p plug 92. As for the total number of electrons arriving at the detector, the number of electrons of the open plug 94 by far exceeds the number of electrons of the n$^+$-p plug 92. Therefore, in the inspection in FIG. 14C, the acquired image of the open plug 94 is brighter than the acquired image of the n$^+$-p plug 92. The open plug 94 can be detected using the brightness difference. Therefore, this inspection suitably detects an electrical difference using voltage contrast.

In order to perform the inspection in FIG. 14C, detection of electrons is started when the primary electron beam is irradiated onto the wafer W and initial reflected electrons are generated. Therefore, the irradiation area changing sections 13 and 14 change the position of the irradiation area 15 shown in FIG. 2C and realize a viewing area preceding type embodiment. According to such embodiment, detection is started from the stage in which reflected electrons are generated and all electrons generated from the wafer W are detected in the viewing area 25. Therefore, this inspection can be performed.

The same applies to inspections in FIG. 14A and FIG. 14B which are not suitable for detection of the open plug 94. Detection is started from the stage in which reflected electrons are generated and electrons generated from the wafer W are detected in these inspections, too. Therefore, the viewing area preceding type irradiation area change shown in FIG. 2C is applied.

FIG. 15A and FIG. 15B show an inspection method of detecting electrons after secondary electrons are generated. Electrons are not detected in the reflected electron detection area of the open plug 94.

FIG. 15A compares the total number of electrons (total number of electrons arriving at the detector) of the open plug 94 with that of the $n^+$-p plug 92 in the secondary electron detection area of the open plug 94. In FIG. 15A, the same number of secondary electrons are detected from the open plug 94 and $n^+$-p plug 92. Therefore, no brightness difference is produced between the acquired images of both plugs. This inspection is not suitable for detection of the open plug 94.

FIG. 15B compares the total number of electrons of the open plug 94 with that of the $n^+$-p plug 92 in the secondary electron detection area and mirror electron detection area of the open plug 94. In FIG. 15B, only secondary electrons are detected from the $n^+$-p plug 92. On the other hand, secondary electrons are detected and then mirror electrons are detected from the open plug 94. As shown in FIG. 15B, the quantity of mirror electrons detected from the open plug 94 is by far larger than the quantity of secondary electrons detected from the $n^+$-p plug 92. As for the total number of electrons arriving at the detector, the number of electrons of the open plug 94 is definitely larger. Therefore, the acquired image of the secondary optical system 20 of the open plug 94 is brighter than the acquired image of the $n^+$-p plug 92. Thus, the difference in surface potential between both plugs can generate the brightness difference in the corresponding images. Therefore, the inspection in FIG. 15B can detect an electrical difference and is suitably applicable to detection or the like of the open plug 94.

In order to perform inspections in FIG. 15A and FIG. 15B, the irradiation area changing sections 13 and 14 change the position of the irradiation area 15 with respect to the viewing area 25 and realize the irradiation area preceding type embodiment in FIG. 2A and FIG. 2B. The irradiation area 15 is set so that reflected electrons are emitted in the precharging area 16. In the viewing area 25, electrons detected are those generated in and after the secondary electron detection area of the open plug 94. Therefore, inspections in FIG. 15A and FIG. 15B are preferably performed.

FIG. 16 shows an inspection whereby the open plug 94 is detected using the mirror electron detection area of the open plug 94. FIG. 16 compares the total number of electrons of the open plug 94 with that of the $n^+$-p plug 92 in the mirror electron detection area of the open plug 94. In FIG. 16, only mirror electrons are detected from the open plug 94 and only secondary electrons are detected from the $n^+$-p plug 92. As explained in FIG. 13, this is because only secondary electrons are detected from the $n^+$-p plug 92 in the mirror electron detection area of the open plug 94. Therefore, in the total number of electrons arriving at the detector, the number of electrons detected from the open plug 94 by far exceeds the number of electrons detected from the $n^+$-p plug 92. The acquired image of the open plug 94 is brighter than the acquired image of the $n^+$-p plug 92 and both plugs can be distinguished. Therefore, inspection in FIG. 16 suitably detects mainly an electrical difference of the wafer W.

In the inspection in FIG. 16, only the mirror electron detection area of the open plug 94 is used. Reflected electrons and secondary electrons should not be detected. Therefore, the irradiation area changing sections 13 and 14 change the irradiation area 15 and realize the irradiation area preceding type embodiment in FIG. 2A and FIG. 2B. This causes reflected electrons and secondary electrons to be generated in the precharging area 16. In the viewing area 25, only mirror electrons are detected. The irradiation area 15 is preferably set so that the precharging area 16 becomes sufficiently large. Therefore, Embodiment (A-1) or (A-3) in FIG. 2A may be applied.

As has been explained so far, in the second inspection example, the inspection methods in FIG. 14C, FIG. 15B and FIG. 16 are suitable for detection of open defects using voltage contrast. In the second inspection example, the irradiation area changing sections 13 and 14 appropriately change the position of the irradiation area 15 with respect to the viewing area 25 to perform the respective inspections as in the case of the first inspection example. For example, in the inspection in FIG. 14C, detection is started from the reflected electron area. Therefore, the position of the irradiation area 15 is changed so that the field of view preceding type embodiment in FIG. 2C is applied. The position of the irradiation area 15 is changed so that the irradiation area preceding type embodiment in FIG. 2A and FIG. 2B is applied in the inspection in FIG. 15B. The irradiation position is set so that the emissions of reflected electrons are finished during irradiation of the electron beam in the precharging area 16. Furthermore, in the inspection in FIG. 16, the position of the irradiation area 15 is changed so that the irradiation area preceding type embodiment in FIG. 2A and FIG. 2B is applied. The irradiation position is set so that the emissions of reflected electrons and secondary electrons in the precharging area 16 are finished. Thus, the irradiation area changing sections 13 and 14 change the position of the irradiation area 15 of the electron beam suitable for the respective inspections and thereby an appropriate inspection is performed according to the type of the wafer W or the like.

In the inspections in FIG. 14A, FIG. 14B and FIG. 15A which are not suitable for detection of open defects, the light/dark difference between the acquired images of the defective part and the normal part is small. In these inspections, voltage contrast is not obtained, but an image of the wafer surface is obtained. The obtained images can be used for an inspection of defects in a wiring pattern. The irradiation position changing section 13 preferably makes an appropriate change to the irradiation position in this case, too.

Third Inspection Example

Next, in a third inspection example, an open plug defect is detected in the wafer W in which a $p^+$-n plug is formed.

Figure 17A:
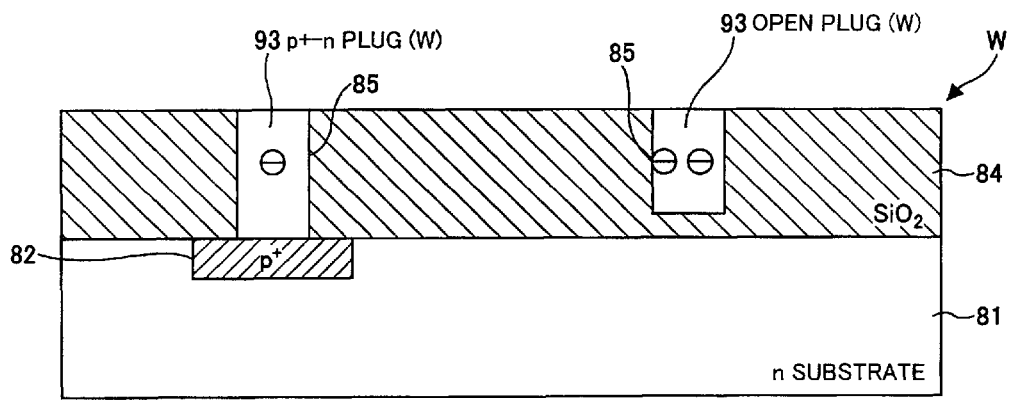
FIGS. 17A and 17B show a wafer to be inspected in a third inspection example.
Figure 17B:
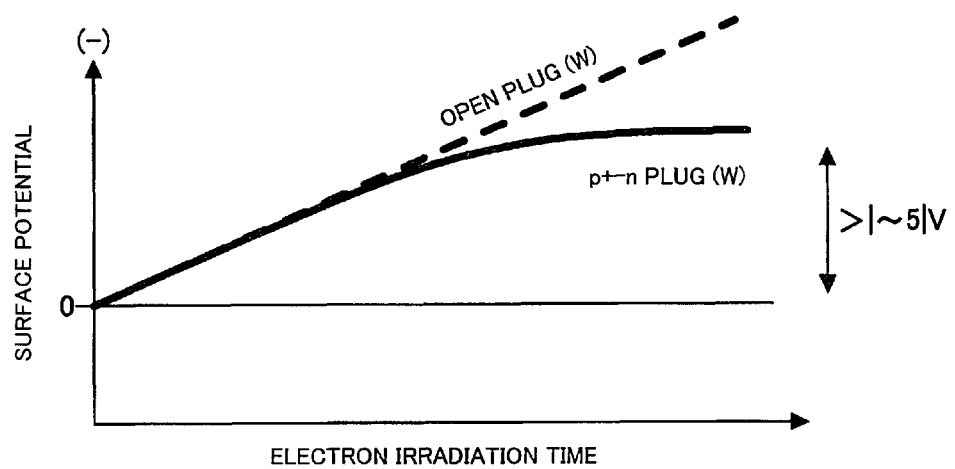

FIG. 17A and FIG. 17B illustrate the nature of the wafer W to be inspected in the third inspection example. FIG. 17A shows a cross-sectional structure of the wafer W in which the $p^+$-n plug is formed.

As shown in FIG. 17A, the wafer W to be inspected is provided with an n-type silicon substrate 81 as a supporting substrate and an opposite conductive type p+ high concentration impurity area 82 is provided in the surface thereof. An $SiO_2$ oxide film layer 84 is formed on the n-type silicon substrate. A $p^+$-n plug 93 is formed in a groove 85 of the oxide film layer 84. The $p^+$-n plug 93 is electrically connected to the n-type silicon substrate 81 through the p+ high concentration impurity area 82. Furthermore, an open plug 94 in a floating state exists in the oxide film layer 84. Such an open plug defect is detected in this example.

When an electron beam is irradiated onto the $p^+$-n plug 93 in FIG. 17A, the states of the p+ high concentration impurity area 82 and n-type silicon substrate 81 become the same as the state in which a reverse voltage is gradually applied to a diode. Therefore, electrons are accumulated in the $p^+$-n plug 93 up to a certain negative potential. When the voltage exceeds the certain negative potential, a reverse current starts to flow from the $p^+$-n plug 93 into the n-type silicon substrate. The potential of the $p^+$-n plug 93 does not further increase toward the negative side.

Next, FIG. 17B shows a state variation when an electron beam is irradiated onto the $p^+$-n plug 93 and open plug 94 of the wafer W shown in FIG. 17A. FIG. 17B shows a relationship between an electron irradiation time and surface potential.

In FIG. 17B, the open plug 94 is in a floating state. Therefore, at the open plug 94, electrons are accumulated on the plug surface accompanying the irradiation of the electron beam and the surface potential negatively increases in proportion to the passage of time. On the other hand, at the $p^+$-n plug 93, as has been explained with reference to FIG. 17A, the surface potential negatively increases toward the negative side up to a certain negative potential in proportion to the irradiation of the electron beam. When the surface potential reaches the certain value, the surface potential stays at a constant value. This phenomenon is similar to the phenomenon observed in the diode as described above. When a reverse voltage is applied to the diode, a reverse current starts to flow at the certain voltage. In many cases, the absolute value of the constant voltage value is, for example, approximately 5 V or less, that is, the constant value is approximately −5 V or more. This constant value varies from one device to another. In the above described second inspection example, as shown in FIG. 11A and FIG. 11B, the constant value of the surface potential is, for example, on the order of −1 to −2 V. Therefore, the constant value of the third inspection example is definitely greater than the constant value in the second inspection example.

In the third inspection example, the wafer W in which the $p^+$-n plug 93 is formed is inspected, while in the second inspection example, the wafer W in which the $n^+$-p plug 92 is formed is inspected. The relationship between the electron irradiation time and surface potential in the third inspection example is similar to that in the second inspection example. However, the value of the constant potential shown by a normal wiring plug differs between two examples.

Figure 18:
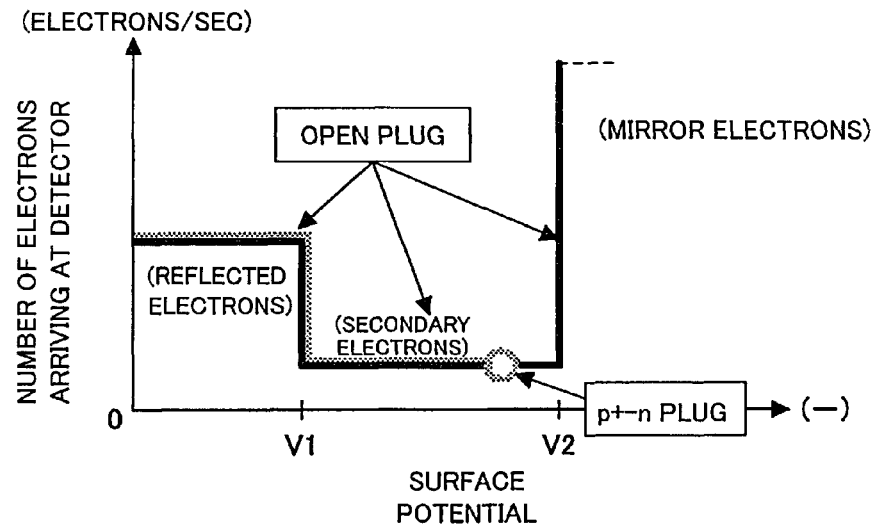
FIG. 18 shows dependency on surface potential of the number of electrons arriving at the detector when an electron beam is irradiated onto the wafer in the third inspection example.

FIG. 18 shows dependency on surface potential of the number of arriving electrons. The number of arriving electrons is the number of electrons generated from the $p^+$-n plug 93 and open plug 94 formed in the wafer W shown in FIG. 17A and arriving at the detector.

In FIG. 18, in the open plug 94, as has been explained so far, the type of electrons changes from reflected electrons to secondary electrons and mirror electrons as the surface potential negatively increases. On the other hand, in the $p^+$-n plug 93, reflected electrons are generated in a stage in which the surface potential is low as in the case of the open plug 94. Next, secondary electrons are generated as the surface potential negatively increases. However, the surface potential becomes constant at some midpoint of the stage in which secondary electrons are generated. The surface potential does not reach the area where mirror electrons are generated. The constant potential is greater toward the negative side than the constant potential in the second inspection example shown in FIG. 12, as already explained. In the case of the $p^+$-n plug 93, the surface potential becomes constant with a value on the order of −5 V or more as shown in FIG. 17B. This value is greater toward the negative side than the constant potential (on the order of −1 to −2 V) of the $n^+$-p plug 92. Therefore, the surface potential becomes constant at a point where the constant potential is greater toward the negative side than the constant potential in FIG. 12. Mirror electrons start to be generated at a surface potential of a level such as −10 V, −20 V. Therefore, with this surface potential characteristic, the surface potential does not reach the mirror electron detection area.

Figure 19:
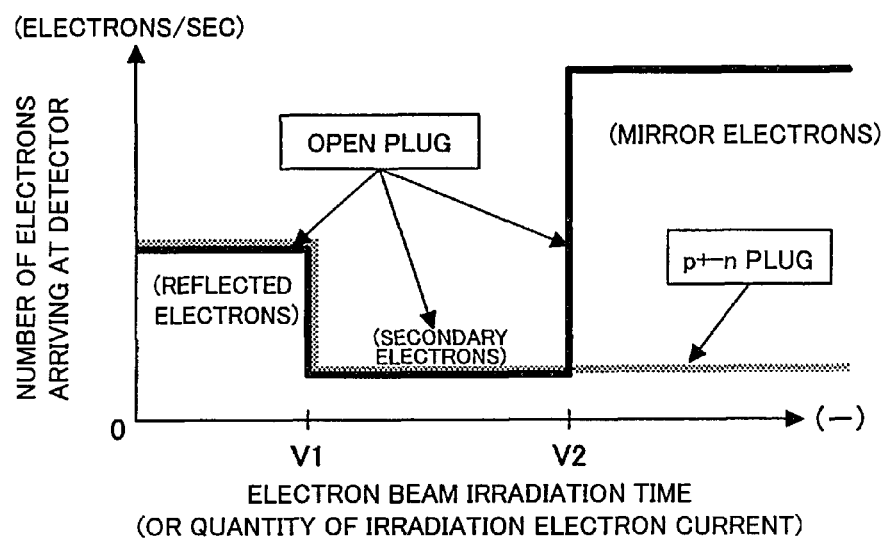
FIG. 19 shows a relationship between an electron beam irradiation time of the wafer and the number of electrons arriving at the detector in the third inspection example.

FIG. 19 shows a relationship between an electron beam irradiation time and the number of electrons arriving at the detector per unit time of the $p^+$-n plug 93 and open plug 94. In FIG. 19, the horizontal axis is changed from the surface potential in FIG. 18 to an electron beam irradiation time.

As shown in FIG. 19, in the open plug 94, electrons generated change from reflected electrons to secondary electrons and mirror electrons with the passage of the electron beam irradiation time. In the $p^+$-n plug 93, the surface potential enters the secondary electron detection area beyond the reflected electron detection area. However, the surface potential does not reach the mirror electron detection area. Therefore, secondary electrons continue to be generated.

Figures 20A, 20B, 20C:
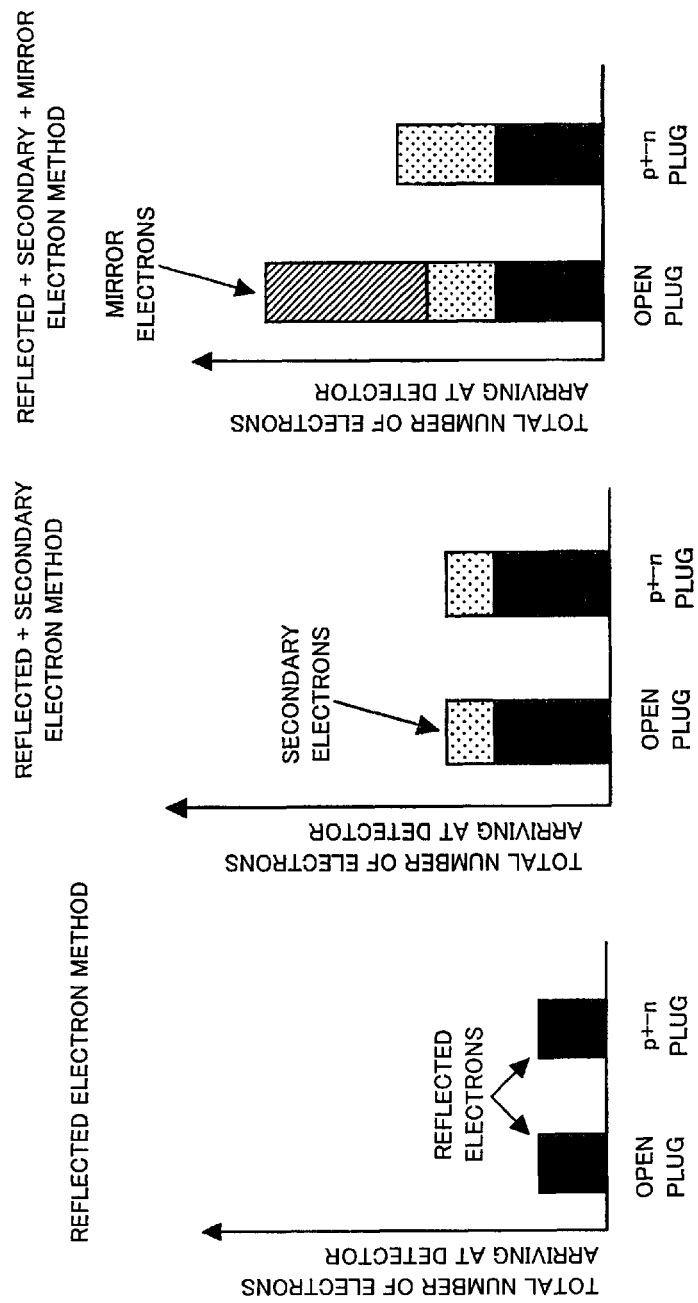
FIGS. 20A to 20C illustrate an embodiment detecting an open plug by detecting electrons including reflected electrons from the wafer of the third inspection example.

FIG. 20A to FIG. 20C show a method of detecting the open plug 94 out of the $p^+$-n plug 93 and open plug 94. Here, detection of electrons starts from the reflected electron detection area.

FIG. 20A compares the total number of electrons (total number of electrons arriving at the detector) of the open plug 94 with that of the $p^+$-n plug 93 in the reflected electron detection area of the open plug 94. In FIG. 20A, the same number of reflected electrons are detected from the open plug 94 and $p^+$-n plug 93. No bright/dark difference is generated between these acquired images. Therefore, this inspection is not suitable for detection of the open plug 94.

FIG. 20B compares the total number of electrons of the open plug 94 with that of the $p^+$-n plug 93 in the area from the reflected electron detection area to the secondary electron detection area of the open plug 94. In FIG. 20B, the same number of reflected electrons and secondary electrons are detected from the open plug 94 and $p^+$-n plug 93 and the total number of electrons arriving at the detector is also the same. No bright/dark difference is generated between the acquired images from both plugs. Therefore, this inspection is not suitable for detection of the open plug 94.

FIG. 20C compares the total number of electrons of the open plug 94 with that of the $p^+$-n plug 93 in the area from the reflected electron detection area to the mirror electron detection area of the open plug 94. As shown in FIG. 20C, the number of mirror electrons detected drastically increases in the open plug 94. However, the increment of secondary electrons of the $p^+$-n plug 93 is small. Therefore, in both total numbers of electrons arriving at the detector, the number of electrons of the open plug 94 by far exceeds the number of electrons of the $p^+$-n plug 93. Therefore, in this inspection, a light-dark difference is produced between the acquired images of the open plug 94 and $p^+$-n plug 93. The open plug 94 can be detected using the voltage contrast of the acquired images. Therefore, this inspection is suitable for detection of an electrical difference of the open plug 94 or the like.

In order to execute the detection method shown in FIG. 20A to FIG. 20C, reflected electrons need to be detected. Therefore, the field of view preceding type embodiment in FIG. 2C is applied. The irradiation area changing sections 13 and 14 change the position of the irradiation area 15 so that the irradiation area 15 follows the viewing area 25.

FIG. 21A and FIG. 21B show a method of detecting the open plug 94 out of the $p^+$-n plug 93 and open plug 94 without using reflected electrons.

FIG. 21A compares the total number of electrons of the open plug 94 with that of the $p^+$-n plug 93 in the secondary electron detection area of the open plug 94. In FIG. 21A, only the same number of secondary electrons are detected from the open plug 94 and $p^+$-n plug 93. No bright/dark difference is produced between the acquired images of both plugs. Therefore, this inspection is not suitable for detection of the open plug 94.

FIG. 21B compares the total number of electrons of the open plug 94 with that of the $p^+$-n plug 93 in the secondary electron detection area and mirror electron detection area of the open plug 94. In FIG. 21B, secondary electrons and mirror electrons are detected in the open plug 94 and only secondary electrons are detected in the $p^+$-n plug 93. The number of mirror electrons detected is by far greater than the number of secondary electrons detected. Therefore, the total number of electrons of the open plug 94 by far exceeds that of the $p^+$-n plug 93. Therefore, the acquired image of the open plug 94 in the secondary optical system 20 is brighter than the acquired image of the $p^+$-n plug 93. The open plug 94 can be detected from the voltage contrast of both images. Therefore, this inspection suitably detects an electrical difference.

In the inspection method shown in FIG. 21A and FIG. 21B, the irradiation area changing sections 13 and 14 change the position of the irradiation area 15 so as to realize the irradiation area preceding type embodiment shown in FIG. 2A and FIG. 2B. The precharging area 16 is set so that reflected electrons are not detected in the viewing area 25, that is, reflected electrons are emitted from the wafer W in the precharging area 16.

FIG. 22 shows the method of detecting the open plug 94 from the $p^+$-n plug 93 and open plug 94 using the mirror electron detection area of the open plug 94. FIG. 22 compares the total number of electrons of the open plug 94 with that of the $p^+$-n plug 93 in the mirror electron detection area of the open plug 94. In FIG. 22, only mirror electrons are detected from the open plug 94 and only secondary electrons are detected from the $p^+$-n plug 93. The total number of mirror electrons (total number of electrons arriving at the detector) is by far greater than the total number of secondary electrons. The acquired image of the open plug 94 is brighter than the acquired image of the $p^+$-n plug 93. The open plug 94 can be detected from the voltage contrast of acquired images. This inspection is suitable for detection of an electrical difference.

The inspection in FIG. 22 only uses the mirror electron detection area without using the reflected electron detection area and secondary electron detection area of the open plug 94. Therefore, the irradiation area preceding type embodiment in FIG. 2A and FIG. 2B is suitably used. The irradiation area changing sections 13 and 14 change the irradiation area so that reflected electrons and secondary electrons of the open plug 94 are emitted in the precharging area 16.

In the third inspection example, the inspection method in FIG. 20C, FIG. 21B and FIG. 22 is suitable to detect open defects of the wafer W in which the $p^+$-n plug 93 is formed.

On the other hand, the inspections in FIG. 20A, FIG. 20B and FIG. 21A, the bright/dark difference is small. For this reason, these inspections are not suitable for detection of electrical difference using voltage contrast. However, these inspections are suitable for acquiring surface images of the wafer W and inspecting pattern defects.

In order to perform these various inspections, the irradiation area changing sections 13 and 14 select the embodiment for changing the position of the irradiation area 15 with respect to the viewing area 25 as shown in FIG. 2A, FIG. 2B or FIG. 2C. By applying such various embodiments, an inspection adaptable to the inspection target can be realized.

Figures 23A, 23B:
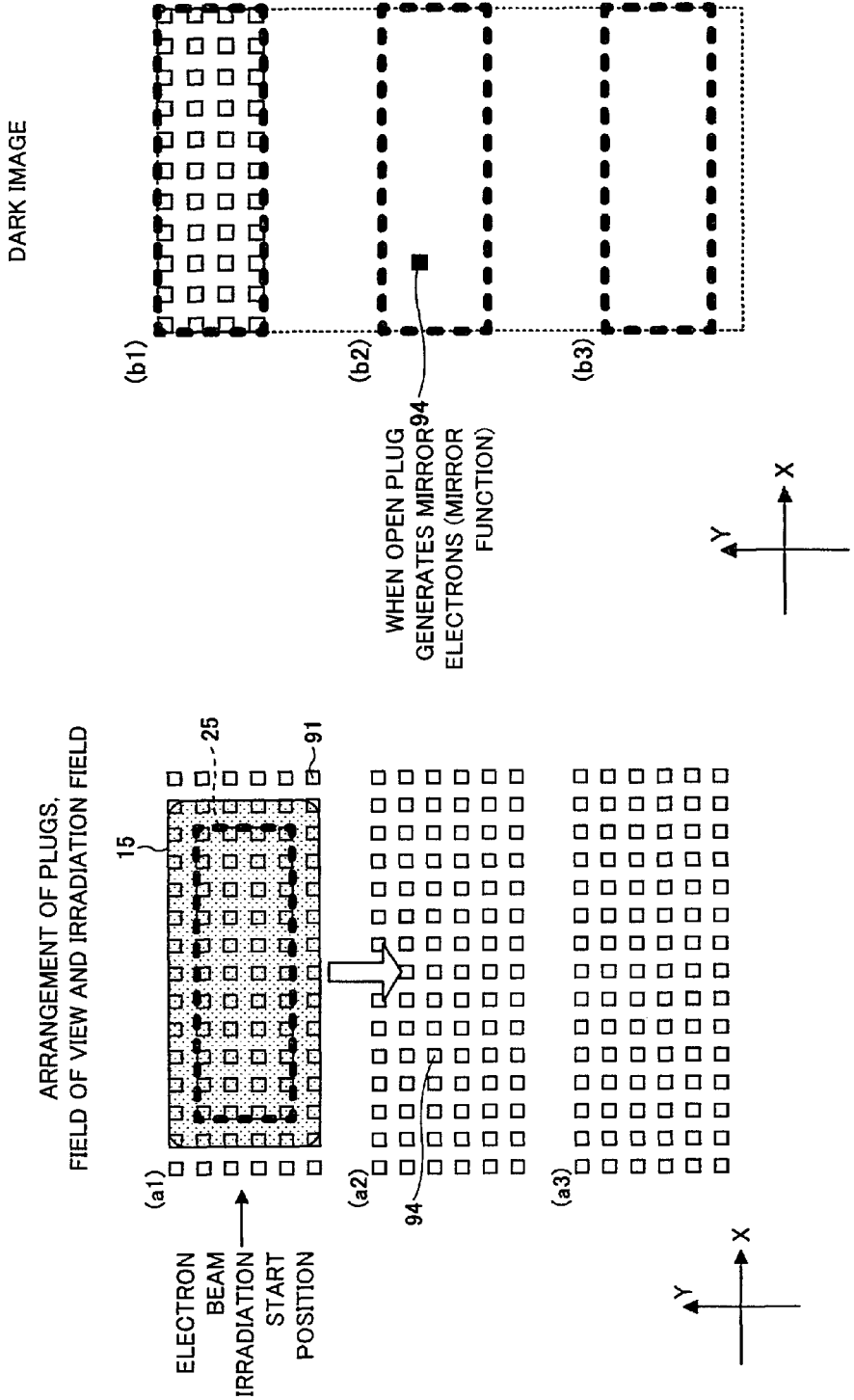
FIGS. 23A and 23B show an example of inspection image according to an inspection method using mirror electrons.

FIG. 23A and FIG. 23B are examples of inspection image obtained by the defect inspection of the open plug 94. These images are obtained by the inspections using mirror electrons shown in FIG. 9A to FIG. 10, FIG. 15A to FIG. 16 and FIG. 21A to FIG. 22.

In FIG. 23A and FIG. 23B, (a1) to (a3) show surfaces of the wafer W in which the grounding plugs 91 are formed and (b1) to (b3) show acquired images corresponding to the respective surfaces of the wafer W. In (a1) of FIG. 23A, the irradiation area 15 is greater than the viewing area 25. Furthermore, the irradiation area 15 precedes the viewing area 25. The arrow in the −Y direction in FIG. 23A indicates the relative moving direction of the irradiation area 15 and viewing area 25. Actually, the stage 30 moves in the +Y direction.

(b1) in FIG. 23B is a detected image of the detector 22 on the detection surface corresponding to (a1) in FIG. 23A. In (a1) of FIG. 23A, at the moment an electron beam is irradiated, reflected electrons are detected and the whole viewing area is detected.

Next, the stage 30 is scanned in the +Y direction or an electron beam is scanned in the −Y direction. The irradiation area 15 and viewing area 25 move while keeping the positional relationship in (a1) of FIG. 23A. As shown in (a2) of FIG. 23A, when the open plug 94 is included, only the portion of the open plug 94 glows brightly as shown in (b2) of FIG. 23B. Mirror electrons are not detected from the normal plug.

In order to increase detected electrons from the defective part (open plug 94), the inspections in FIG. 23A and FIG. 23B are performed under a condition that mirror electrons are detected only from the portion of the open plug 94, that is, under a condition that mirror electrons are not detected from other normal plugs. Such an inspection condition is called a "dark image mode." In the inspections in FIG. 23A and FIG. 23B, the surface potential of mirror electrons is sufficiently large compared to that of reflected electrons and secondary electrons. This causes only defective plugs to glow brightly in the dark image and be easily detected.

In (a3) of FIG. 23A, the stage 30 or electron beam is further scanned and no open plug 94 exists in the viewing area 25. In this case, as shown in (b3) of FIG. 23B, the image in the dark image mode darkens as a whole.

Therefore, the open plug 94 can be easily detected using the dark image mode.

Figures 24A, 24B:
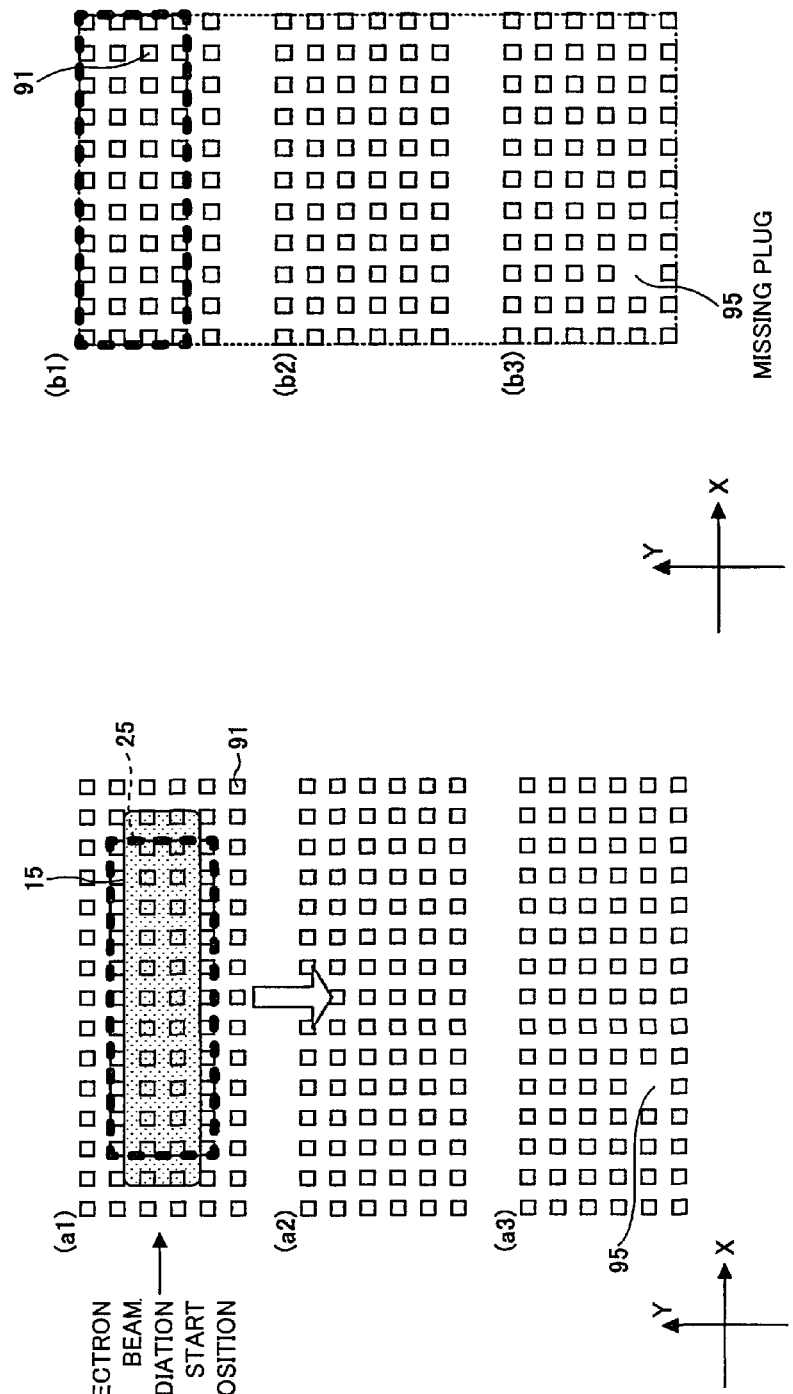
FIGS. 24A and 24B show an example of detecting a surface defect of the wafer using reflected electrons.

FIG. 24A and FIG. 24B show examples where surface defects of the wafer W are detected by selectively using reflected electrons.

In FIG. 24A, (a1) shows a positional relationship between the irradiation area 15 of an electron beam, viewing area 25 and plug 91. In (a1) of FIG. 24A, the viewing area 25 precedes the irradiation area 15. As in the case of FIG. 23A, the stage 30 moves in the +Y direction and/or the electron beam moves in the −Y direction. This causes the inspection area to move. In (a1) of FIG. 24A, the position of the irradiation area 15 is changed so that the viewing area 25 precedes the irradiation area 15 with respect to the moving direction of the stage 30. Therefore, in the viewing area 25, the detection of electrons starts at timing at which the electron beam is first irradiated onto the wafer W and all electrons can continue to be detected. Therefore, reflected electrons generated in an initial stage of irradiation of the electron beam can continue to be detected. (b1) in FIG. 24B shows a detected image on the detection surface of the detector 22 corresponding to (a1) in FIG. 24A. In FIG. 24B, reflected electrons of all plugs 91 in the viewing area 25 are detected and images of all the plugs 91 are formed.

Next, the stage 30 or electron beam moves and the area in (a2) of FIG. 24A is irradiated. Reflected electrons are also detected in this area. In the initial stage, reflected electrons are detected irrespective of whether plugs are grounded or in an open (floating) state. Therefore, unless missing plugs exist in the pattern in (a2) of FIG. 24A, the corresponding detected images include the images of all the plugs 91 as shown in (b2) of FIG. 24B.

In (a3) of FIG. 24A, the stage 30 or electron beam further moves. In (a3) of FIG. 24A, a missing plug 95 exists. As shown in (b3) of FIG. 24B, no plug is detected at the location of the missing plug 95 in the corresponding detected image.

The above-mentioned inspection utilize the nature of reflected electrons that the reflected electrons image can be obtained if any metallic object exists at initial stage of the irradiation. The missing plug can be easily detected using this nature.

As described above, in the first inspection example to third inspection example, the inspection methods explained detect the open plug 94 when the grounding plug 91, $n^+$-p plug 92 and $p^+$-n plug 93 are formed on the wafer W. In the actual wafer W manufacturing process, the above described three types of plug (grounding plug 91, $n^+$-p plug 92 and $p^+$-n plug 93) are usually formed in the same wafer W. Therefore, it is preferable to adopt an inspection capable of commonly detecting the open plug 94 in the first to third inspection examples. Here, in the first inspection example, inspections in FIG. 8B, FIG. 9B and FIG. 10 are appropriate. In the second inspection example, inspections in FIG. 14C, FIG. 15B and FIG. 16 are appropriate. Inspections in FIG. 20C, FIG. 21B and FIG. 22 are appropriate in the third inspection example. Of these figures, FIG. 9B, FIG. 15B and FIG. 21B are common. That is, these inspections commonly use not reflected electrons but secondary electrons and mirror electrons. Furthermore, the inspections in FIG. 10, FIG. 16 and FIG. 12 are also common, that is, these inspections only use mirror electrons. Therefore, these detection methods can preferably detect the open plug 94 of the wafer W. Particularly, it is possible to detect the open plug 94 with minimum energy without using a precharging unit.

Fourth Inspection Example

In a fourth inspection example, electrical defects of VC-TEG are detected. "VC-TEG" here refers to a test element group in a voltage contrast inspection. To know structural dimension margins from the standpoint of an anti-short-circuit characteristic, a plurality of test element groups having different wire widths and wiring spaces are used.

The inspection method in FIG. 10 or FIG. 9A is appropriate to detect electrical defects of VC-TEG. The inspection method in FIG. 10 uses only mirror electrons. The inspection method in FIG. 9A detects not electrons in the reflected electron detection area but electrons in the secondary electron detection area. The basic structure of VC-TEG is similar to that of the wafer W having the grounding plugs 91. Therefore, the inspection method applicable to the first inspection example can also be suitably used here. The inspection methods in FIG. 10 and FIG. 9A can definitely generate voltage contrast. Furthermore, the inspection method in FIG. 8B is also applicable. The inspection method in FIG. 8B detects reflected electrons and secondary electrons.

On the other hand, the inspection methods in FIG. 8C and FIG. 9B are also applicable. The inspection method in FIG. 8C detects all electrons from reflected electrons to mirror electrons. The inspection method in FIG. 9B detects not reflected electrons but secondary electrons and mirror electrons. However, these inspection methods have only a small amount of margin for differentiation and it is difficult to set conditions. Furthermore, the inspection method in FIG. 8A only uses reflected electrons. This inspection method had little light-dark difference and it is difficult to detect electrical defects, therefore, FIG. 8A is hardly applicable.

When using the inspection methods in FIG. 10, FIG. 9A and FIG. 9B, the irradiation area is suitably changed so that the irradiation area preceding type embodiment shown in FIG. 2A and FIG. 2B are applied. Furthermore, when the inspection methods in FIG. 8B and FIG. 8C are used, the viewing area preceding type embodiment in FIG. 2C is preferable.

FIG. 25A and FIG. 25B show examples of VC-TEG wiring. FIG. 25A shows an example of normal VC-TEG. FIG. 25B shows an example of VC-TEG image containing defects.

In FIG. 25B, a case where the inspection method in FIG. 9A is applied will be considered. The inspection method in FIG. 9A detects electrons generated in the secondary electron detection area of the open plug 94. According to this inspection method, reflected electrons are always detected in the grounding wiring portion and secondary electrons are detected in the floating wiring portion 94. When, for example, the plug is tungsten, the number of reflected electrons detected is overwhelmingly larger than the number of secondary electrons. Therefore, the grounding wiring 91 is brighter and the floating wiring portion 94 is darker.

Figure 26B:
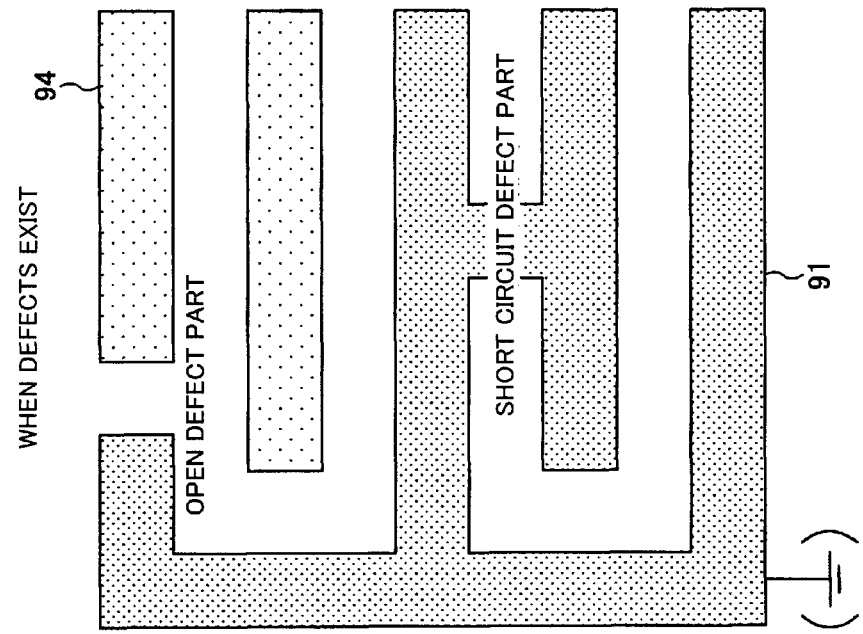
FIGS. 26A and 26B show an example where VC-TEG wiring is inspected using only mirror electrons.
Figure 26A:
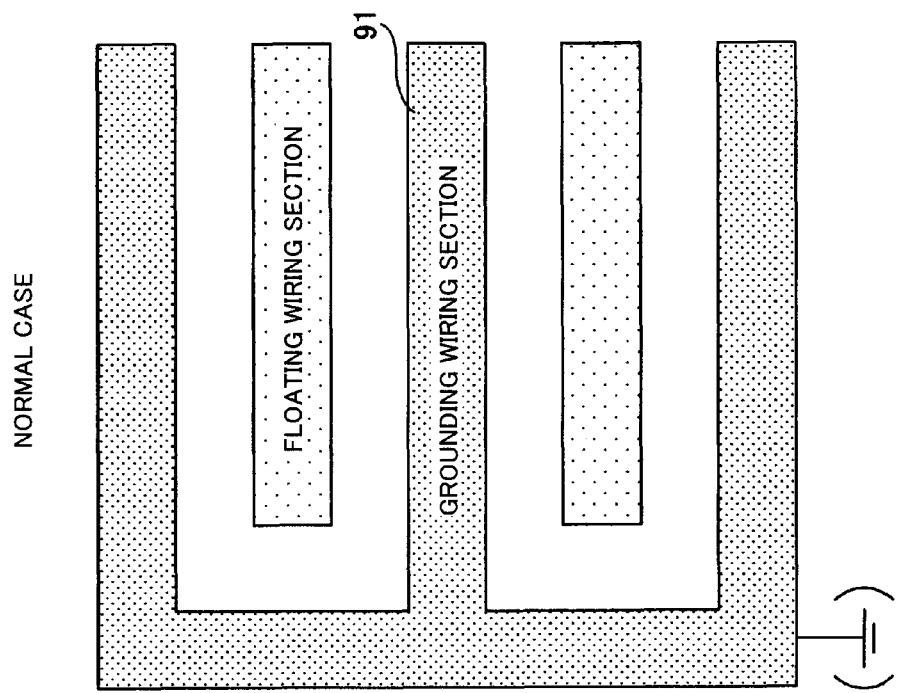

FIG. 26A and FIG. 26B show another inspection result. Here, VC-TEG wiring similar to that in FIG. 25A and FIG. 25B is inspected using the inspection method in FIG. 10. The inspection method in FIG. 10 uses only mirror electrons. FIG. 26A shows a normal detected image and FIG. 26B shows a detected image containing defects.

In FIG. 26A and FIG. 26B, when electrons generated in the mirror electron detection area are used, reflected electrons are detected in the grounding wiring portion 91. Mirror electrons are detected in the floating portion 94. The landing energy of the primary electron beam is set so that more mirror electrons than reflected electrons are generated. This causes the grounding wiring 91 to become darker and the floating wiring portion 94 to become brighter.

As described above, according to the fourth inspection example, it is possible to inspect not only the wafer W but also VC-TEG wiring.

"Removal of Foreign Matter"

An embodiment of the present invention is a foreign matter removing method of removing foreign matter on a sample surface onto which a charged particle beam is irradiated. The method includes acquiring charge information on the sample surface, detecting the foreign matter on the sample surface based on the acquired charge information, moving the sample in a horizontal direction, and charging an adsorption electrode facing and close to the sample surface with a polarity different from or opposite to a charge polarity of the foreign matter and thereby electrostatically adsorbing the foreign matter which approaches the adsorption electrode.

The method of the present invention as mentioned above can not only detect foreign matter on the sample surface but also remove the detected foreign matter using charge of the foreign matter upon detection the foreign matter.

The adsorption electrode may be incorporated in an objective lens arranged facing and close to the sample and the adsorption electrode may be charged to the same potential as that of the objective lens when the adsorption electrode does not electrostatically adsorb the foreign matter.

According to this method, the adsorption electrode can function as part of the objective lens when foreign matter is not electrostatically adsorbed from the sample surface and can function as the adsorption electrode only when foreign matter is electrostatically adsorbed. Therefore, foreign matter can be adsorbed without losing the normal foreign matter detection function.

The method of the present invention may further include a foreign matter collection adsorption step of charging a collection electrode facing the adsorption electrode with a polarity different from or opposite to the charge polarity of the foreign matter while cutting charge of the adsorption electrode and thereby adsorbing the foreign matter to the collection electrode.

Therefore, the method of the present invention can not only adsorb and removes the foreign matter on the sample surface but also collect the adsorbed foreign matter. Even when the amount of foreign matter is large, the foreign matter on the sample surface can be preferably removed.

The collection electrode may be made of a material charged with a polarity different from the charge polarity of the foreign matter through the irradiation of the charged particle beam and the collection electrode may be charged by irradiating a charged particle beam onto the collection electrode beforehand.

Therefore, an appropriate charge material is selected in accordance with the charge polarity of the foreign matter. The collection electrode can collect the foreign matter by being charged without using a facility for charging the collection electrode.

The charge polarity of the foreign matter may be positive. Therefore, the foreign matter can be collected when the foreign matter is positively charged.

The charge polarity of the foreign matter may also be negative. Therefore, the foreign matter can be collected when the foreign matter is negatively charged.

An aspect of the present invention is a charged particle beam apparatus that removes foreign matter on a sample surface irradiated with a charged particle beam, including a stage for mounting a sample thereon in a horizontally movable manner, a charge information acquisition section for acquiring charge information on the sample surface, a foreign matter detection section for detecting foreign matter on the sample surface based on the charge information, and an adsorption electrode facing the stage, wherein the adsorption electrode is charged with a polarity different from or opposite to a charge polarity of the foreign matter when the foreign matter on the sample surface approaches as the stage moves so that the adsorption electrode electrostatically adsorbs the foreign matter.

Therefore, the foreign matter on the sample surface is removed using the charge of the foreign matter upon detecting the foreign matter. The foreign matter can be removed while inspecting the foreign matter.

The apparatus of the present invention may include an objective lens provided close to the sample surface and having a plurality of electrodes, the adsorption electrode may be provided as part of the electrode closest to the sample surface out of the plurality of electrodes and a voltage may be applied to the adsorption electrode independently of the closest electrode. The adsorption electrode may be incorporated in the electrode closest to the sample surface.

Therefore the adsorption function can be obtained while the adsorption electrode is formed as part of the objective lens in appearance. Foreign matter on the sample surface can be removed while realizing space saving at the same time.

The adsorption electrode may be arranged in a ring shape. Therefore, the charged particle beam apparatus can detect foreign matter to recognize the position of the foreign matter on the sample and then reliably adsorb and remove the foreign matter.

The adsorption electrode may be arranged radially. Therefore, the foreign matter can be adsorbed and removed in real time while detecting foreign matter.

The stage may be provided with a collection electrode that can be charged with a polarity different from or opposite to that of the foreign matter. In accordance with this configuration, after adsorbing and removing the foreign matter on the sample, the foreign matter can be collected in a predetermined collection area. Therefore, even when the amount of foreign matter is large, the foreign matter can be collected continuously. Furthermore, it is also possible to reliably prevent re-sticking of the foreign matter to the sample surface.

As described above, the present invention can not only acquire charge information on the sample surface and observe the charged state of the sample surface but also detect and remove foreign matter on the sample surface.

Figure 27:
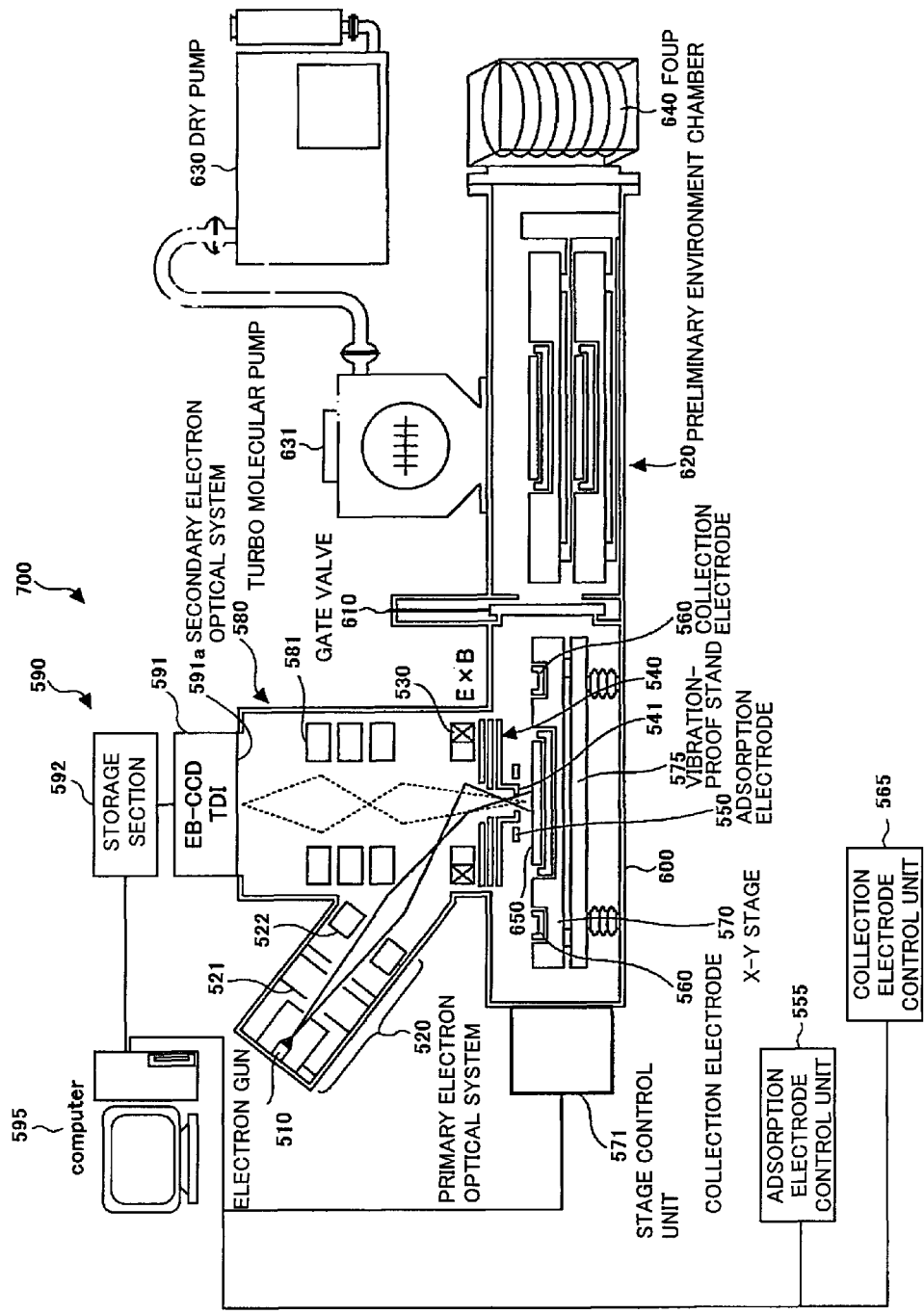
FIG. 27 shows an overall configuration of a charged particle beam apparatus 200 according to an embodiment of the present invention.

FIG. 27 shows an overall configuration of a charged particle beam apparatus 700 according to this embodiment. In FIG. 27, the charged particle beam apparatus 700 is equipped with an electron gun 510, a primary electron optical system 520, an E×B filter 530, an objective lens 540, an adsorption electrode 550, an adsorption electrode control unit 555, a collection electrode 560, a collection electrode control unit 565, a stage 570, a stage control unit 571, a vibration-proof stand 575, a secondary electron optical system 580, a charge information acquisition section 590 and a foreign matter detection section 595. Of these components, the electron gun 510, primary electron optical system 520, E×B filter 530, objective lens 540, adsorption electrode 550, collection electrode 560, stage 570, vibration-proof stand 575 and secondary electron optical system 580 are accommodated in a vacuum housing 600. The inside of the vacuum housing 600 is maintained under vacuum.

Furthermore, the charged particle beam apparatus 700 may also be provided with a preliminary environment chamber 620 to carry a sample 650 such as a semiconductor wafer into/out of the vacuum housing 600. The preliminary environment chamber 620 is separated from the vacuum housing 600 by a gate valve 610. The gate valve 610 can be opened/closed. A Foup 640 is provided on the atmosphere side. Furthermore, the charged particle beam apparatus 700 may also be provided with vacuum pumps such as a dry pump 630 and a turbo molecular pump 631 for evacuating the inside of the preliminary environment chamber 620.

The electron gun 510 is a charged particle beam generation source that generates an electron beam to be irradiated onto the sample 650 such as a semiconductor wafer. The electron gun 510 may be, for example, a thermionic emission type electron gun or a Schottky type electron gun. Any type or mode of the electron gun 510 may be used as far as the electron gun 510 has a configuration being able to generate a desired electron beam.

The primary electron optical system 520 forms a cross-sectional shape of the electron beam emitted from the electron gun 510 and at the same time guides the electron beam to the direction of the sample 650. The primary electron optical system 520 may include an aperture 521 and a lens 522 or the like. The aperture 521 is constructed of an aperture plate. The lens 522 may be constructed of an electrostatic lens such as quadruple lens and an electromagnetic lens or the like.

The E×B filter 530 is an electromagnetic filter that generates an electric field and a magnetic field in directions two-dimensionally orthogonal to each other. The E×B filter 530 changes the orientation of the electron beam guided from the primary optical system 520 by a Lorentz force and directs the beam toward the sample 650 vertically below.

The objective lens 540 is disposed close to the sample 650. The objective lens 540 performs final focusing or the like of the electron beam directed to the sample 650 by the ExB filter 530. The ExB filter 530 may be an electrostatic lens, electromagnetic lens or the like. Lenses used for various electron optical systems may be applied to the ExB filter 530. An electrostatic lens is used for the charged particle beam apparatus 700 of this embodiment. The objective lens 540 has a plurality of electrodes. In the objective lens 540, an electrode 541 is arranged closest to the sample 650. The electrode 541 has a concave part as shown in its cross-sectional shape. When an electron beam is irradiated, an electric field is applied to the objective lens 540 in a direction in which incident landing energy is reduced and thereby the objective lens 540 also perform a function of lessening impact of the electron beam on the sample 650.

The stage 570 mounts the sample 650 thereon. The stage 570 is a sample moving section for moving the sample 650 to a desired position. The stage 570 is an X-Y stage movable on the horizontal X-Y plane. The irradiation area of the electron beam at a time is extremely small compared to the whole area of the sample 650. Therefore, the sample 650 needs to be moved on the horizontal plane (X-Y plane) to perform a foreign matter inspection of the whole area to be inspected, even when the sample 650 is scanned with the electron beam. Furthermore, the charged particle beam apparatus 700 according to the present invention detects impurities or foreign matter such as dust existing on the sample 650 and adsorbs the detected impurities or foreign matter by an adsorption electrode provided at a predetermined position. Therefore, the foreign matter detected on the sample 650 needs to be brought close to the adsorption electrode. Such adsorption operation also needs the stage 570 movable on the horizontal plane. The stage 570 may be driven by an electromagnetic driving force, mechanical driving force or the like and driving means may be applied.

The vibration-proof stand 575 supports the stage 570 from below and removes vibration from the floor. Specifically, the vibration-proof stand 575 is provided with a function of absorbing or removing vibration from the floor employing a spring such as air spring, electromagnet or the like and thereby preventing vibration from being transmitted to the stage 570.

As described above, the sample 650 is supported by the mounting configurations 570 and 575. When irradiated with the electron beam, the sample 650 emits secondary electrons. Secondary electrons emitted from the sample 650 have acquired charge information, so-called voltage contrast, on the surface of the sample 650. By detecting such secondary electrons having acquired the charge information on the surface of the sample 650 and obtaining a voltage contrast image of the surface of the sample 650, it is possible to detect the existence of foreign matter on the sample 650.

Secondary electrons emitted from the sample 650 are accelerated upward by the electrode 541 of the objective lens 540 disposed in the vicinity of the sample 650 and guided to the secondary electron optical system 580. The secondary electron optical system 580 is a guide section for guiding secondary electrons emitted from the sample 650 to the charge information acquisition section 590. The secondary electron optical system 580 may include the ExB filter 530 and a lens 581. As already explained, the ExB filter 530 perform a function of changing the direction of the electron beam when irradiating an electron beam onto the sample 650 and directing the electron beam vertically downward to a location where the sample 650 is disposed. On the other hand, with regard to secondary electrons, the ExB filter 530 perform a function of causing a Lorentz force to act in the direction such that secondary electrons move straight and thereby guiding secondary electrons to the charge information acquisition section 590 located vertically above. Both the electron beam incident upon the sample 650 and secondary electrons emitted from the sample 650 pass through the ExB filter 530 and objective lens 540. Therefore, the ExB filter 530 and objective lens 540 can be considered that they function as the primary electron optical system 520 and the secondary electron optical system 580.

The lens 581 carries out focusing and directing secondary electrons to guide secondary electrons. Secondary electrons are guided by the secondary electron optical system 580 and the lens 581 causes the secondary electrons to form an image on a detection surface 591a of a detector 591 of the charge information acquisition section 590.

The charge information acquisition section 590 is configured to acquire charge information on the surface of the sample 650 and may be provided with the detector 591 and a storage section 592. The charge information may express the difference in surface potential such as voltage contrast as a two-dimensional image. Furthermore, an image like an actual photo may be acquired based on a two-dimensional image. With irradiation of an electron beam, the charged state differs in the position where no foreign matter exists and the position where the foreign matter exists on the surface of the sample 650. Therefore, by acquiring charge information on the surface of the sample 650, it is possible to know the existence and position of foreign matter on the sample 650.

The detector 591 has the detection surface 591a facing the vacuum housing 600 vertically below and detects secondary electrons with the detection surface 591a. The detector 591 detects secondary electrons emitted from the sample 650 and acquires charge information on the surface of the sample 650 based on secondary electrons. Various configurations may be applied to the detector 591. The detector 591 may be, for example, a two-dimensional type detector capable of forming a voltage contrast image of the sample 650 on the detection surface 591a as a mapped image. The two-dimensional type detector may be a CCD (Charge Coupled Device), TDI (Time Delay Integration)-CCD, EB (Electron beam)-CCD, EB-TDI or the like. The CCD and TDI convert electrons received with the detection surface 591a to light and then acquires charge information on the surface of the sample 650. The EB-CCD and EB-TDI can directly receive secondary electrons with the detection surface 591a. When the CCD or TDI-CCD is applied, the detector 591 may further include an MCP (multichannel plate) that amplifies received electrons and a fluorescent screen that converts electrons to light.

The storage section 592 is a configuration for storing charge information image acquired by the detector 591. The storage section 592 is a configuration such as a memory capable of storing two-dimensional images. Various storage apparatuses may be applicable to the storage section 592.

The foreign matter detection section 595 detects foreign matter from the charge information image stored in the storage section 592. As described above, the charged state of the charge information image differs in the position where the foreign matter exists and the position where no foreign matter exist. For example, the difference of charge information is expressed by voltage contrast. Foreign matter detection includes a foreign matter judgment process which recognizes the existence of foreign matter from acquired the charge information image and specifies the position of foreign matter. Such a foreign matter judgment processing calculation is performed by the foreign matter detection section 595. More specifically, for example, a predetermined potential difference threshold is set beforehand. When the potential difference between the position where foreign matter exists and the position where no foreign matter exists exceeds the predetermined threshold, the foreign matter detection section 595 detects foreign matter by performing calculation processing or the like judging that foreign matter exists. Therefore, the foreign matter detection section 595 may be constructed of a calculation processor such as a computer to perform such a foreign matter detection calculation. Therefore, the foreign matter detection section 595 detects the position of foreign matter.

Furthermore, the foreign matter detection section 595 not only detects the position of foreign matter but also detects a charge polarity of foreign matter. The charged particle beam apparatus 700 of this embodiment performs not only a step of detecting foreign matter but also a step of removing the detected foreign matter after detecting the foreign matter. Foreign matter is removed by charging the adsorption electrode 550 with a polarity opposite to the charge polarity of foreign matter, making the adsorption electrode approach foreign matter and adsorbing the foreign matter by an action of electrostatic attracting force. The foreign matter detection section 595 detects the location and charge polarity of foreign matter so as to be used for this adsorption processing.

Furthermore, the foreign matter detection section 595 is connected to the adsorption electrode control unit 555, collection electrode control unit 565 and stage control unit 571 and sends a control signal or charge information to these control units 555, 565 and 571. Based on the information on the position and charge polarity of foreign matter detected by the foreign matter detection section 595, the adsorption electrode control unit 555 and collection electrode control unit 565 determine polarities of the adsorption electrode 550 and collection electrode 560, and the stage control unit 571 controls the moving position of the stage 570.

Next, the adsorption electrode 550 and collection electrode 560 will be explained.

The adsorption electrode 550 is a foreign matter adsorption section for adsorbing and removing foreign matter on the sample 650. When foreign matter is charged through irradiation of an electron beam, the adsorption electrode 550 is charged with a polarity opposite to the polarity of charged foreign matter and adsorbs and removes the detected foreign matter by an electrostatic force. That is, the adsorption electrode 550 is controlled to be negatively charged if the foreign matter is positively charged and positively charged if the foreign matter is negatively charged. Therefore, the adsorption electrode 550 is charged with a polarity opposite to that of foreign matter and adsorbs foreign matter by an action of electrostatic attracting force. This control may be performed by the adsorption control unit 555 based on position information and charge information on foreign matter sent from the foreign matter detection section 595.

The adsorption electrode 550 may be arranged as part of and incorporated in the electrode 541 closest to the sample 650 out of the plurality of electrodes of the objective lens 540. When the adsorption electrode 550 is disposed at a position too far from the sample 650, the adsorbing force by the electrostatic attracting force may not sufficiently reach the foreign matter. Therefore, the adsorption electrode 550 is preferably disposed at a position close to the surface of the sample 650 so that the electrostatic attracting force fully acts on the foreign matter on the sample 650. The adsorption electrode 550 may be disposed at any position close to the surface of the sample 650. As described above, the adsorption electrode 550 may also be disposed as part of the electrode 541 closest to the sample 650 of the objective lens 540. This can facilitate the work for arranging the adsorption electrode 550 while arranging the adsorption electrode 550 at a position sufficiently close to the sample 650.

Furthermore, in the case of the adsorption electrode 550 is arranged as part of and incorporated in the electrode 541 of the objective lens 540, the adsorption electrode 550 is configured so as to be able to perform charge control different from and independent of charge control of the electrode 541 of the objective lens 540. The objective lens 540 needs to acquire the charge information (voltage contrast) of the surface of the sample 650, therefore, the potential of the objective lens 540 is determined from the standpoint of effective acquisition of charge information. On the other hand, the adsorption electrode 550 needs to be charged with a polarity opposite to the charge polarity of the foreign matter to adsorb the foreign matter on the sample 650. Therefore, the adsorption electrode 550 needs to independently perform an operation different from the operation of the electrode 541 of the objective lens 540. Therefore, the adsorption electrode control unit 555 performs separate and independent control. In this case, when the adsorption electrode 550 does not perform the adsorption operation, the adsorption electrode 550 may be controlled to the same potential as that of the electrode 541 of the objective lens. Thus, while not performing the adsorption operation, the adsorption electrode 550 preferably operates in such a way that the objective lens 540 sufficiently performs the original function.

When the adsorption electrode 550 is disposed as part of the electrode 541 of the objective lens 540, the adsorption electrode 550 is suitably disposed outside the electrode 541. The objective lens 540 needs to fully perform the original function of focusing when the electron beam enters the sample 650. In the step of acquiring charge information on the surface of the sample 650, the influence of the adsorption electrode 550 should be avoided. Therefore, the adsorption electrode 550 is preferably disposed on the outside perimeter of the objective lens 540.

The collection electrode 560 is an electrode for collecting the foreign matter adsorbed by the adsorption electrode 550. When the foreign matter is stuck to the adsorption electrode 550 and the amount of foreign matter increases, the adsorption electrode 550 cannot further adsorb foreign matter. Therefore, the foreign matter needs to be collected. The collection electrode 560 is provided to attain this object. The collection electrode 560 may be arranged as part of and incorporated in the stage 570. As the stage 570 moves, the collection electrode 560 can suitably move to a position facing the adsorption electrode 550. This embodiment moves the collection electrode 560 to a position facing the adsorption electrode 550 in the vertical direction as the stage 570 moves, cuts a power supply to the adsorption electrode 550 and charges the collection electrode 560 so as to have a polarity different from that of the foreign matter. Therefore, the collection electrode 560 can easily perform electrostatic adsorption of the foreign matter adsorbed by the adsorption electrode 550.

Charge control over the collection electrode 560 may be performed by the collection electrode control unit 565 based on charge information sent from the foreign matter detection section 595.

In the example of FIG. 27, the charged particle beam apparatus 700 uses a mapping and projection method. An electron beam diagonally enters the sample 650, the charge information acquisition section 590 located vertically above forms and acquires an image of the charge image and detects foreign matter based on the charge image. However, the present invention is also applicable to a so-called SEM type foreign matter inspection apparatus which applies a scanning electron microscope. The adsorption electrode 550 and collection electrode 560 may be provided at positions similar to those in FIG. 27. The electron gun 510 may be disposed vertically above and the charge information acquisition section 590 may be diagonally disposed. The sample 650 may be scanned using a narrowed electron beam to acquire charge information on the surface of the sample 650.

Next, referring to FIG. 28 to FIG. 30, the operation of the foreign matter adsorption step by the charged particle beam apparatus 700 with the above described configuration will be explained.

Figure 28:
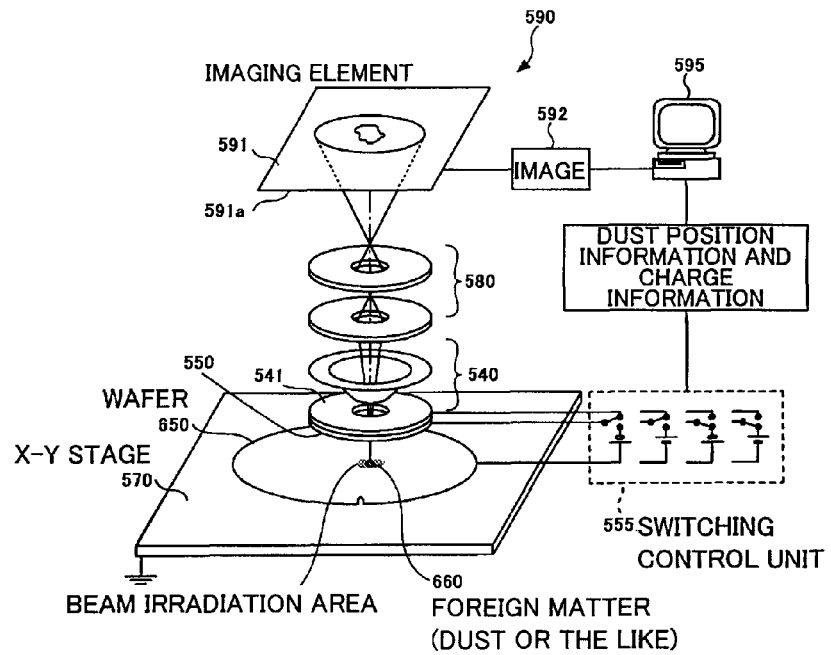
FIG. 28 is a perspective view showing a foreign matter detection step of detecting foreign matter such as dust on a sample.

FIG. 28 is a perspective view showing the foreign matter detection step of detecting foreign matter such as dust on the sample 650. The following explanations will refer to schematic views where only components necessary for explanations are extracted.

In FIG. 28, a semiconductor wafer which is the sample 650 is mounted on the X-Y stage 570. Furthermore, FIG. 28 shows the objective lens 540, secondary electron optical system 580, charge information acquisition section 590, foreign matter detection section 595 and adsorption electrode control unit 555. The charge information acquisition section 590 includes the detector 591 and storage section 592. In the objective lens 540, the electrode 541 approaches the foreign matter. The adsorption electrode 550 is attached to the electrode 541. Foreign matter or impurity such as dust is stuck to the surface of the semiconductor wafer which is the sample 650. The charged particle beam apparatus 700 of this embodiment and the foreign matter removing method using this apparatus are applicable to various types of sample 650. Particularly, foreign matter such as micro dust becomes an issue in the manufacturing of semiconductor wafers. Therefore, the charged particle beam apparatus 700 of this embodiment is suitably applicable to a foreign matter inspection of a semiconductor wafer. Therefore, a semiconductor wafer is used as the sample 650 in this example.

Since FIG. 28 presupposes irradiation of an electron beam, the electron gun 510 and primary electron optical system 520 are omitted from the drawing. The electron beam is irradiated onto the sample 650 and secondary electrons are emitted from the sample 650. The emitted secondary electrons are accelerated upward by the objective lens 540, guided to the detection surface 591*a* of the detector 591 by the secondary electron optical system 580 and a charge image of the surface of the sample 650 is formed on an imaging element composing the detection surface 591*a*. The charged state of a potential distribution or the like on the sample 650 can be known from this charge image. The charged state varies from one position to another depending on whether foreign matter exists or not. Therefore, it is possible to know whether foreign matter exists or not. When foreign matter exists, the position of the foreign matter and the charged state thereof can be known.

The acquired charge image is stored in the storage section 592. The stored charge image is analyzed by the foreign matter detection section 595 and position information and charge information on the foreign matter such as dust are thereby acquired and detected. The foreign matter detection information is sent to the adsorption electrode control unit 555 and used to control the adsorption operation of the adsorption electrode 550. The adsorption electrode control unit 555 may be provided with, for example, a switching control unit shown in FIG. 28 so that the adsorption electrode 550 can be charged with a desired positive or negative polarity.

Figure 29:
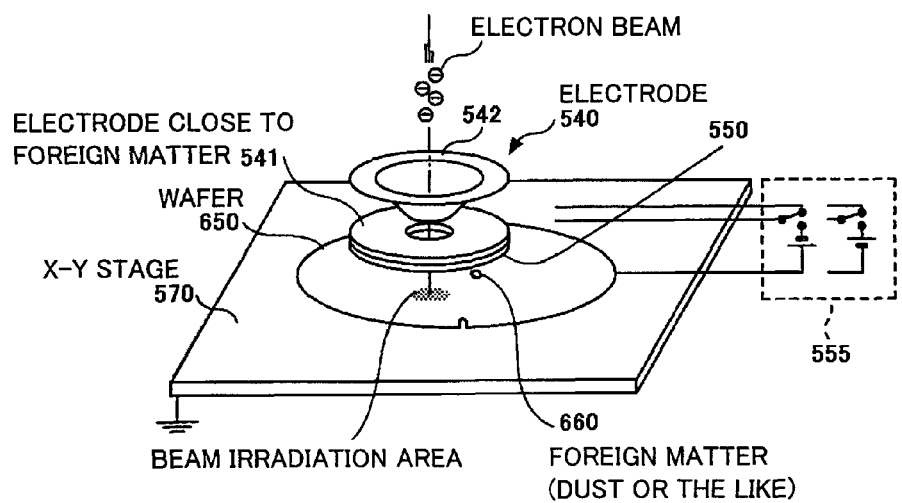
FIG. 29 shows a step of moving an X-Y stage after the foreign matter detection step.

FIG. 29 shows a stage moving step of moving the X-Y stage 570 after the foreign matter detection step shown in FIG. 28. The components of FIG. 29 have already been explained with reference to FIG. 28, and therefore explanations thereof will be omitted here.

FIG. 29 shows a situation in which the foreign matter 660 is detected, the position and charge information of the foreign matter are acquired and then the X-Y stage 570 is moved so as to allow the detected foreign matter 660 to approach the adsorption electrode 550. In this case, a power switch for the switching control unit of the adsorption electrode control unit 555 may be set in an OFF position. In this condition, foreign matter inspection may be continued in other areas of the sample 650, and wherein foreign matter may be detected in the other irradiation areas sequentially by moving the X-Y stage 570. Furthermore, the X-Y stage 570 may be moved according to any one of a continuous moving scheme and a step-and-repeat scheme. The continuous moving scheme continuously moves the X-Y stage 570 while irradiating an electron beam onto the sample 650. The step-and-repeat scheme irradiates an electron beam onto the sample 650 while keeping the X-Y stage 570 stationary, moves the X-Y stage 570 when foreign matter inspection on a predetermined area is finished and irradiates an electron beam onto other inspection areas.

Figure 30:
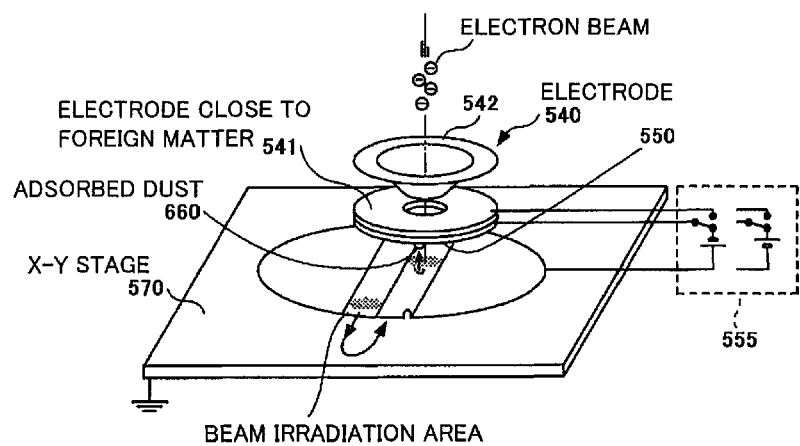
FIG. 30 shows a step of adsorbing detected foreign matter to an adsorption electrode.

FIG. 30 shows an adsorption step in which the detected foreign matter 660 is adsorbed to the adsorption electrode 550. When the X-Y stage 570 moves and the foreign matter 660 approaches the immediate neighborhood right below the adsorption electrode 550, the switching control unit of the adsorption electrode control unit 555 turns on the switch, a voltage is applied to the adsorption electrode 550 and the adsorption electrode 550 is charged. The adsorption electrode control unit 555 performs charge control based on the charge information of the foreign matter 660 so that the adsorption electrode 550 is charged with a polarity opposite to the polarity of the foreign matter 660. This causes an electrostatic attracting force to act on the foreign matter 660 from the adsorption electrode 550 and foreign matter is adsorbed to the adsorption anode 550 provided above the foreign matter 660 as shown in FIG. 30.

As has been explained with reference to FIG. 28 to FIG. 30, this embodiment detects the foreign matter 660, acquires position information and charge information thereof, moves the X-Y stage 570 based on this information and charges, when the foreign matter 660 approaches the adsorption electrode 550, the adsorption electrode 550 with a polarity different from that of the foreign matter 660. Therefore, it is possible to remove the foreign matter 660 on the sample 650 with minimum energization in the flow of the foreign matter inspection process.

When not adsorbing the foreign matter 660, the adsorption electrode 550 may be controlled so as to be charged with the same potential as that of the electrode 541 of the objective lens 540. In this case, the adsorption electrode 550 is in a standby mode. Therefore, the adsorption electrode 550 can also function as the objective lens 540.

In the foreign matter adsorption step explained in FIG. 28 to FIG. 30, the foreign matter 660 is charged through the irradiation of an electron beam upon inspection of foreign matter. Therefore, the foreign matter removing method and charged particle beam apparatus 700 according to this embodiment can be said to be a technique of removing foreign matter by effectively using the charge energy of an electron beam in a normal foreign matter inspection.

Next, referring to FIG. 31 and FIG. 32, the foreign matter removing method using the charged particle beam apparatus 700 of this embodiment will be explained using an example where a charge polarity of foreign matter is positive.

Figure 31:
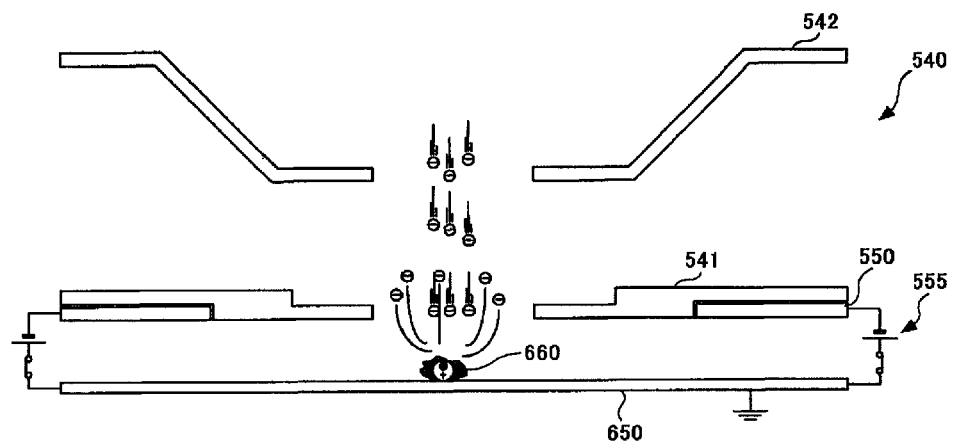
FIG. 31 shows the foreign matter detection step in the case of positively charged foreign matter.

FIG. 31 shows a foreign matter detection step when the foreign matter 660 is positively charged. In FIG. 31, the foreign matter 660 exists on the sample 650. The objective lens 540 has an electrode 541 disposed closest to the sample 650 and an electrode 542 disposed farther from the sample 650. The adsorption electrode 550 is disposed on the outer perimeter of the electrode 541. The adsorption electrode 550 is connected to the adsorption electrode control unit 555 such that charge timing thereof can be controlled.

When the foreign matter 660 such as dust on the sample 650 is irradiated with an electron beam, secondary electrons are emitted from the foreign matter 660. When the quantity of emitted secondary electrons is greater than the quantity of incident electrons of the irradiated electron beam, the quantity of electrons remaining in the foreign matter 660 is decreased and the foreign matter 660 is positively charged (the quantity of electrons corresponds to number of electrons, and the same applies hereafter). This is called "positive charge." Whether the foreign matter 660 is positively charged or negatively charged depends on an emission rate of secondary electrons of the foreign matter 660. That is, when the emission rate of secondary electrons of the foreign matter 660 is greater than 1, the foreign matter 660 is positively charged. Furthermore, the sample 650 itself also has an intrinsic emission rate of secondary electrons. Therefore, when an electron beam is irradiated, the quantity of secondary electrons differs in the sample 650 and foreign matter 660. It is possible to acquire image contrast (charge information) produced by the difference in the quantity of secondary electrons and detect the number of pieces and position of foreign matter 660. In FIG. 31, the sample 650 has the nature of being positively charged by irradiation of the electron beam. The sample 650 emits five electrons against three incident electrons and is thereby positively charged. Therefore, the foreign matter 660 can be positively charged through irradiation of the electron beam. In order to adsorb and remove the foreign matter 660 of such nature, the adsorption electrode 550 is preferably negatively charged. Therefore, in FIG. 31, the adsorption electrode 550 is connected to the negative pole of the power supply of the adsorption electrode control unit 555.

Figure 32:
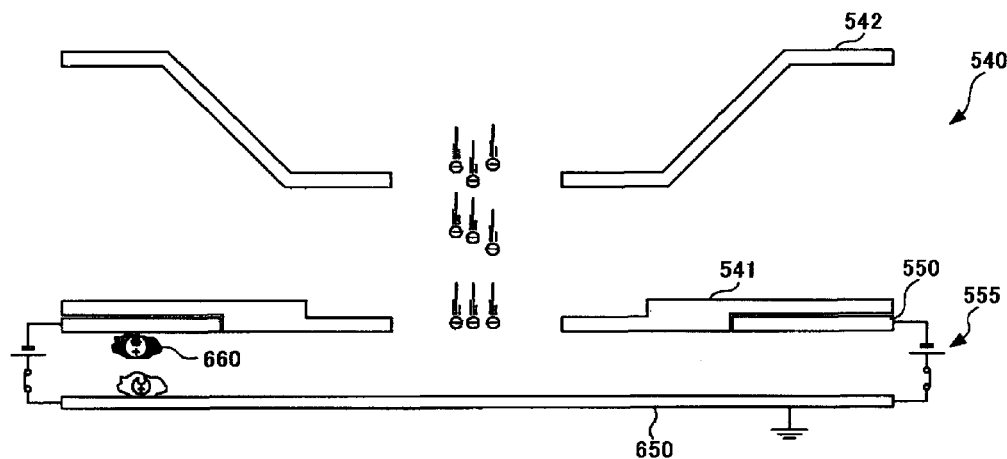
FIG. 32 shows a situation in which positively charged foreign matter is adsorbed to the adsorption electrode.

FIG. 32 shows a situation in which the positively charged foreign matter 660 is adsorbed by the adsorption electrode 550. The stage 570 moves from the state in FIG. 31 (foreign matter 660 is positively charged). The stage 570 moves the foreign matter 660 to a position facing the adsorption electrode 550. The negatively charged adsorption electrode 550 electrostatically adsorbs the foreign matter 660. This state is shown in FIG. 32. Therefore, it is possible to remove the foreign matter 660 existing on the surface of the sample 650.

Thus, when the foreign matter 660 is positively charged through irradiation of the electron beam, the adsorption electrode control unit 555 is suitably configured so as to be able to negatively charge the adsorption electrode 550.

Next, referring to FIG. 33 and FIG. 34, a foreign matter collection step will be explained. In this step, the collection electrode 560 collects the foreign matter 660 electrostatically adsorbed by the adsorption electrode 550.

Figure 33:
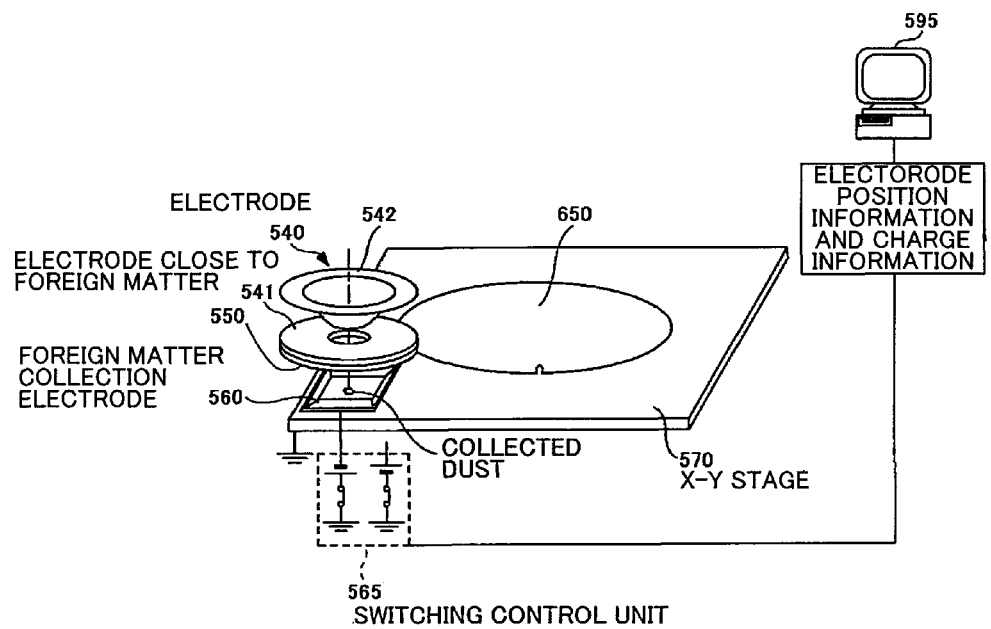
FIG. 33 is a perspective view showing how a foreign matter collection step is carried out.

FIG. 33 is a perspective view showing a situation in which the foreign matter collection step is being executed. In FIG. 33, the sample 650 is mounted in the center of the X-Y stage 570. The collection electrode 560 is provided at an outer edge of the X-Y stage 570 to collect foreign matter. The collection electrode 560 is connected to the collection electrode control unit 565 having a switching control unit and furthermore the collection control electrode unit 565 is connected to a computer which is the foreign matter detection section 595.

As described above, in the foreign matter detection step, it is possible to recognize the number of pieces and size of foreign matter 660 and know the amount of foreign matter 660. Therefore, by executing the adsorption step of adsorbing and removing the foreign matter 660, it is possible to know the amount of adsorption of the foreign matter 660 to the adsorption electrode 550. When the foreign matter 660 adsorbed to the adsorption electrode 550 reaches a certain amount, the surface of the adsorption electrode 550 is covered with the foreign matter 660, preventing the adsorption electrode 550 from further adsorbing the foreign matter 660. Therefore, it is preferable to collect the foreign matter 660 stuck to the adsorption electrode 550 on or before reaching the amount of foreign matter 660 that can be adsorbed by the adsorption electrode 550. The collection electrode 560 perform the function of re-adsorbing and collecting the foreign matter 660 stuck to the adsorption electrode 550.

In FIG. 33, the information on the amount of foreign matter 660 adsorbed by the adsorption electrode 550 may be sent, for example, from the foreign matter detection section 595 to the collection electrode control unit 565 and used to control the operation of the collection electrode 560. When the amount of foreign matter 660 adsorbed by the adsorption electrode 550 reaches a predetermined amount, the stage control unit 571 moves the X-Y stage 570 and positions the collection electrode 560 right below the adsorption electrode 550. In this state, the charge of the adsorption electrode 550 is weakened and thereby the electrostatic attracting force acting on the foreign matter 660 is weakened. At the same time, a voltage is applied to the collection electrode 560 so as to be charged with a polarity different from that of the foreign matter 660. The foreign matter 660 is attracted by the electrostatic attracting force of the collection electrode 560 and stuck to the collection electrode 560. This ensures that the collection electrode 560 collects the foreign matter 660 adsorbed to the adsorption electrode 550. Here, the foreign matter 660 can also be collected without using the collection electrode 560. For example, a predetermined collection area is provided at an end of the X-Y stage 570. The passage of current to the adsorption electrode 550 is simply cut when the collection area faces the adsorption electrode 550. The electrostatic attracting force disappears and the foreign matter is collected. However, when the collection electrode 560 is not used, the foreign matter 660 may not properly drop onto the predetermined collection area. Moreover, the collection may take time. Therefore, the charged particle beam apparatus 700 is preferably provided with the collection electrode 560.

AS described above, even when the amount of foreign matter 660 is large, the collection electrode 560 can continuously adsorb and remove the foreign matter 660 from above the sample 650. Furthermore, it is possible to reliably and speedily collect the foreign matter 660 stuck to the adsorption electrode 550 by the electrostatic attracting force of the collection electrode 560.

Figure 34:
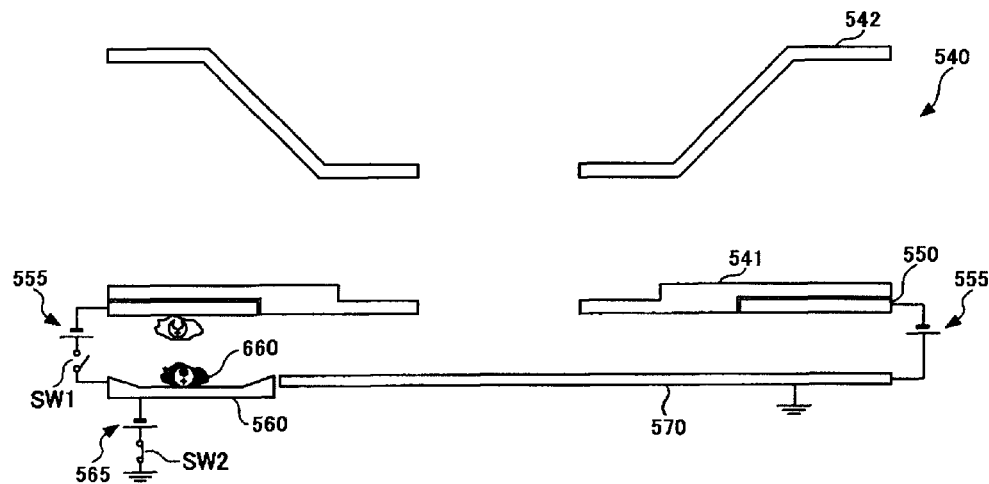
FIG. 34 is a side view showing how positively charged foreign matter is collected by a collection electrode.

FIG. 34 is a side view showing a situation in which the foreign matter 660 in a positively charged state is collected by the collection electrode 560. In FIG. 34, the collection electrode 560 is provided at an end of the stage 570. The collection electrode 560 is connected to the negative terminal of the power supply of the collection electrode control unit 565. Furthermore, the adsorption electrode 550 is provided on the perimeter of the electrode 541 of the objective lens closest to the foreign matter 660. The adsorption electrode 550 is connected to the negative terminal of the power supply of the adsorption electrode control unit 555. Furthermore, the adsorption electrode control unit 555 is provided with a switch SW1 that can turn ON/OFF the connection to the power supply and the collection electrode control unit 565 is likewise provided with a switch SW2 that can turn ON/OFF the connection to the power supply.

In the example in the figure, the foreign matter 660 is positively charged, the adsorption electrode 550 is negatively charged and the foreign matter 660 is adsorbed to the adsorption electrode 550. In this state, the adsorption electrode control unit 555 turns OFF the switch SW1 and cuts the charge of the adsorption electrode 550. At the same time, the collection electrode control unit 565 turns ON the switch SW2 so as to negatively charge the collection electrode 560. This causes the electrostatic attracting force acting on the foreign matter 660 to be switched from an upward force to a downward force and the foreign matter 660 is collected and adsorbed to the collection electrode 560.

Figure 35:
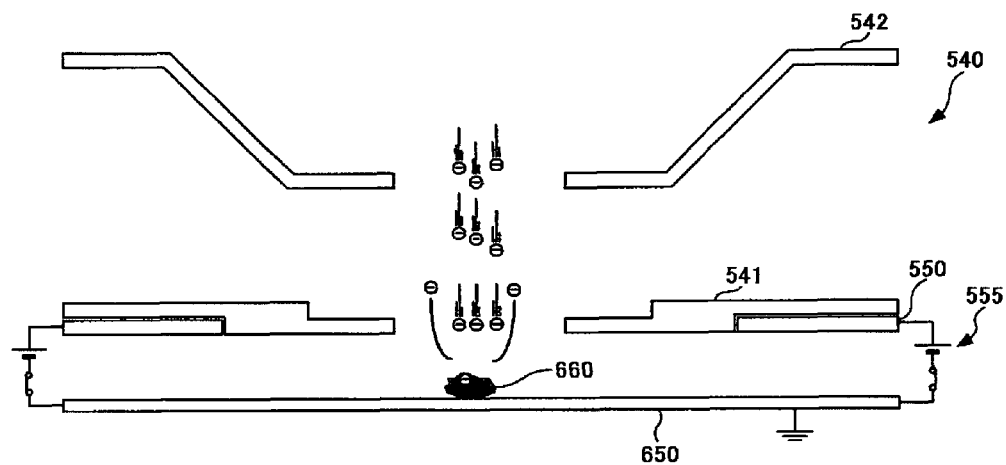
FIG. 35 is a side view showing a foreign matter detection step in the case of negatively charged foreign matter.
Figure 36:
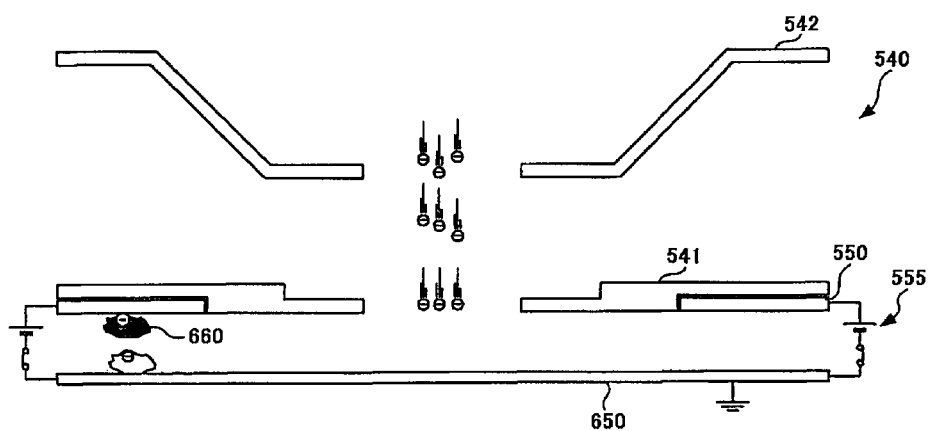
FIG. 36 is a side view showing an adsorption step in the case of negatively charged foreign matter.
Figure 37:
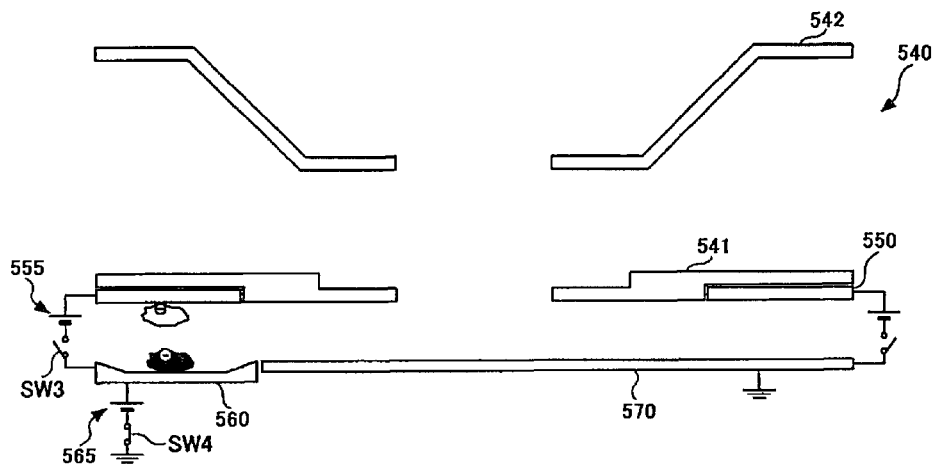
FIG. 37 is a side view showing a collection step in the case of negatively charged foreign matter.

Next, FIG. 35 to FIG. 37 show another series of foreign matter removing steps explaining the foreign matter removing method when the foreign matter 660 is negatively charged.

FIG. 35 is a side view showing the foreign matter detection step in the case of negative charge. The respective components in FIG. 35 are the same as the components in FIG. 31, and so explanations thereof will be omitted.

In FIG. 35, an electron beam is irradiated onto the foreign matter 660. In this example, the secondary electron emission rate of the foreign matter 660 is smaller than 1 and the foreign matter 660 is negatively charged. In FIG. 35, three electrons enter and only two electrons are emitted, and the number of electrons in the foreign matter 660 increases and the foreign matter 660 is thereby negatively charged. The sample 650 has an intrinsic secondary electron emission rate different from that of the foreign matter 660. It is possible to acquire image contrast based on the difference in this emission rate and thereby know the position and charge information on the foreign matter 660. The adsorption electrode control unit 555 performs power supply connection control so as to positively charge the adsorption electrode 550 based on the information indicating that the foreign matter 660 is negatively charged.

FIG. 36 is a side view showing the adsorption step when the foreign matter 660 is negatively charged and the respective components in FIG. 36 are the same as those in FIG. 35, and so explanations thereof will be omitted.

In FIG. 36, as the stage 570 moves, the foreign matter 660 on the sample 650 moves to a position approaching the adsorption electrode 550. When the foreign matter 660 reaches the position right below the facing adsorption electrode 550, the adsorption electrode 555 is positively charged. The adsorption electrode 555 adsorbs the negatively charged foreign matter 660 by an electrostatic attracting force.

FIG. 37 is a side view showing the collection step when the foreign matter 660 is negatively charged. The respective components in FIG. 37 are the same as those in FIG. 34. However, in FIG. 37, the power supply polarity of the adsorption electrode control unit 555 is reversed and the power supply polarity of the collection electrode control unit 565 is reversed.

In FIG. 37, the collection electrode 560 is provided at an end of the stage 570. As the stage 570 moves, the collection electrode 560 approaches the adsorption electrode 550 up to a position facing the adsorption electrode 550. As opposed to the negatively charged foreign matter 660, the adsorption electrode 550 is positively charged by the adsorption electrode control unit 555. This causes the adsorption electrode 550 to adsorb the foreign matter 660. Here, the adsorption electrode control unit 555 turns OFF the switch SW3 and cuts the positive charge of the adsorption electrode 550. The collection electrode control unit 565 turns ON a switch SW4 so as to positively charge the collection electrode 565. This causes the negatively charged foreign matter 660 to be collected and adsorbed to the collection electrode 560 by an electrostatic attracting force.

As mentioned above, when the foreign matter 660 is negatively charged, the adsorption electrode 550 and collection electrode 560 are controlled so as to be positively charged and thereby the foreign matter 660 can be adsorbed and removed from the sample 650 and the adsorbed foreign matter 660 is collected. The foreign matter adsorption removing step can thereby be repeated.

Next, referring to FIG. 38 and FIG. 39 various examples of the adsorption electrode 550 will be explained.

Figure 38:
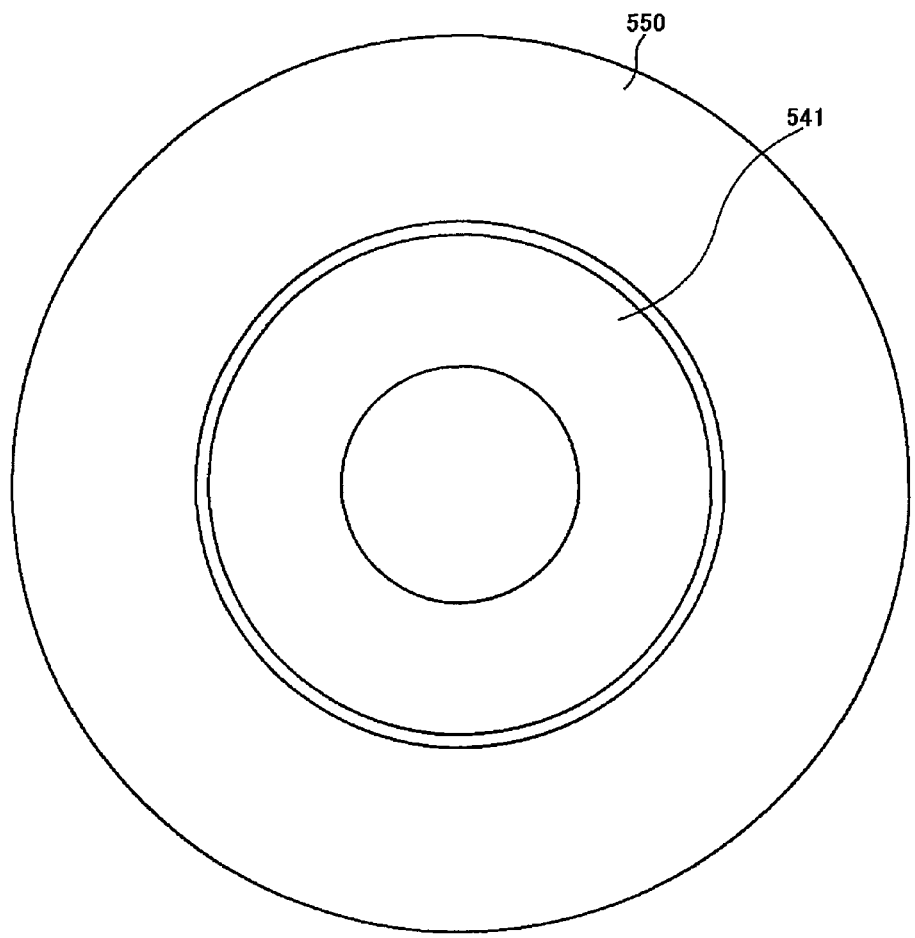
FIG. 38 is a bottom view showing the bottom of an electrode of an objective lens.

FIG. 38 is a bottom view showing the bottom of the electrode 541 of the objective lens 540. As described above, the electrode 541 is disposed closest to the sample 650 out of the plurality of electrodes of the objective lens 540. As shown in FIG. 38, the adsorption electrode 550 is disposed so as to surround the electrode 541 in a ring shape. In the foreign matter detection step, the electrode 541 in the center functions as the objective lens. In the foreign matter adsorption step, the detected foreign matter 660 moves to the position facing the adsorption electrode 550 provided outside the electrode 541. This minimizes the influence of the charge of the adsorption electrode 550 on the foreign matter detection step regardless of the charge polarity of the foreign matter 660.

Figure 39:
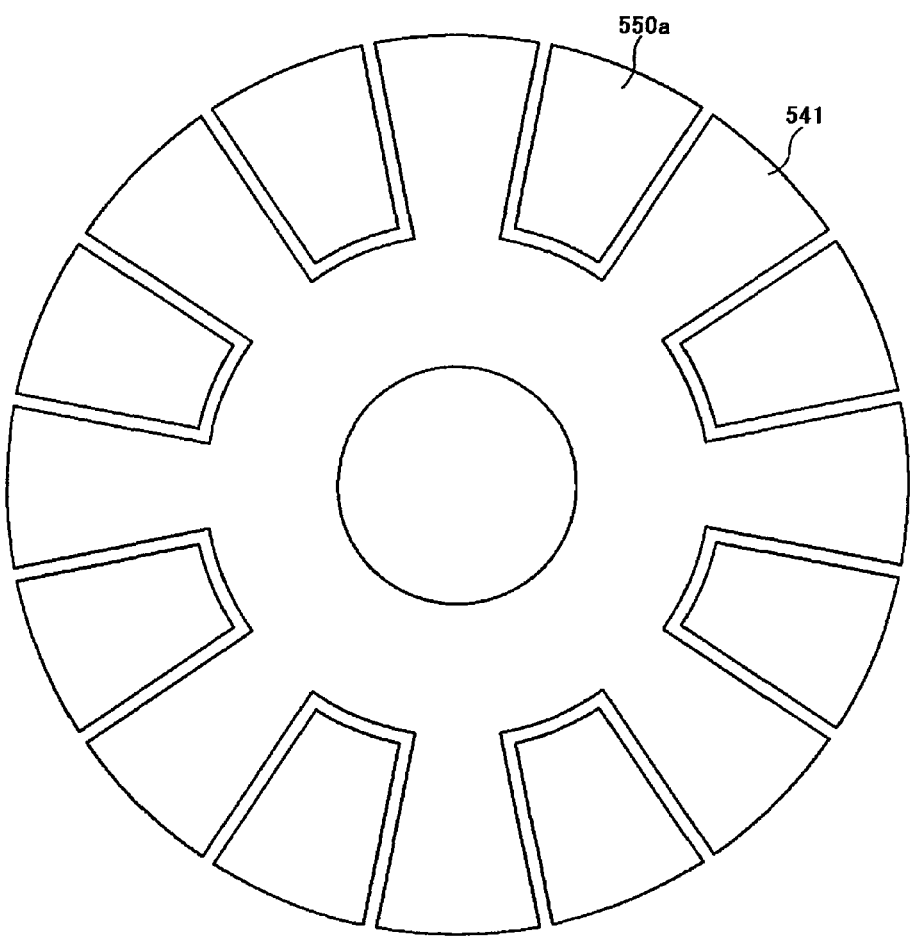
FIG. 39 is a bottom view showing the bottom of an electrode according to an embodiment different from that in FIG. 38.

FIG. 39 is a bottom view showing the bottom of the electrode 541 having a configuration different from that in FIG. 38. In FIG. 39, unlike the configuration in FIG. 38, the adsorption electrode 550a is provided radially around the electrode 541 instead of being provided on the whole perimeter of the electrode 541. Though the area of the adsorption electrode 550a is reduced, the adsorption electrode 550a can adsorb and remove the foreign matter 660. In this example, a greater area of the electrode 541 is left. Upon adsorption of foreign matter, the adsorption electrode 550a is charged, and on the other hand, the foreign matter detection step is performed in the center. This example can further reduce the influence of the charge of the adsorption electrode 550a.

Next, another example of the collection electrode will be explained referring to FIG. 40 and FIG. 41.

Figure 40:
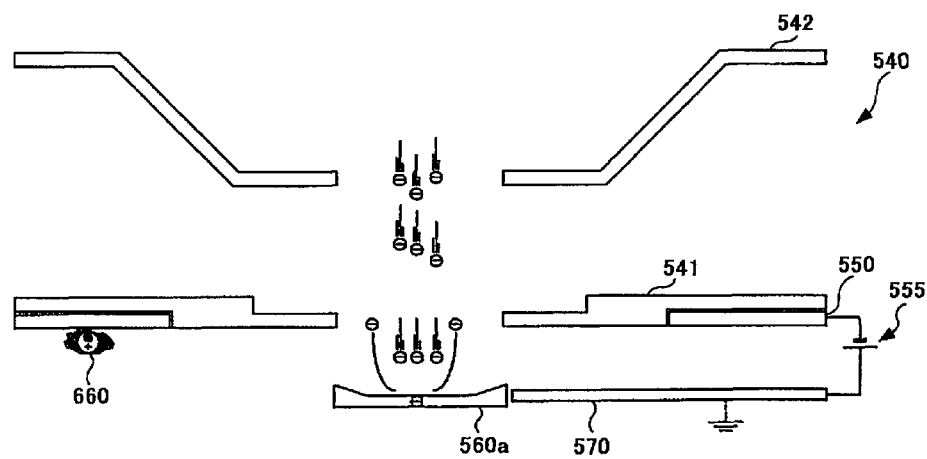
FIG. 40 is a side view showing an embodiment provided with a collection electrode charged with an electron beam.

FIG. 40 is a side view of another example of the collection electrode 560a. In this example, a voltage is not directly applied to the collection electrode 560a. The collection electrode 560a is charged using an electron beam. In FIG. 40, since the foreign matter 660 is positively charged, the adsorption electrode 550 is negatively charged and the foreign matter 660 is adsorbed to the adsorption electrode 550. The surface of the collection electrode 560a is made of a material having a secondary electron emission efficiency less than 1. When an electron beam is irradiated onto the collection electrode 560a made of such a material, the collection electrode 560a is negatively charged.

Figure 41:
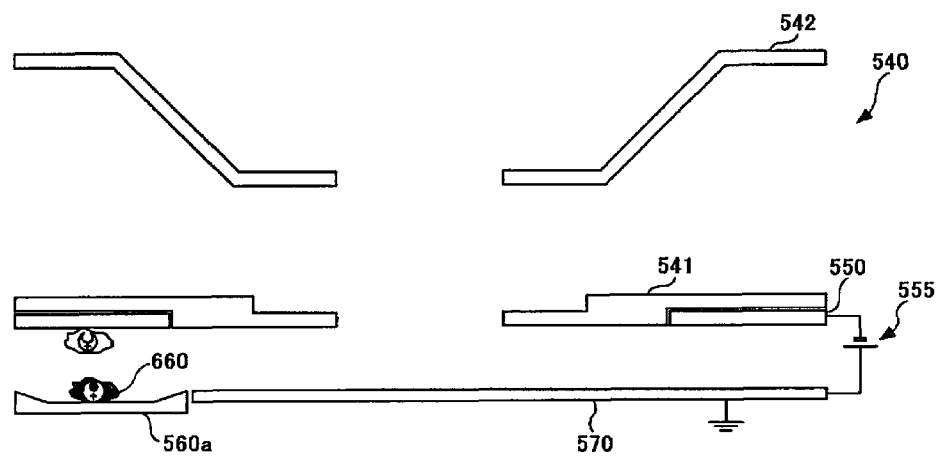
FIG. 41 is a side view showing a collection step in the case of a negatively charged collection electrode.

FIG. 41 is a side view showing the collection step using the collection electrode 560a. The collection electrode 560a is made of a material negatively charged through irradiation of an electron beam as described above. Therefore, in FIG. 40, the collection electrode 560a is negatively charged through the irradiation of the electron beam. The stage 570 is moved and the collection electrode 560 is moved to a position right below the adsorption electrode 550. In this state, the negative charge to the adsorption electrode 550 is cut. Since the collection electrode 560a is negatively charged, the positively charged foreign matter 660 is absorbed to and collected by the collection electrode 560a.

Therefore, in this embodiment, by using the collection electrode 550a made of a material having a secondary electron emission rate less than 1, the collection electrode 560a is able to collect the positively charged foreign matter 660 without providing the collection electrode control unit 565.

In the case that the foreign matter 660 has the nature ob being negatively charged, the collection electrode 560a is made of a material having a secondary electron emission rate greater than 1 and thereby the collection electrode 560a is able to collect the foreign matter 660 likewise.

Next, referring to FIG. 42 to FIG. 44, charged particle beam apparatuses 700a and 700b will be explained. These configurations can be adapted to the case where the foreign matter 660 can be both positively charged and negatively charged.

Figure 42:
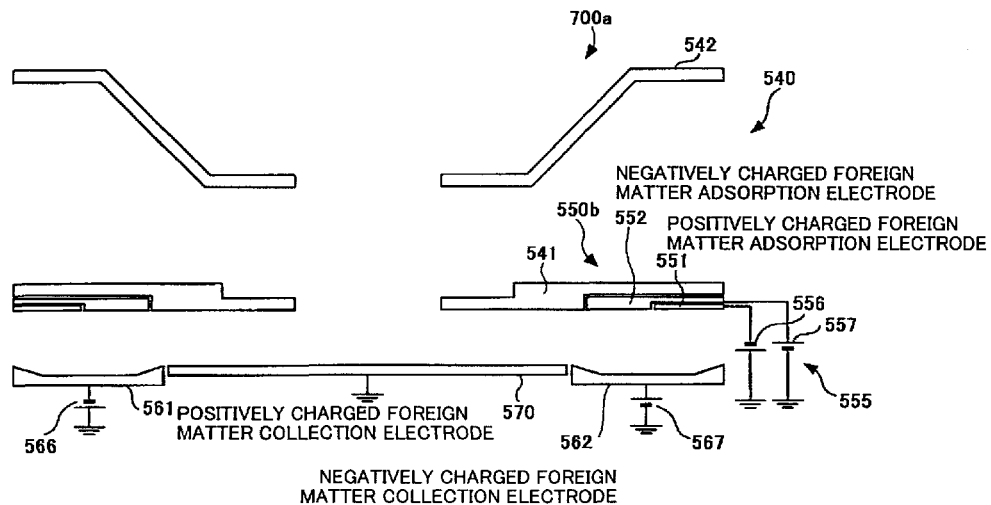
FIG. 42 shows a charged particle beam apparatus provided with both a positively charged adsorption electrode and a negatively charged adsorption electrode.

FIG. 42 shows the charged particle beam apparatus 700a provided with both positively charged adsorption electrode 551 and negatively charged adsorption electrode 552. In FIG. 42, both the positively charged foreign matter adsorption electrode 551 and negatively charged foreign matter adsorption electrode 552 are provided on the perimeter of the electrode 541 of an objective lens 540 closest to a stage 570. The positively charged foreign matter adsorption electrode 551 is provided outside the negatively charged foreign matter adsorption electrode 552. Furthermore, a positively charged foreign matter collection electrode 561 is provided at one outer edge of the stage 570 and a negatively charged foreign matter collection electrode 562 is provided at the other outer edge. An adsorption electrode 550 is connected to an adsorption electrode control unit 555, especially, the positively charged foreign matter adsorption electrode 551 is connected to the negative electrode of a power supply 556 and the negatively charged foreign matter adsorption electrode 552 is connected to the positive electrode of a power supply 557. Furthermore, the positively charged foreign matter collection electrode 561 is connected to the negative electrode of a power supply 566 and the negatively charged foreign matter collection electrode 562 is connected to the positive electrode of a power supply 567.

Therefore, the charged particle beam apparatus 700a is provided with both the positive and negative adsorption electrodes 551 and 552 configured so as to be supplied with both positive and negative potentials by the power supplies 556 and 557. A foreign matter 660 on a sample 650 can be removed irrespective of whether the foreign matter 660 is positively charged or negatively charged. Furthermore, even when the positively charged foreign matter 660 and the negatively charged foreign matter 660 are mixed, such mixed foreign matter 660 can be removed.

More specifically, when the foreign matter 660 approaches an adsorption electrode 550b, the charged particle beam apparatus 700a is controlled according to the charged state of the foreign matter 660. When the foreign matter 660 is positively charged, the positively charged foreign matter adsorption electrode 551 is negatively charged by the power supply 556 and thereby the foreign matter 660 is adsorbed. When the foreign matter 660 is negatively charged, the negatively charged adsorption electrode 552 is positively charged by the power supply 557 and thereby the foreign matter 660 is adsorbed.

Furthermore, the foreign matter is suitably collected as follows. Suppose the positively charged adsorption electrode 551 has adsorbed the positively charged foreign matter 660. In this case, when the stage 570 moves and the positively charged foreign matter collection electrode 566 faces the positively charged foreign matter adsorption electrode 551, the negative charge to the positively charged foreign matter adsorption electrode 551 is cut. Furthermore, the positively charged collection electrode 561 is negatively charged by the power supply 566. Therefore, the positively charged foreign matter 660 is collected. Likewise, when the negatively charged foreign matter 660 is adsorbed to the negatively charged foreign matter adsorption electrode 552, the positive charge of the negatively charged foreign matter adsorption electrode 552 is cut when the negatively charged foreign matter adsorption electrode 552 faces the negatively charged foreign matter collection electrode 562. Furthermore, the negatively charged foreign matter collection electrode 562 is positively charged by the power supply 567. Therefore the negatively charged foreign matter 660 is collected.

AS described above, the charged particle beam apparatus 700a in FIG. 42 is provided with the adsorption electrode 550b including both the positively charged foreign matter adsorption electrode 551 and negatively charged foreign matter adsorption electrode 552, and the collection electrode including both the positively charged foreign matter collection electrode 561 and negatively charged foreign matter collection electrode 562. Therefore, the foreign matter 660 can be adsorbed, removed and collected irrespective of the charged state of the foreign matter 660.

Figure 43:
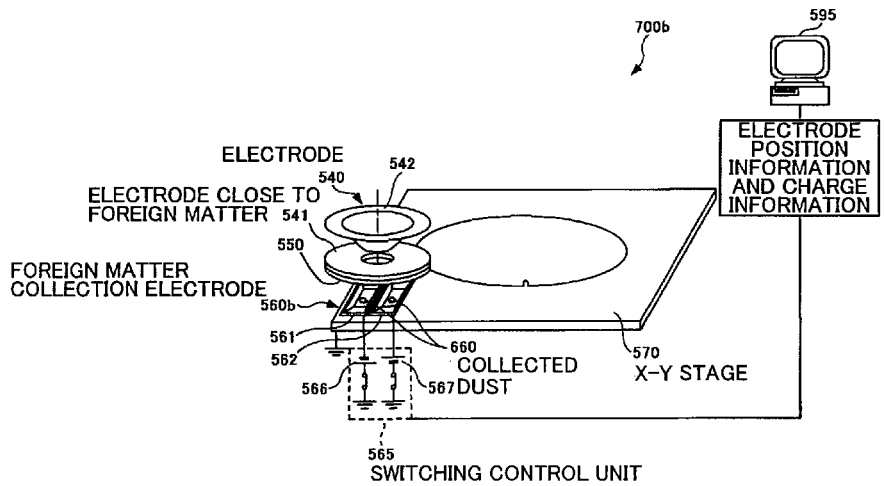
FIG. 43 is a perspective view showing a charged particle beam apparatus provided with a collection electrode different from that in FIG. 42.

FIG. 43 is a perspective view showing a charged particle beam apparatus 700b provided with a collection electrode 560b different from that in FIG. 42. In FIG. 43 like FIG. 42, the collection electrode 560b is provided at an outer edge of the X-Y stage 570. However, FIG. 43 shows a positively charged foreign matter collection electrode 561 and a negatively charged foreign matter collection electrode 562 disposed adjacent to each other. The charge of the collection electrode 560b is controlled by a collection electrode control unit 565. The positively charged foreign matter collection electrode 561 is connected to the negative electrode of a power supply 566 and the negatively charged foreign matter collection electrode 562 is connected to the positive electrode of a power supply 567.

In the foreign matter collection step, when an X-Y stage 570 moves and the collection electrode 560b reaches a position facing and right below an adsorption electrode 550, any one of the positively charged foreign matter collection electrode 561 and negatively charged foreign matter collection electrode 562 is charged according to the charge polarity of an adsorbed foreign matter 660. Therefore, the foreign matter 660 can be collected irrespective of whether the charge polarity of the foreign matter 660 is positive or negative.

The charge polarity of the foreign matter 660 is acquired by the collection electrode control unit 565 based on charge information sent from a foreign matter detection section 595. The above described control is then performed based on the information on the charge polarity.

Figure 44:
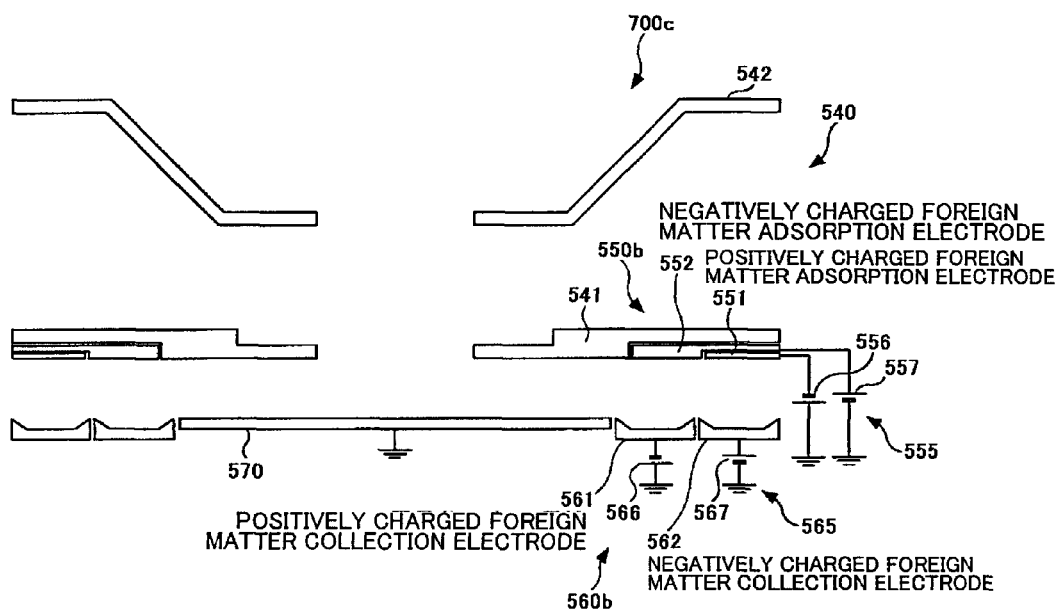
FIG. 44 is a side view showing a charged particle beam apparatus according to an embodiment combining the adsorption electrode of the embodiment in FIG. 42 with the collection electrode of the embodiment in FIG. 43.

FIG. 44 is a side view showing a charged particle beam apparatus 700c having a configuration combining the adsorption electrode 550b in FIG. 42 with the collection electrode 560b in FIG. 43.

In FIG. 44, both a positively charged foreign matter adsorption electrode 551 and a negatively charged foreign matter adsorption electrode 552 are provided as an adsorption electrode 550b adjacent to each other in the diameter direction. On the other hand, a positively charged foreign matter collection electrode 561 and a negatively charged foreign matter collection electrode 562 are provided also as a collection electrode 560b adjacent to each other. Furthermore, the positively charged foreign matter adsorption electrode 551 is connected to the negative electrode of a power supply 556 and the negatively charged foreign matter adsorption electrode 552 is connected to the positive electrode of a power supply 557. Likewise, the positively charged foreign matter collection electrode 561 is connected to a negative electrode of the power supply 566 and the negatively charged foreign matter collection electrode 562 is connected to a positive electrode of the power supply 567.

In such a configuration, as a stage 570 moves, it is possible to appropriately adsorb, remove and collect foreign matter 660 irrespective of whether the foreign matter 660 is positively charged or negatively charged. The positional relationship between the positively charged foreign matter adsorption electrode 551 and the negatively charged foreign matter adsorption electrode 552 may be changed and reversed appropriately. The positional relationship between the positively charged foreign matter collection electrode 561 and the negatively charged foreign matter collection electrode 562 may also be changed and reversed appropriately.

In the example of FIG. 44, the adsorption electrodes 550, 550a and 550b are disposed outside an electrode 541 of an objective lens 540 closest to a sample 650. The collection electrodes 560, 560a and 560b are disposed outside the stage 570. However, these positions can be modified in various ways as far as it is possible to realize a positional relationship that the adsorption electrode and the collection electrode are close to each other.

As has been explained referring to FIG. 33 to FIG. 44, this embodiment provides the collection electrodes 560, 560a and 560b on the stage 570. Therefore, it is possible to collect the foreign matter 660 stuck to the adsorption electrodes 550, 550a and 550b during operation of moving the stage 570 to observe and measure the foreign matter on the sample 650. This eliminates the necessity for a special operation or mechanism to collect the foreign matter 660. Furthermore, according to such a configuration, it is possible to collect the foreign matter 660 periodically from the adsorption electrodes 550, 550a and 550b. Therefore, the adsorption electrodes 550, 550a and 550b can be periodically restored to a clean state. Therefore, it is possible to prevent the foreign matter stuck to the adsorption electrodes 550, 550a and 550b from dropping again onto the sample 650 such as a wafer.

Furthermore, the charged particle beam apparatuses 700, 700a, 700b and 700c of this embodiment collect the foreign matter 660 while observing and measuring the sample 650 such as a wafer. Observation and measurement may also be performed once again after the collection for confirmation of the collection effect. Furthermore, a series of these operations may be automatically performed according to a provided program or recipe. Alternatively, the operator may directly operate the charged particle beam apparatus.

Persons of ordinary skill in the art will realize that many modifications and variations of the above embodiments may be made without departing from the novel and advantageous features of the present invention. Accordingly, all such modifications and variations are intended to be included within the scope of the appended claims. The specification and examples are only exemplary. The following claims define the true scope and spirit of the invention.

What is claimed is:

1. An electron beam apparatus comprising:
a stage for mounting a sample thereon;
a primary optical system for generating an electron beam having an irradiation area and irradiating the electron beam onto the sample; and
a secondary optical system for detecting electrons which have been generated through irradiation of the electron beam onto the sample and have acquired structural information of the sample and for acquiring an image of the sample about a viewing area, wherein
the irradiation area includes a pre-charge area which precedes the viewing area in a moving direction of the sample,
configured such that a pre-charge in the pre-charge area by the primary optical system and the detection of electrons from the viewing area by the secondary optical system are conducted simultaneously when the stage on which the sample is mounted is moving in the moving direction.

2. The electron beam apparatus according to claim 1, wherein
the pre-charge area emits reflected electrons from open plugs formed on the sample therein, and
the secondary optical system only detects secondary electrons as the electrons that have acquired structural information of the sample in the viewing area.

3. The electron beam apparatus according to claim 1, wherein
the irradiation area has a larger area than the viewing area, and
the irradiation area changing section changes the position of the irradiation area so that the center of the irradiation area is aligned with the center of the viewing area.

4. The electron beam apparatus according to claim 1, wherein
the sample is a semiconductor wafer, and
the secondary optical system detects a short circuit or conduction defect in wiring in the semiconductor wafer by acquiring a voltage contrast image of the semiconductor wafer.

5. The electron beam apparatus according to claim 1, wherein changing the position of the irradiation area preceding the viewing area adjusts the amount of charge in the pre-charge area.

6. The electron beam apparatus according to claim 1, further comprising an irradiation area changing section for changing a position of the irradiation area from a position wherein the viewing area precedes the irradiation area to position wherein the irradiation area includes the pre-charge area therein.

7. The electron beam apparatus according to claim 1, further comprising an irradiation area changing section for changing a position of the irradiation area from a position wherein the irradiation area includes the pre-charge area therein to a position wherein the viewing area precedes the irradiation area.

8. A sample observation method of observing a sample based on an acquired image, comprising:
mounting the sample on a stage;
moving the stage in a moving direction;
generating an electron beam having an irradiation area to irradiate the electron beam onto the sample; and
acquiring an image of the sample about a viewing area by detecting electrons which have been generated through irradiation of the electron beam and have acquired structural information of the sample, wherein
the irradiation area includes a pre-charge area which precedes the viewing area in a moving direction of the sample,
a pre-charge in the pre-charge area and the detection of electrons from the viewing area are conducted simultaneously when the stage is moving.

9. The sample observation method according to claim 8, wherein
- the pre-charge area emits reflected electrons from open plugs formed on the sample therein, and
- in the acquiring step, only secondary electrons are detected as the electrons that have acquired structural information of the sample in the viewing area.

10. The sample observation method according to claim 8, wherein changing the position of the irradiation area preceding the viewing area adjusts the amount of charge in the pre-charge area.

* * * * *